(12) United States Patent
Restifo et al.

(10) Patent No.: US 9,522,948 B2
(45) Date of Patent: Dec. 20, 2016

(54) GP100-SPECIFIC T CELL RECEPTORS AND RELATED MATERIALS AND METHODS OF USE

(71) Applicant: The United States of America, as represented by the Secretary, Department of Health and Human Services, Washington, DC (US)

(72) Inventors: Nicholas P. Restifo, Chevy Chase, MD (US); Lydie Cassard, Antony (FR); Zhiya Yu, Potomac, MD (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 7 days.

(21) Appl. No.: 14/106,031

(22) Filed: Dec. 13, 2013

(65) Prior Publication Data

US 2014/0219978 A1  Aug. 7, 2014

Related U.S. Application Data

(60) Continuation of application No. 13/483,286, filed on May 30, 2012, now Pat. No. 8,613,932, which is a division of application No. 12/522,321, filed as application No. PCT/US2008/050841 on Jan. 11, 2008, now Pat. No. 8,216,565.

(60) Provisional application No. 60/884,732, filed on Jan. 12, 2007, provisional application No. 60/885,724, filed on Jan. 19, 2007.

(51) Int. Cl.
| | |
|---|---|
| *C07H 21/02* | (2006.01) |
| *C12N 15/00* | (2006.01) |
| *C07K 14/705* | (2006.01) |
| *C07K 14/725* | (2006.01) |
| *C07K 16/30* | (2006.01) |
| *C12N 15/85* | (2006.01) |
| *C12N 15/86* | (2006.01) |
| *G01N 33/574* | (2006.01) |
| *A61K 38/00* | (2006.01) |

(52) U.S. Cl.
CPC ..... *C07K 14/70503* (2013.01); *C07K 14/7051* (2013.01); *C07K 16/30* (2013.01); *C12N 15/85* (2013.01); *C12N 15/86* (2013.01); *G01N 33/57492* (2013.01); *A61K 38/00* (2013.01)

(58) Field of Classification Search
USPC ............. 536/23.1, 23.5; 435/320.1
See application file for complete search history.

(56) References Cited

U.S. PATENT DOCUMENTS

| | | | |
|---|---|---|---|
| 4,450,150 | A | 5/1984 | Sidman |
| 5,087,616 | A | 2/1992 | Myers et al. |
| 5,225,539 | A | 7/1993 | Winter |
| 5,449,752 | A | 9/1995 | Fujii et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits et al. |
| 6,080,840 | A | 6/2000 | Slanetz et al. |
| 6,265,150 | B1 | 7/2001 | Terstappen et al. |
| 6,511,830 | B1 | 1/2003 | Takahashi et al. |
| 2002/0197266 | A1 | 12/2002 | Debinski |
| 2009/0232839 | A1 | 9/2009 | Figdor et al. |
| 2010/0015113 | A1 | 1/2010 | Restifo et al. |

FOREIGN PATENT DOCUMENTS

| | | |
|---|---|---|
| EP | 0 239 400 B1 | 9/1987 |
| GB | 2 188 638 A | 10/1987 |
| WO | WO 96/13593 A2 | 5/1996 |
| WO | WO 97/32603 * | 9/1997 |
| WO | WO 98/02538 A1 | 1/1998 |
| WO | WO 01/23577 A2 | 4/2001 |
| WO | WO 2006/031221 A1 | 3/2006 |
| WO | WO 2008/028601 A2 | 3/2008 |

OTHER PUBLICATIONS

U.S. Appl. No. 13/483,286, filed May 30, 2012.
U.S. Appl. No. 12/522,321, filed Aug. 10, 2009.
Boulter et al., "Stable, soluble T-cell receptor molecules for crystallization and therapeutics," *Protein Engineering*, 16 (9), 707-711 (2003).
Bradel-Tretheway et al., "Effects of codon-optimization on protein expression by the human herpes virus 6 and 7 U51 open reading frame," *J Virol Meth.*, 111, 145-156 (2003).
Chen et al., "Safety Testing for Replication-Competent Retrovirus Associated with Gibbon Ape Leukemia Virus-Pseudotyped Retroviral Vectors," *Human Gene Ther.*, 12, 61-70 (2001).
Choi et al., "Synthesis and Assembly of a Cholera Toxin B Subunit-Rotavirus VP7 Fusion Protein in Transgenic Potato," *Mol. Biotechnol.*, 31, 193-202 (2005).

(Continued)

*Primary Examiner* — Maria Leavitt
(74) *Attorney, Agent, or Firm* — Leydig, Voit & Mayer, Ltd.

(57) ABSTRACT

The invention provides human cells, particularly human T cells, comprising a murine T Cell Receptor (TCR) having antigen specificity for the cancer antigen gp100. Isolated or purified TCRs having antigenic specificity for amino acids 154-162 of gp100 (SEQ ID NO: 1), as well as related polypeptides, proteins, nucleic acids, recombinant expression vectors, host cells, populations of cells, antibodies, or antigen binding fragments thereof, conjugates, and pharmaceutical compositions, are further provided. The invention further provides a method of detecting the presence of cancer in a host and a method of treating or preventing cancer in a host comprising the use of the inventive materials described herein.

14 Claims, 24 Drawing Sheets

(56) References Cited

OTHER PUBLICATIONS

Cohen et al., "Enhanced Antitumor Activity of Murine-Human Hybrid T-Cell Receptor (TCR) in Human Lympocytes is Associated with Improved Pairing and TCR/CD3 Stability," *Cancer Res.*, 66 (17), 8878-8886 (2006).
Cohen et al., "Recognition of Fresh Human Tumor by Human Peripheral Blood Lymphocytes Transduced with a Bicistronic Retroviral Vector Encoding a Murine Anti-p53 TCR," *J. Immunology*, 175, 5799-5808 (2005).
Cormier et al., "Comparative Analysis of the In Vivo Expression of Tyrosinase, MART-1/Melan-A, and gp100 in Metastatic Melanoma Lesions: Implications for Immunotherapy," *J. Immunother.*, 21 (1), 27-31 (1998).
Finkelstein et al., "Bedside to bench and back again how animal models are guiding the development of new immunotherapies for cancer," *J. Leukoc. Biol.*, 76, 333-337 (2004).
GenBank Accession No. AAA40223.1 (Downloaded Jan. 29, 2007).
GenBank Accession No. AAB38254 (Downloaded Jan. 29, 2007).
GenBank Accession No. AAL38989.1 (Downloaded Jan. 29, 2007).
GenBank Accession No. NM_006928.3 (Downloaded Jul. 6, 2009)).
GenBank Accession No. NP_001019792 (Downloaded Jan. 29, 2007).
GenBank Accession No. NP_008859 (Downloaded Jul. 6, 2009).
GenBank Accession No. XP_897477.1 (Downloaded Jan. 29, 2007).
GenBank Accession No. AAB38251.1 (Downloaded Jan. 29, 2007).
Haskard et al., "The Production of Human Monoclonal Autoantibodies from Patients with Rheumatoid Arthritis by the eBV-Hybidoma Technique," *J. Immunol. Methods*, 74 (2), 361-367 (1984).
Hoashi et al., "MART-1 Is Required for the Function of the Melanosomal Matrix Protein PMEL17/GP100 and the Maturation of Melanosomes," *J. Biol. Chem.*, 280 (14), 14006-14016 (2005).
Hudecz, "Synthesis of Peptide Bioconjugates," F., *Methods Mol. Biol.*, 298, 209-223 (2005).
Huse et al., "Generation of a Large Combinatorial Library of the Immunoglobulin Repertoire in Phage Lambda," *Science*, 246, 1275-1281 (1989).
Jesson et al., "The Immune response to soluble D10 TCR: analysis of antibody and T cell responses," *Internatl. Immunol. 10* (1), 27-35 (1998).
Johnson et al., "Gene therapy with human and mouse T-cell receptors mediates cancer regression and targets normal tissues expressing cognate antigen," *Blood*, 114(3), 535-546 (2009).
Kirin et al., Amino Acid and Peptide Bloconjugates of Copper(II) and Zinc(II) Complexes with a Modified N,N-Bis(2-ploclyl)amine Ligand *Inorg Chem.*, 44 (15), 5405-5415 (2005).
Köhler et al., "Derivation of specific antibody-producing tissue culture and tumor lines by cell fusion," *Eur. J.* Immunol., 6, 511-519 (1976).
Liu et al., "Comparison of Common γ-Chain Cytokines, Interleukin-2, Interleukin-7, and Interleukin-15 for the In Vitro Generation of Human Tumor-Reactive T Lymphocytes for Adoptive Cell Transfer Therapy," *J. Immunother.*, 29 (3), 284-293 (2006).
Manning et al., "Effects of Complementarity Determining Region Mutations on the Affinity of an α/β T Cell Receptor: Measuring the Energy Associated with CD$/CD8 repertoire Skewing," *J. Exp. Med.*, 189(3), 461-471 (Feb. 1, 1999).
Morgan et al. "Cancer regression in patients after transfer of genetically engineered lymphocytes," *Science*, 314, 126-129 (2006).
Morgan et al., "High Efficiency TCR Gene Transfer Into Primary Human Lymphocytes Affords Avid Recognition of Melanoma Tumor Antigen Glycoprotein 100 and Does Not Alter the Recognition of Autologuous Melanomia Antigens," *J. Immunology*, 171, 3287-3295 (2003).
Morgan et al., "Cancer Regression in Patients After Transfer of Genetically Engineered Lymphocytes," *Sciencexpress*, e-publication on Aug. 31, 2006.
Ngo et al., "Computational Complexity, Protein Structure Prediction, and the Levinthal Paradox," in The Protein Folding Problem and Tertiary Structure Prediction, Merz et al. (eds.), *Birkhauser Boston*, Boston, MA, 433 and 492-495 (1994).
Parkhurst et al., "Improved Induction of Melanoma-Reactive CTL with Peptides from the Melanoma Antigen gp100 Modified at HLA-A*0201-Binding Residues," *J. Immunol.*, 157 (6), 2539-2548 (1996).
PCT/US2008/050841 International Search Report (Jul. 9, 2008).
Pedersen et al., "Comparison of Surface Accessible Residues in Human and Murine Immunoglobulin Fv Domains," *J. Mol. Biol.*, 235, 959-973 (1994).
Pierce et al., "Combinations of Affinity Enhancing Mutations in a T Cell receptor Reveal Highly Nonadditive Effects within and between Complementarity Determining Regions and Chains," *Biochemistry*, 49, 7050-7059 (2010).
Ramakrishna et al., "Codon Optimization of the Tat Antigen of Human Immunodeficiency Virus Type 1 Generates Strong Immune Responses in Mice following Genetic Immunization," *J Virol.*, 78, 9174-9189 (2004).
Reiter et al., "Engineering Interchain disulfide bonds into conserved framework regions of Fv fragments: improved biochemical characteristics of recombinant immunotoxins containing disulfide-stabilized Fv," *Protein Engineering*, 7, 697-704 (1994).
Roder et al., "The EBV-Hybridoma Technique." *Methods Enzymol.*, 121, 140-167 (1986).
Roitt, Essential Immunology, *Blackwell Scientific Publications, sixth addition*, 47-49 (1988).
Rudinger et al., "Characteristics of the amino acides as components of a peptide hormone sequence," In Peptide Hormones, Parsons (ed.), *University Park Press*: Baltimore, MD, 1-7 (1976).
Saikali et al., "Expression of nine tumour antigens in a series of human glipblastoma multiforme: interest of EGFRvIII, IL-13Rα2, gp100 and TRP-2 for immunotherapy," *J. Neurooncol.*, 81 (2), 139-148 (2007).
Schaft et al., "A new way to generate cytolytic tumor-specific T cells: electgroporation of RNA coding for a T cell receptor into T lymphocytes," *Cancer Immunol. Immunother.*, 55, 1132-1141 (2006).
Schaft et al., "Peptide Fine Specificity of Anti-Glycoprotein 100 CTL Is Preserved Following Transfer of Engineered TCRαβ Genes Into Primary Human T Lymphocytes," *J. Immunology*, 170, 2186-2194 (2003).
Skipper et al., "Mass-Spectrometric Evaluation of HLA-A*0201-Associated Peptides Identifies Dominant Naturally Processed Forms of CTL Epitopes From MART-1 and gp100," *Int. J. Cancer*, 82(5), 669-677 (1999).
Stanislawski et al., "Circumventing tolerance to a human MDM2-derived tumor antigen by TCR gene transfer," *Nature Immunol.*, 2 (10), 962-970 (2001).
Sutmuller et al., "Adoptive T Cell Immunotherapy of Human Uveal Melanoma Targeting gp100," *J. Immunol.*, 165 (12), 7308-7315 (2000).
Thomas et al., "Playing the Game Together: Coexpression of a Single Chain T Cell Receptor and a T Cell Receptor Constant-Alpha Domain Triggers Tumor Reactivity," *Blood*, 108 (11), Abstract 3716 (2006).
Thompson et al., "Competition among peptides in melanoma vaccines for binding to MHC Molecules" *J. Immunother.*, 27(6), 425-431 (Nov.-Dec. 2004).
Voss et al., "Designing TCR for Cancer Immunotherapy," *Meth. Mol. Med.*, 109, 229-256 (2005).
Wadhwa et al., "Receptor Mediated Glycotargeting," *J. Drug Targeting*, 3, 111-127 (1995).
Weber et al., "Specific low-affinity recognition of major histocompatibility complex plus peptide by soluble T-cell receptor," *Nature*, 356, 793-796 (1992).
Willemsen et al., "CD8α Coreceptor to Improve TCR Gene Transfer to Treat Melanoma: Down-Regulation of Tumor-Specific Production of IL-4,IL-5, and IL-10," *J. Immunology*, 177, 991-998 (2006).

(56) References Cited

OTHER PUBLICATIONS

Wucherpfenning et al., Abstract "the structural interactions between T cell receptors and MHC-peptide complexes place physical limits on self-nonself discrimination," *Cur. Top. Microbiol. Immunol*, 296, 19-37 (2005).

Yu et al., "Poor immunogenicity of a self-tumor antigen devices from peptide-MHC-1 instability and is independent of tolerance," *J. Clin. Invest.*, 114, 551-559 (2004).

* cited by examiner

FIG. 5A

Sp(0.01)A TCR α chain cDNA

```
  1 atgaaatcct tgagtgtttc cctagtggtc ctgtggctcc agttaaactg ggtgaacagc
 61 cagcagaagg tgcagcagag cccagaatcc ctcattgtcc cagagggagc catgacctct
121 ctcaactgca ctttcagcga cagtgcttct cagtattttg catggtacag acagcattct
181 gggaaagccc caaggcact gatgtccatc ttctccaatg gtgaaaaaga agaaggcaga
241 ttcacaattc acctcaataa agccagtctg catttctcgc tacacatcag agactcccag
301 cccagtgact ctgctctcta cctctgtgca gccataact atgcccaggg attaaccttc
361 ggtcttggca ccagagtatc tgtgtttccc tacatccaga acccagaacc tgctgtgtac
421 cagttaaaag atcctcggtc tcaggacagc accctctgcc tgttcaccga ctttgactcc
481 caaatcaatg tgccgaaaac catggaatct ggaacgttca tcactgacaa aactgtgctg
541 gacatgaaag ctatggattc caagagcaat ggggccattg cctggagcaa ccagacaagc
601 ttcacctgcc aagatatctt caaagagacc aacgccacct accccagttc agacgttccc
661 tgtgatgcca cgttgactga gaaaagcttt gaaacagata tgaacctaaa ctttcaaaac
721 ctgtcagtta tgggactccg aatcctcctg ctgaaagtag ccggatttaa cctgctcatg
781 acgctgaggc tgtggtccag ttga
```

Sp(0.01)A TCR α chain protein (translated from cDNA)

MKSLSVSLVVLWLQLNWVNSQQKVQQSPESLIVPEGAMTSLNCTFSDSASQYFAWYRQHSGKAPKALMSIFSNGEKEE
GRFTIHLNKASLHFSLHIRDSQPSDSALYLCAANNYAQGLTFGLGTRVSVFPYIQNPEPAVYQLKDPRSQDSTLCLFT
DFDSQINVPKTMESGTFITDKTVLDMKAMDSKSNGAIAWSNQTSFTCQDIFKETNATYPSSDVPCDATLTEKSFETDM
NLNFQNLSVMGLRILLLKVAGFNLLMTLRLWSS

FIG. 5B

Sp(0.01)A TCR β chain cDNA

```
  1 atgggctcca gactcttctt tgtggttttg attctcctgt gtgcaaaaca catggaggct
 61 gcagtcaccc aaagtccaag aagcaaggtg gcagtaacag gaggaaaggt gacattgagc
121 tgtcaccaga ctaataacca tgactatatg tactggtatc ggcaggacac ggggcatggg
181 ctgaggctga tccattactc atatgtcgct gacagcacgg agaaaggaga tatccctgat
241 gggtacaagg cctccagacc aagccaagag aatttctctc tcattctgga gttggcttcc
301 ctttctcaga cagctgtata tttctgtgcc agcagccctg ggggggggg ggaacagtac
361 ttcggtcccg gcaccaggct cacggtttta gaggatctga aaatgtgac tccacccaag
421 gtctccttgt tgagccatc aaaagcagag attgcaaaca acgaaaggc taccctcgtg
481 tgcttggcca ggggcttctt ccctgaccac gtggagctga gctggtgggt gaatggcaag
541 gaggtccaca gtggggtcag cacggaccct caggcctaca aggagagcaa ttatagctac
601 tgcctgagca gccgcctgag ggtctctgct accttctggc acaatcctcg aaaccacttc
661 cgctgccaag tgcagttcca tgggctttca gaggaggaca gtggccaga gggctcaccc
721 aaacctgtca cacagaacat cagtgcagag gcctggggcc gagcagactg tgggattacc
781 tcagcatcct atcaacaagg ggtcttgtct gccaccatcc tctatgagat cctgctaggg
841 aaagccaccc tgtatgctgt gcttgtcagt acactggtgg tgatggctat ggtcaaaaga
901 agaattcat ga
```

Sp(0.01)A TCR β chain protein (translated from cDNA)

MGSRLFFVVLILLCAKHMEAAVTQSPRSKVAVTGGKVTLSCHQTNNHDYMYWYRQDTGHGLRLIHYSYVADSTEKGDI
PDGYKASRPSQENFSLILELASLSQTAVYFCASSPGGGGEQYFGPGTRLTVLEDLRNVTPPKVSLFEPSKAEIANKRK
ATLVCLARGFFPDHVELSWWVNGKEVHSGVSTDPQAYKESNYSYCLSSRLRVSATFWHNPRNHFRCQVQFHGLSEEDK
WPEGSPKPVTQNISAEAWGRADCGITSASYQQGVLSATILYEILLGKATLYAVLVSTLVVMAMVKRKNS

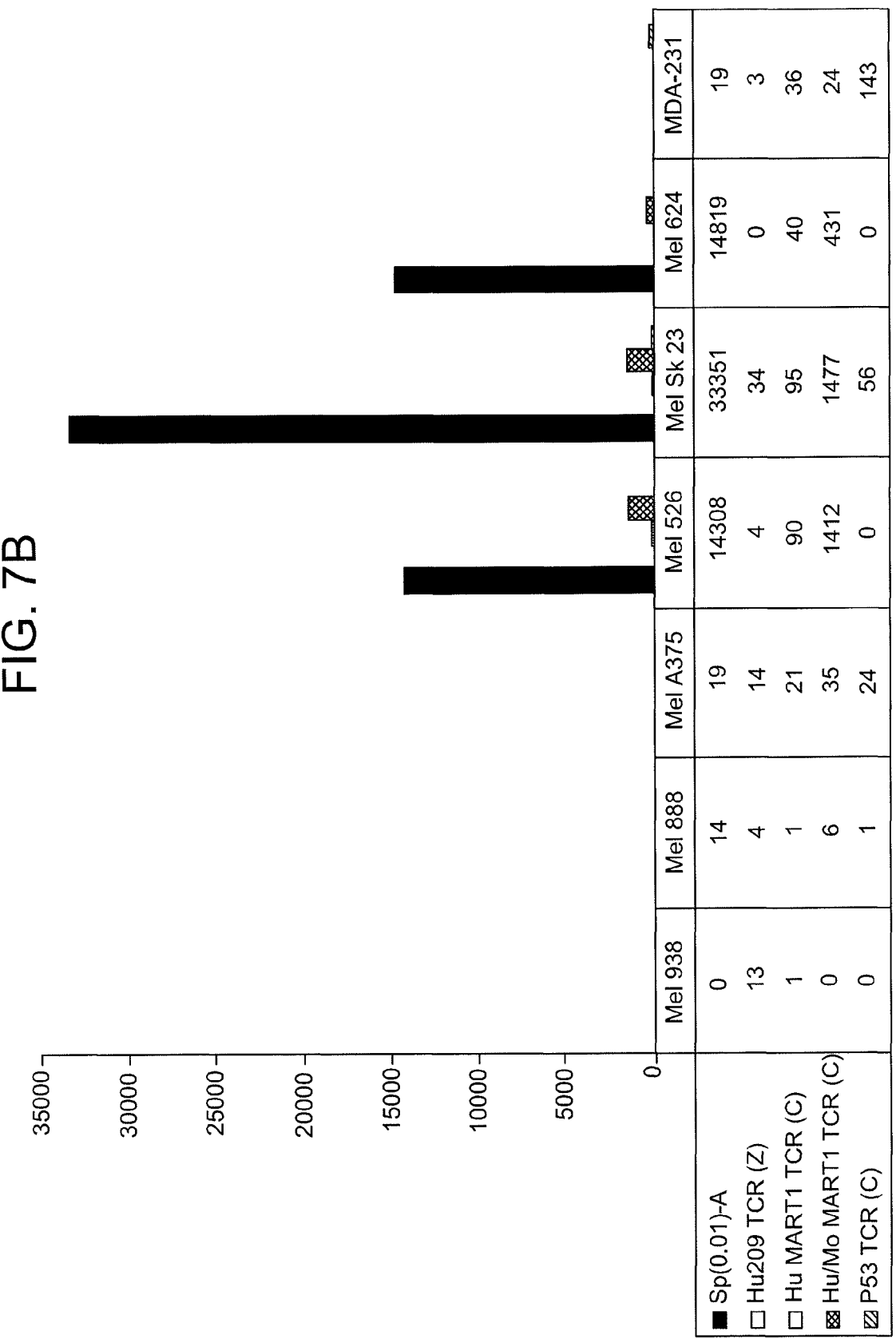

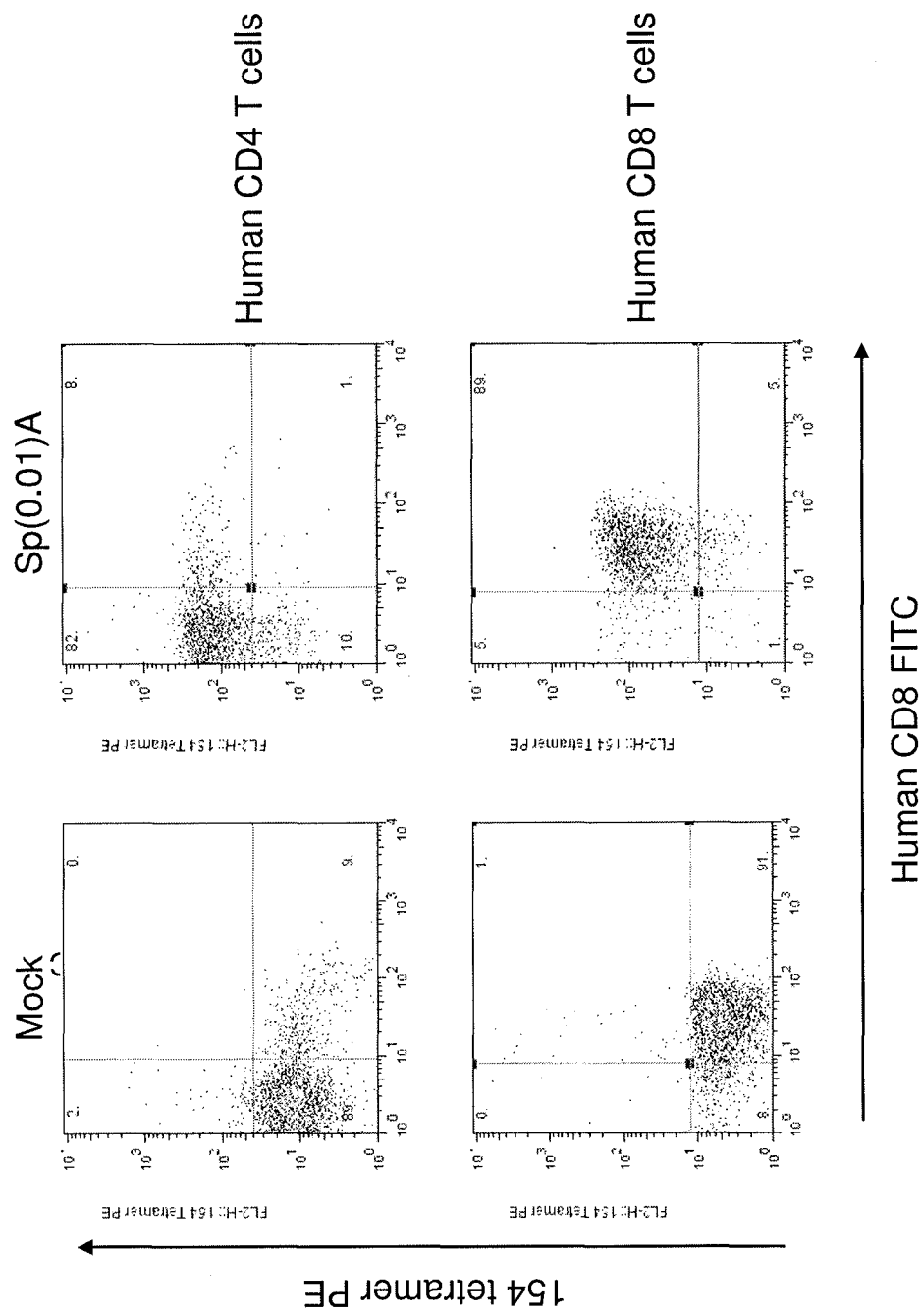

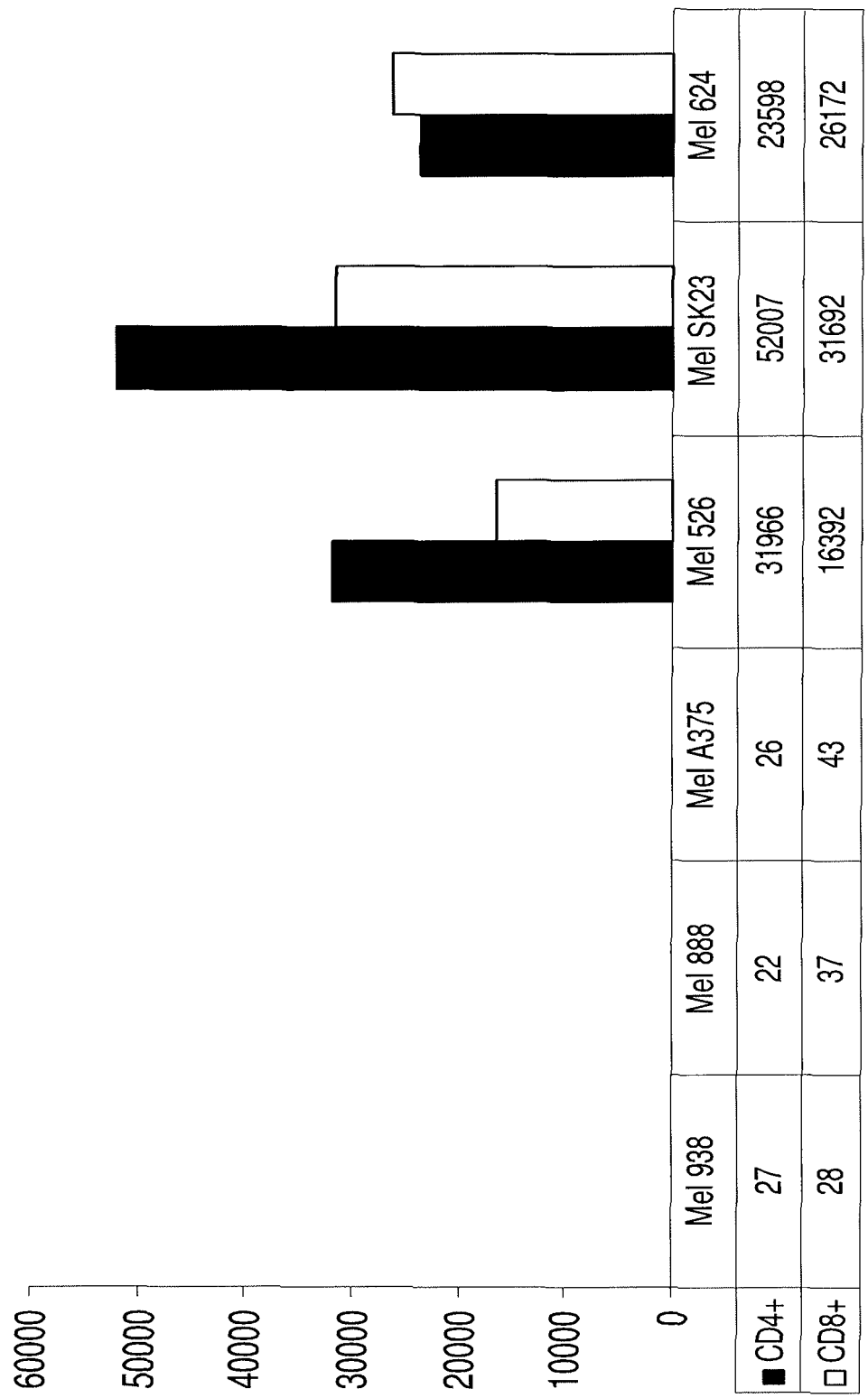

FIG. 9B
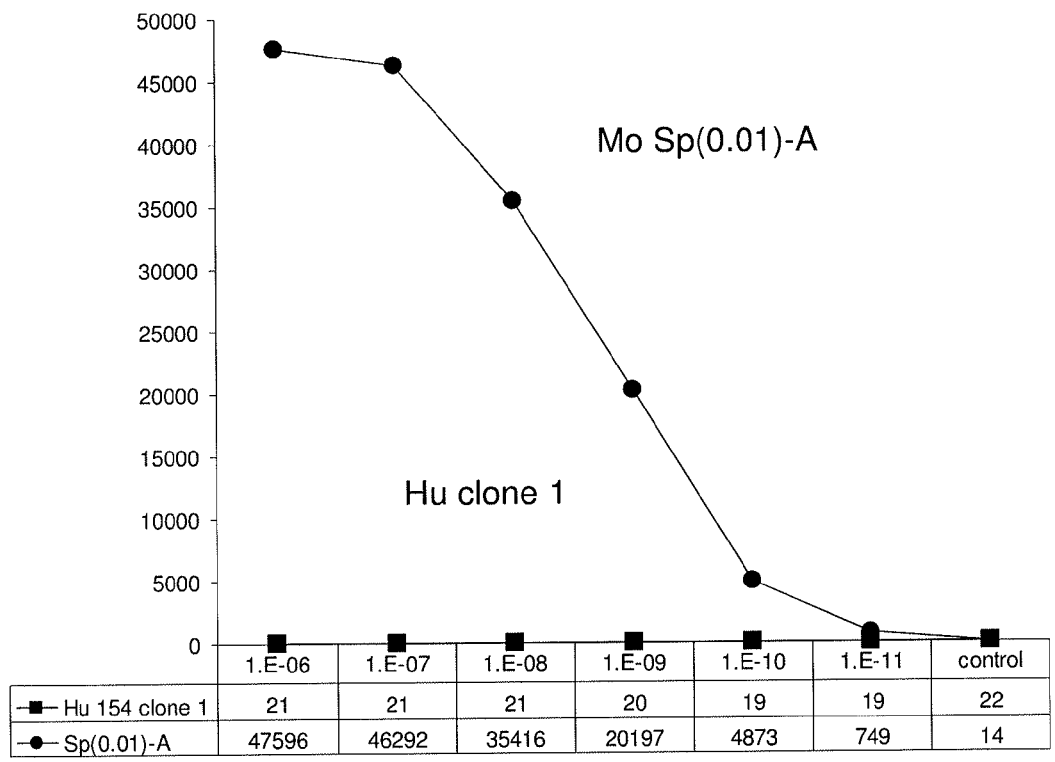
| | 1.E-06 | 1.E-07 | 1.E-08 | 1.E-09 | 1.E-10 | 1.E-11 | control |
|---|---|---|---|---|---|---|---|
| —■— Hu 154 clone 1 | 21 | 21 | 21 | 20 | 19 | 19 | 22 |
| —●— Sp(0.01)-A | 47596 | 46292 | 35416 | 20197 | 4873 | 749 | 14 |
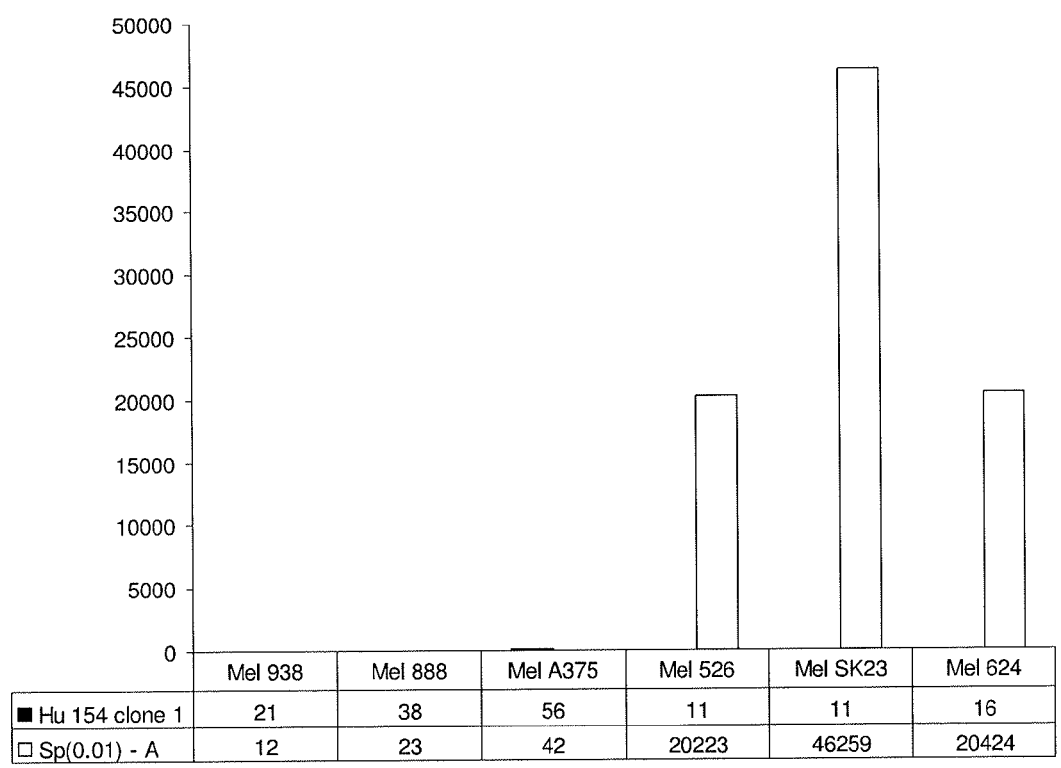
| | Mel 938 | Mel 888 | Mel A375 | Mel 526 | Mel SK23 | Mel 624 |
|---|---|---|---|---|---|---|
| ■ Hu 154 clone 1 | 21 | 38 | 56 | 11 | 11 | 16 |
| □ Sp(0.01) - A | 12 | 23 | 42 | 20223 | 46259 | 20424 |

FIG. 9C
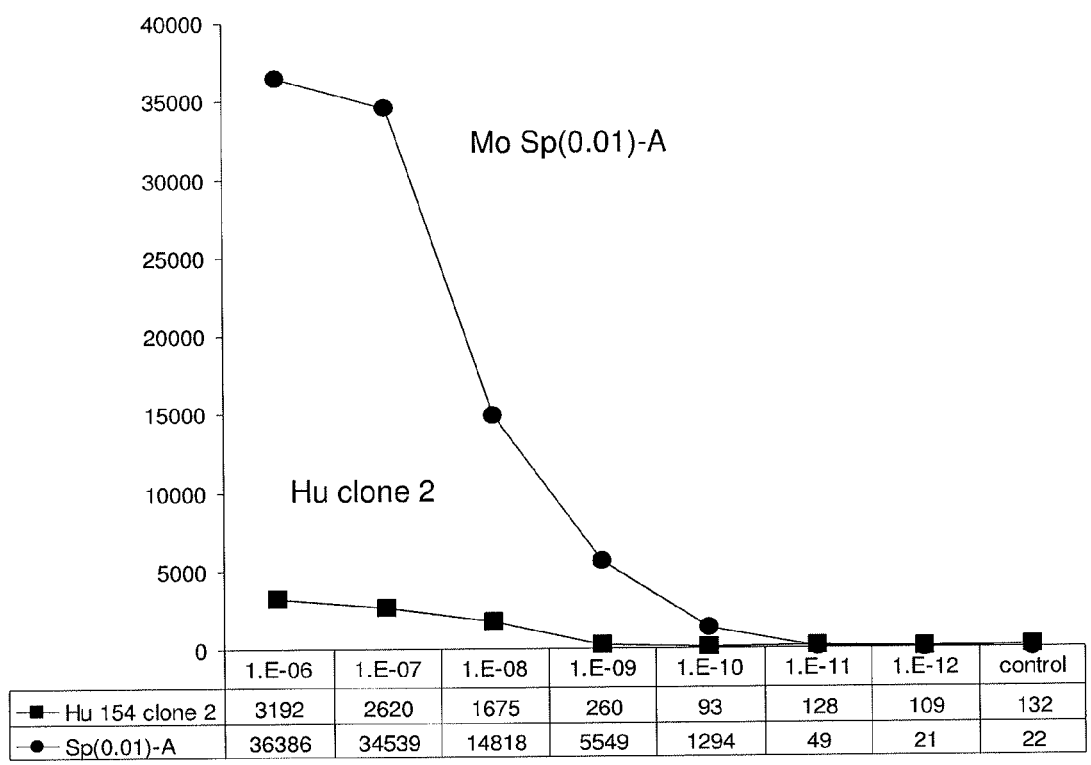
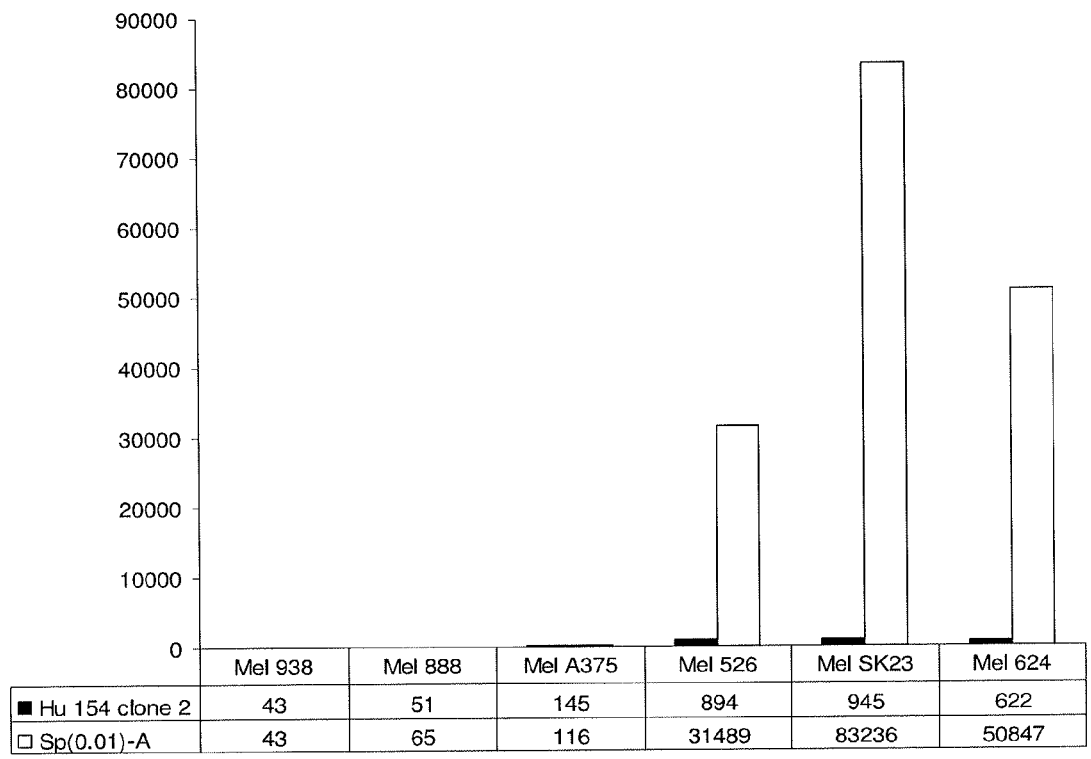

FIG. 10A

T2(1) B α chain

ATGATGAAGACATCCCTTCACACTGTATTCCTATTCTTGTGGCTATGGATGGACTGGGAGAGCCATGGAGA
GAAGGTCGAGCAACATGAGTCTACACTGAGTGTTCGAGAGGGAGACAGCGCTGTCATCAACTGCACTTACA
CAGATACTGCTTCATCATACTTCCCTTGGTACAAGCAAGAAGCTGGAAAGAGTCTCCACTTTGTGATAGAC
ATTCGTTCAAATGTGGACAGAAAACAGAGCCAAAGACTTATAGTTTTGTTGGATAAGAAAGCCAAACGATT
CTCCCTGCACATCACAGCCACACAGCCTGAAGATTCAGCCATCTACTTCTGTGCAGCAAGCTCGGATAGCA
ACTATCAGTTGATCTGGGGCTCTGGGACCAAGCTAATTATAAAGCCAGACATCCAGAACCCAGAACCTGCT
GTGTACCAGTTAAAAGATCCTCGGTCTCAGGACAGCACCCTCTGCCTGTTCACCGACTTTGACTCCCAAAT
CAATGTGCCGAAAACCATGGAATCTGGAACGTTCATCACTGACAAAACTGTGCTGGACATGAAAGCTATGG
ATTCCAAGAGCAATGGGGCCATTGCCTGGAGCAACCAGACAAGCTTCACCTGCCAAGATATCTTCAAAGAG
ACCAACGCCACCTACCCCAGTTCAGACGTTCCTGTGATGCCACGTTGACTGAGAAAAGCTTTGAAACAGA
TATGAACCTAAACTTTCAAAACCTGTCAGTTATGGGACTCCGAATCCTCCTGCTGAAAGTAGCCGGATTTA
ACCTGCTCATGACGCTGAGGCTGTGGTCCAGTTGA

T2(1) B β chain

ATGTCTAACACTGCCTTCCCTGACCCCGCCTGGAACACCACCCTGCTATCTTGGGTTGCTCTCTTTCTCCT
GGGAACAAGTTCAGCAAATTCTGGGGTTGTCCAGTCTCCAAGATACATAATCAAAGGAAAGGGAGAAAGGT
CCATTCTAAAATGTATTCCCATCTCTGGACATCTCTCTGTGGCCTGGTATCAACAGACTCAGGGGCAGGAA
CTAAAGTTCTTCATTCAGCATTATGATAAAATGGAGAGAGATAAAGGAAACCTGCCCAGCAGATTCTCAGT
CCAACAGTTTGATGACTATCACTCTGAGATGAACATGAGTGCCTTGGAGCTAGAGGACTCTGCCGTGTACT
TCTGTGCCAGCTCTCTTTCTGGGGCGAACTATGCTGAGCAGTTCTTCGGACCAGGGACACGACTCACCGTC
CTAGAGGATCTGAGAAATGTGACTCCACCCAAGGTCTCCTTGTTTGAGCCATCAAAAGCAGAGATTGCAAA
CAAACAAAAGGCTACCCTCGTGTGCTTGGCCAGGGGCTTCTTCCCTGACCACGTGGAGCTGAGCTGGTGGG
TGAATGGCAAGGAGGTCCACAGTGGGGTCAGCACGGACCCTCAGGCCTACAAGGAGAGCAATTATAGCTAC
TGCCTGAGCAGCCGCCTGAGGGTCTCTGCTACCTTCTGGCACAATCCTCGAAACCACTTCCGCTGCCAAGT
GCAGTTCCATGGGCTTTCAGAGGAGGACAAGTGGCCAGAGGGCTCACCCAAACCTGTCACACAGAACATCA
GTGCAGAGGCCTGGGGCCGAGCAGACTGTGGGATTACCTCAGCATCCTATCAACAAGGGGTCTTGTCTGCC
ACCATCCTCTATGAGATCCTGCTAGGGAAAGCCACCCTGTATGCTGTGCTTGTCAGTACACTGGTGGTGAT
GGCTATGGTCAAAAGAAAGAATTCATGA

FIG. 10B

Sp(0.1)A10 α chain

```
ATGCTCCTGGCGCTCCTCCCAGTGCTGGGGATACACTTTGTCCTGAGAGATGCCCAAGCTCAGTCAGTGAC
ACAGCCCGATGCTCGCGTCACTGTCTCTGAAGGAGCCTCTCTGCAGCTGAGATGCAAGTATTCCTACTCTG
CGACACCTTATCTGTTCTGGTATGTCCAGTACCCGCGGCAGGGCTGCAGCTGCTCCTCAAGTACTATTCA
GGAGACCCAGTGGTTCAAGGAGTGAACAGCTTCGAGGCTGAGTTCAGCAAGAGTAACTCTTCCTTCCACCT
GCAGAAAGCCTCTGTGCACTGGAGCGACTCGGCTGTGTACTTCTGTGCTCTGAGCCACGATAGCAACTATC
AGTTGATCTGGGGCTCTGGGACCAAGCTAATTATAAAGCCAGACATCCAGAACCCAGAACCTGCTGTGTAC
CAGTTAAAAGATCCTCGGTCTCAGGACAGCACCCTCTGCCTGTTCACCGACTTTGACTCCCAAATCAATGT
GCCGAAAACCATGGAATCTGGAACGTTCATCACTGACAAAACTGTGCTGGACATGAAAGCTATGGATTCCA
AGAGCAATGGGGCCATTGCCTGGAGCAACCAGACAAGCTTCACCTGCCAAGATATCTTCAAAGAGACCAAC
GCCACCTACCCCAGTTCAGACGTTCCCTGTGATGCCACGTTGACTGAGAAAAGCTTTGAAACAGATATGAA
CCTAAACTTTCAAAACCTGTCAGTTATGGGACTCCGAATCCTCCTGCTGAAAGTAGCCGGATTTAACCTGC
TCATGACGCTGAGGCTGTGGTCCAGTTGA
```

Sp(0.1)A10 β chain

```
ATGTCTAACACTGCCTTCCCTGACCCCGCCTGGAACACCACCCTGCTATCTTGGGTTGCTCTCTTTCTCCT
GGGAACAAGTTCAGCAAATTCTGGGGTTGTCCAGTCTCCAAGATACATAATCAAAGGAAAGGGAGAAAGGT
CCATTCTAAAATGTATTCCCATCTCTGGATATCTCTCTGTGGCCTGGTATCAACAGACTCAGGGGCAGGAA
CTAAAGTTCTTCATTCAGCATTATGATAAAATGGAGAGAGATAAAGGAAACCTGCCCAGCAGATTCTCAGT
CCAACAGTTTGATGACTATCACTCTGAGATGAACATGAGTGCCTTGGAGCTAGAGGACTCTGCCGTGTACT
TCTGTGCCAGCTCTCTCGCGGGGGTTAACTATGCTGAGCAGTTCTTCGGACCAGGGACACGACTCACCGTC
CTAGAGGATCTGAGAAATGTGACTCCACCCAAGGTCTCCTTGTTTGAGCCATCAAAAGCAGAGATTGCAAA
CAAACAAAAGGCTACCCTCGTGTGCTTGGCCAGGGGCTTCTTCCCTGACCACGTGGAGCTGAGCTGGTGGG
TGAATGGCAAGGAGGTCCACAGTGGGGTCAGCACGGACCCTCAGGCCTACAAGGAGAGCAATTATAGCTAC
TGCCTGAGCAGCCGCCTGAGGGTCTCTGCTACCTTCTGGCACAATCCTCGAAACCACTTCCGCTGCCAAGT
GCAGTTCCATGGGCTTTCAGAGGAGGACAAGTGGCCAGAGGGCTCACCCAAACCTGTCACACAGAACATCA
GTGCAGAGGCCTGGGGCCGAGCAGACTGTGGGATTACCTCAGCATCCTATCAACAAGGGGTCTTGTCTGCC
ACCATCCTCTATGAGATCCTGCTAGGGAAAGCCACCCTGTATGCTGTGCTTGTCAGTACACTGGTGGTGAT
GGCTATGGTCAAAAGAAAGAATTCATGA
```

FIG. 10C

T2(1) C α chain

ATGATGAAGACATCCCTTCACACTGTATTCCTATTCTTGTGGCTATGGATGGACTGGGAGAGCCATGGAGA
GAAGGTCGAGCAACATGAGTCTACACTGAGTGTTCGAGAGGGAGACAGCGCTGTCATCAACTGCACTTACA
CAGATACTGCTTCATCATACTTCCCTTGGTACAAGCAAGAAGCTGGAAAGAGTCTCCACTTTGTGATAGAC
ATTCGTTCAAATGTGGACAGAAAACAGAGCCAAAGACTTATAGTTTTGTTGGATAAGAAAGCCAAACGATT
CTCCCTGCACATCACAGCCACACAGCCTGAAGATTCAGCCATCTACTTCTGTGCAGCAAGCTCGGATAGCA
ACTATCAGTTGATCTGGGGCTCTGGGACCAAGCTAATTATAAAGCCAGACATCCAGAACCCAGAACCTGCT
GTGTACCAGTTAAAAGATCCTCGGTCTCAGGACAGCACCCTCTGCCTGTTCACCGACTTTGACTCCCAAAT
CAATGTGCCGAAAACCATGGAATCTGGAACGTTCATCACTGACAAAACTGTGCTGGACATGAAAGCTATGG
ATTCCAAGAGCAATGGGGCCATTGCCTGGAGCAACCAGACAAGCTTCACCTGCCAAGATATCTTCAAAGAG
ACCAACGCCACCTACCCCAGTTCAGACGTTCCCTGTGATGCCACGTTGACTGAGAAAAGCTTTGAAACAGA
TATGAACCTAAACTTTCAAAACCTGTCAGTTATGGGACTCCGAATCCTCCTGCTGAAAGTAGCCGGATTTA
ACCTGCTCATGACGCTGAGGCTGTGGTCCAGTTGA

T2(1)C α chain

ATGTCTAACACTGCCTTCCCTGACCCCGCCTGGAACACCACCCTGCTATCTTGGGTTGCTCTCTTTCTCCT
GGGAACAAGTTCAGCAAATTCTGGGGTTGTCCAGTCTCCAAGATACATAATCAAAGGAAAGGGAAAAAGGT
CCATTCTAAAATGTATTCCCATCTCTGGACATCTCTCTGTGGCCTGGTATCAACAGACTCAGGGGCAGGAA
CTAAAGTTCTTCATTCAGCATTATGATAAAATGGAGAGAGATAAAGGAAACCTGCCCAGCAGATTCTCAGT
CCAACAGTTTGATGACTATCACTCTGAGATGAACATGAGTGCCTTGGAGCTAGAGGACTCTGCCGTGTACT
TCTGTGCCAGCTCTCTTTCTGGGGCGAACTATGCTGAGCAGTTCTTCGGACCAGGGACACGACTCACCGTC
CTAGAGGATCTGAGAAATGTGACTCCACCCAAGGTCTCCTTGTTTGAGCCATCAAAAGCAGAGATTGCAAA
CAAACGAAAGGCTACCCTCGTGTGCTTGGCCAGGGGCTTCTTCCCTGACCACGTGGAGCTGAGCTGGTGGG
TGAATGGCAAGGAGGTCCACAGTGGGGTCAGCACGGACCCTCAGGCCTACAAGGAGAGCAATTATAGCTAC
TGCCTGAGCAGCTGCCTGAGGGTCTCTGCTACCTTCTGGCACAATCCTCGAAACCACTTCCGCTGCCAAGT
GCAGTTCCATGGGCTTTCAGAGGAGGACAAGTGGCCAGAGGGCTCACCCAAACCTGTCACACAGGACATCA
GTGCAGAGGCCTGGGCCGAGCAGACTGTGGGATTACCTCAGCATCCTATCAACAAGGGTCTTGTCTGCC
ACCATCCTCTACGAGATCCTGCTAGGGAAAGCCACCCTGTATGCTGTGCTTGTCAGTACACTGGTGGTGAT
GGCTATGGTCAAAAGAAAGAATTCATGA

FIG. 13

```
5' LTR, 6126-6639
Alpha chain, 3-806
IRES, 807-1438
Beta chain, 1439-2350
3' LTR, 2439-2953
```

```
   1 ccatgtcatc cttgagtgtt tccctagtgg tcctgtggct ccagttaaac tgggtgaaca
  61 gccagcagaa ggtgcagcag agcccagaat ccctcattgt cccagaggga gccatgacct
 121 ctctcaactg cactttcagc gacagtgctt ctcagtattt tgcatggtac agacagcatt
 181 ctgggaaagc ccccaaggca ctgatgtcca tcttctccaa tggtgaaaaa gaagaaggca
 241 gattcacaat tcacctcaat aaagccagtc tgcatttctc gctacacatc agagactccc
 301 agcccagtga ctctgctctc tacctctgtg cagccaataa ctatgcccag ggattaacct
 361 tcggtcttgg caccagagta tctgtgtttc cctacatcca gaacccagaa cctgctgtgt
 421 accagttaaa agatcctcgg tctcaggaca gcaccctctg cctgttcacc gactttgact
 481 cccaaatcaa tgtgccgaaa accatggaat ctggaacgtt catcactgac aaaactgtgc
 541 tggacatgaa agctatggat tccaagagca atgggccat tgcctggagc aaccagacaa
 601 gcttcacctg ccaagatatc ttcaaagaga ccaacgccac ctaccccagt tcagacgttc
 661 cctgtgatgc cacgttgact gagaaaagct ttgaaacaga tatgaaccta aactttcaaa
 721 acctgtcagt tatgggactc cgaatcctcc tgctgaaagt agccggattt aacctgctca
 781 tgacgctgag gctgtggtcc agttgagcgg ccgctctaga actagtggat ctccacgtgg
 841 cggctagtac tccggtattg cggtacccTT gtacgcctgt tttatactcc cttcccgtaa
 901 cttagacgca caaaaccaag ttcaatagaa gggggtacaa accagtacca ccacgaacaa
 961 gcacttctgt ttccccggtg atgtcgtata gactgcttgc gtggttgaaa gcgacggatc
1021 cgttatccgc ttatgtactt cgagaagccc agtaccacct cggaatcttc gatgcgttgc
1081 gctcagcact caaccccaga gtgtagctta ggctgatgag tctggacatc cctcaccggt
1141 gacggtggtc caggctgcgt tggcggccta cctatggcta acgccatggg acgctagttg
1201 tgaacaaggt gtgaagagcc tattgagcta cataagaatc ctccggcccc tgaatgcggc
1261 taatcccaac ctcggagcag gtggtcacaa accagtgatt ggcctgtcgt aacgcgcaag
1321 tccgtggcgg aaccgactac tttgggtgtc cgtgtttcct tttatttat tgtggctgct
1381 tatggtgaca atcacagatt gttatcataa agcgaattgg ataggatcaa gcttatcgat
1441 gggctccaga ctcttctttg tggttttgat tctcctgtgt gcaaaacaca tggaggctgc
1501 agtcacccaa agtccaagaa gcaaggtggc agtaacagga ggaaaggtga cattgagctg
1561 tcaccagact aataaccatg actatatgta ctggtatcgg caggacacgg ggcatgggct
1621 gaggctgatc cattactcat atgtcgctga cagcacggag aaaggagata tccctgatgg
1681 gtacaaggcc tccagaccaa gccaagagaa tttctctctc attctggagt tggcttccct
1741 ttctcagaca gctgtatatt tctgtgccag cagccctggg ggggggggg aacagtactt
1801 cggtcccggc accaggctca cggttttaga ggatctgaga aatgtgactc cacccaaggt
1861 ctccttgttt gagccatcaa aagcagagat tgcaaacaaa cgaaaggcta ccctcgtgtg
1921 cttggccagg gcttcttcc ctgaccacgt ggagctgagc tggtgggtga atggcaagga
1981 ggtccacagt ggggtcagca cggaccctca ggcctacaag gagagcaatt atagctactg
2041 cctgagcagc cgcctgaggg tctctgctac cttctggcac aatcctcgaa accacttccg
2101 ctgccaagtg cagttccatg gcttttcaga ggaggacaag tggccagagg ctcacccaa
2161 acctgtcaca cagaacatca gtgcagaggc ctggggccga gcagactgtg ggattacctc
2221 agcatcctat caacaagggg tcttgtctgc caccatcctc tatgagatcc tgctagggaa
2281 agccaccctg tatgctgtgc ttgtcagtac actggtggtg atggctatgg tcaaaagaaa
2341 gaattcatga taagcttcga attctgcagt cgacggtacc gcgggcccgg gatccgataa
2401 aataaaagat tttatttagt ctccagaaaa agggggggaat gaaagacccc acctgtaggt
2461 ttggcaagct agcttaagta acgccatttt gcaaggcatg gaaaatacat aactgagaat
2521 agagaagttc agatcaaggt taggaacaga gagacagcag aatatgggcc aaacaggata
2581 tctgtggtaa gcagttcctg ccccggctca ggccaagaa cagatggtcc ccagatgcgg
2641 tcccgccctc agcagtttct agagaaccat cagatgtttc cagggtgccc caaggacctg
2701 aaaatgaccc tgtgccttat tgaactaac caatcagttc gcttctcgct tctgttcgcg
2761 cgcttctgct ccccgagctc aataaaagag cccacaaccc ctcactcggc gcgccagtcc
2821 tccgatagac tgcgtcgccc gggtacccgt gtatccaata aaccctcttg cagttgcatc
2881 cgacttgtgg tctcgctgtt ccttgggagg gtctcctctg agtgattgac tacccgtcag
2941 cggggggtctt tcatgggtaa cagtttcttg aagttggaga acaacattct gagggtagga
3001 gtcgaatatt aagtaatcct gactcaatta gccactgttt tgaatccaca tactccaata
3061 ctcctgaaat ccatcgatgg agttcattat ggacagcgca gaaagagctg gggagaattg
3121 tgaaattgtt atccgctcac aattccacac aacatacgag ccggaagcat aaagtgtaaa
```

FIG. 13 cont.

```
3181 gcctggggtg cctaatgagt gagctaactc acattaattg cgttgcgctc actgcccgct
3241 ttccagtcgg gaaacctgtc gtgccagctg cattaatgaa tcggccaacg cgcggggaga
3301 ggcggtttgc gtattgggcg ctcttccgct tcctcgctca ctgactcgct gcgctcggtc
3361 gttcggctgc ggcgagcggt atcagctcac tcaaaggcgg taatacggtt atccacagaa
3421 tcaggggata acgcaggaaa gaacatgtga gcaaaaggcc agcaaaaggc caggaaccgt
3481 aaaaaggccg cgttgctggc gttttccat aggctccgcc ccctgacga gcatcacaaa
3541 aatcgacgct caagtcagag gtggcgaaac ccgacaggac tataaagata ccaggcgttt
3601 ccccctggaa gctccctcgt gcgctctcct gttccgaccc tgccgcttac cggatacctg
3661 tccgcctttc tcccttcggg aagcgtggcg ctttctcata gctcacgctg taggtatctc
3721 agttcggtgt aggtcgttcg ctccaagctg ggctgtgtgc acgaaccccc cgttcagccc
3781 gaccgctgcg ccttatccgg taactatcgt cttgagtcca acccggtaag acacgactta
3841 tcgccactgg cagcagccac tggtaacagg attagcagag cgaggtatgt aggcggtgct
3901 acagagttct tgaagtggtg gcctaactac ggctacacta aaggacagt atttggtatc
3961 tgcgctctgc tgaagccagt taccttcgga aaaagagttg gtagctcttg atccggcaaa
4021 caaaccaccg ctggtagcgg tggtttttttt gtttgcaagc agcagattac gcgcagaaaa
4081 aaaggatctc aagaagatcc tttgatcttt tctacggggt ctgacgctca gtggaacgaa
4141 aactcacgtt aagggatttt ggtcatgaga ttatcaaaaa ggatcttcac ctagatcctt
4201 ttaaattaaa aatgaagttt taaatcaatc taaagtatat atgagtaaac ttggtctgac
4261 agttaccaat gcttaatcag tgaggcacct atctcagcga tctgtctatt tcgttcatcc
4321 atagttgcct gactccccgt cgtgtagata actacgatac gggagggctt accatctggc
4381 cccagtgctg caatgatacc gcgagaccca cgctcaccgg ctccagattt atcagcaata
4441 aaccagccag ccggaagggc cgagcgcaga agtggtcctg caactttatc cgcctccatc
4501 cagtctatta attgttgccg ggaagctaga gtaagtagtt cgccagttaa tagtttgcgc
4561 aacgttgttg ccattgctac aggcatcgtg gtgtcacgct cgtcgtttgg tatggcttca
4621 ttcagctccg gttcccaacg atcaaggcga gttacatgat cccccatgtt gtgcaaaaaa
4681 gcggttagct ccttcggtcc tccgatcgtt gtcagaagta agttggccgc agtgttatca
4741 ctcatggtta tggcagcact gcataattct cttactgtca tgccatccgt aagatgcttt
4801 tctgtgactg gtgagtactc aaccaagtca ttctgagaat agtgtatgcg gcgaccgagt
4861 tgctcttgcc cggcgtcaat acgggataat accgcgccac atagcagaac tttaaaagtg
4921 ctcatcattg gaaaacgttc ttcggggcga aaactctcaa ggatcttacc gctgttgaga
4981 tccagttcga tgtaacccac tcgtgcaccc aactgatctt cagcatcttt tactttcacc
5041 agcgtttctg ggtgagcaaa aacaggaagg caaaatgccg caaaaaaggg aataagggcg
5101 acacggaaat gttgaatact catactcttc ctttttcaat attattgaag catttatcag
5161 ggttattgtc tcatgagcgg atacatattt gaatgtattt agaaaaataa acaaataggg
5221 gttccgcgca catttccccg aaaagtgcca cctgacgtct aagaaaccat tattatcatg
5281 acattaacct ataaaaatag gcgtatcacg aggccctttc gtctcgcgcg tttcggtgat
5341 gacggtgaaa acctctgaca catgcagctc ccggagacgg tcacagcttg tctgtaagcg
5401 gatgccggga gcagacaagc ccgtcagggc gcgtcagcgg gtgttggcgg gtgtcggggc
5461 tggcttaact atgcggcatc agagcagatt gtactgagag tgcaccatat gcggtgtgaa
5521 ataccgcaca gatgcgtaag gagaaaatac cgcatcaggc gccattcgcc attcaggctg
5581 cgcaactgtt gggaagggcg atcggtgcgg gcctcttcgc tattacgcca gctggcgaaa
5641 gggggatgtg ctgcaaggcg attaagttgg gtaacgccag ggttttccca gtcacgacgt
5701 tgtaaaacga cggccagtgc cacgctctcc cttatgcgac tcctgcatta ggaagcagcc
5761 cagtagtagg ttgaggccgt tgagcaccgc cgccgcaagg aatggtgcat gcaaggagat
5821 ggcgcccaac agtcccccgg ccacggggcc tgccaccata cccacgccga acaagcgct
5881 catgagcccg aagtggcgag cccgatcttc ccatcggtg atgtcggcga tataggcgcc
5941 agcaaccgca cctgtggcgc cggtgatgcc ggccacgatg cgtccggcgt agaggcgatt
6001 taaagacagg atatcagtgg tccaggctct agttttgact caacaatatc accagctgaa
6061 gcctatagag tacgagccat agataaaata aagatttta tttagtctcc agaaaaaggg
6121 gggaatgaaa gaccccacct gtaggtttgg caagctagct taagtaacgc cattttgcaa
6181 ggcatggaaa atacataact gagaatagag aagttcagat caaggttagg aacagagaga
6241 cagcagaata tgggccaaac aggatatctg tggtaagcag ttcctgcccc ggctcagggc
6301 caagaacaga tggtccccag atgcggtccc gccctcagca gtttctagag aaccatcaga
6361 tgtttccagg gtgccccaag gacctgaaaa tgaccctgtg ccttatttga actaaccaat
6421 cagttcgctt ctcgcttctg ttcgcgcgct tctgctcccc gagctcaata aaagagccca
6481 caaccctca ctcggcgcgc cagtcctccg atagactgcg tcgcccgggt accgtattc
6541 ccaataaagc ctcttgctgt ttgcatccga atcgtggact cgctgatcct tgggagggtc
6601 tcctcagatt gattgactgc ccacctcggg gtctttcat ttggaggttc accgagatt
6661 tggagacccc tgcctaggga ccaccgaccc cccgccgggg aggtaagctg gccagcggtc
6721 gtttcgtgtc tgtctctgtc tttgtgcgtg tttgtgccgg catctaatgt ttgcgcctgc
6781 gtctgtacta gttagctaac tagctctgta tctggcggac ccgtggtgga actgacgagt
```

FIG. 13 cont.

```
6841 tcggaacacc cggccgcaac cctgggagac gtcccaggga cttcggggc cgtttttgtg
6901 gcccgacctg agtccaaaaa tcccgatcgt tttggactct ttggtgcacc ccccttagag
6961 gagggatatg tggttctggt aggagacgag aacctaaaac agttcccgcc tccgtctgaa
7021 tttttgcttt cggtttggga ccgaagccgc gccgcgcgtc ttgtctgctg cagcatcgtt
7081 ctgtgttgtc tctgtctgac tgtgtttctg tatttgtctg agaatatggg cccgggctag
7141 cctgttacca ctcccttaag tttgacctta ggtcactgga aagatgtcga gcggatcgct
7201 cacaaccagt cggtagatgt caagaagaga cgttgggtta ccttctgctc tgcagaatgg
7261 ccaacccttta acgtcggatg gccgcgagac ggcacccttta accgagacct catcacccag
7321 gttaagatca aggtctttc acctggcccg catggacacc cagaccaggt ccccctacatc
7381 gtgacctggg aagccttggc ttttgacccc cctccctggg tcaagccctt tgtacaccct
7441 aagcctccgc ctcctcttcc tccatccgcc ccgtctctcc cccttgaacc tcctcgttcg
7501 accccgcctc gatcctccct ttatccagcc ctcactcctt ctctaggcgc cnnnncatat
7561 gagatcttat atggggcacc ccgcccctt gtaaacttcc ctgaccctga catgacaaga
7621 gttactaaca gccctctct ccaagctcac ttacaggctc tctacttagt ccagcacgaa
7681 gtctggagac ctctggcgcc agcctaccaa gaacaactgg accgaccggt ggtacctcac
7741 ccttaccgag tcggcgacac agtgtgggtc cgccgacacc agactaagaa cctagaacct
7801 cgctggaaag gaccttacac agtcctgctg accaccccca ccgccctcaa agtagacggc
7861 atcgcagctt ggatacacgc cgcccacgtg aaggctgccg accccggggg tggaccatcc
7921 tctagaccg (SEQ ID NO: 57)
```

GP100-SPECIFIC T CELL RECEPTORS AND RELATED MATERIALS AND METHODS OF USE

This patent application is a continuation of U.S. patent application Ser. No. 13/483,286, filed May 30, 2012, now U.S. Pat. No. 8,613,932, which is a divisional of U.S. patent application Ser. No. 12/522,321, filed Aug. 10, 2009, now U.S. Pat. No. 8,216,565, which is a U.S. National Phase of International Patent Application No. PCT/US08/50841, filed Jan. 11, 2008, which claims the benefit of U.S. Provisional Patent application No. 60/884,732, filed Jan. 12, 2007, and U.S. Provisional Patent Application No. 60/885,724, filed Jan. 19, 2007, which are each incorporated by reference in its entirety herein.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 77,186 Byte ASCII (Text) file named "715775ST25.TXT," dated Dec. 12, 2013.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 78,000 Byte ASCII (Text) file named "702330ST25.TXT," created on Jan. 10, 2008.

BACKGROUND OF THE INVENTION

The gp100 protein has been demonstrated as an antigen in several human cancers, including glioblastoma and melanoma (Saikali et al., *J. Neurooncol.* 81(2): 139-148 (2007); and Cormier et al., *J. Immunother.* 21 (1): 27-31 (1991)). A peptide comprising amino acid residues 154-162 of the gp100 protein ($gp100_{154-162}$) is abundantly presented on the surface of tumors and also binds the MHC molecule HLA-A2 with relative high affinity (Skipper et al., *Int. J. Cancer* 82(5): 669-677 (1999); Parkhurst et al., *J. Immunol.* 157(6): 2539-2548. (1996)). Therefore, $gp100_{154-162}$ is an ideal tumor target antigen for cancer immunotherapy. T cells with specificity to this epitope, however, are difficult to obtain in HLA-A2-positive patients in amounts useful for therapeutic purposes.

In view of the foregoing, there is a need in the art for gp100-reactive T cells that can be obtained in therapeutic amounts for use in treating cancer patients. The invention provides such T cells and methods of treating cancer, especially melanoma.

BRIEF SUMMARY OF THE INVENTION

The invention provides human cells, particularly human T cells, comprising a murine T Cell Receptor (TCR) having antigenic specificity for the cancer antigen gp100.

The invention also provides an isolated or purified T cell receptor (TCR) having antigenic specificity for amino acids 154-162 of a gp100 protein (SEQ ID NO: 1). The TCR can comprise any of the specified amino acid sequences as described herein.

The invention also provides related polypeptides and proteins, as well as nucleic acids, recombinant expression vectors, host cells, and populations of cells. Further provided by the invention are antibodies, or an antigen binding portion thereof, conjugates, and pharmaceutical compositions relating to the TCRs of the invention.

Methods of detecting the presence of cancer in a host and methods of treating or preventing cancer in a host are further provided by the invention. The inventive method of detecting the presence of cancer in a host comprises (i) contacting a sample comprising cells of the cancer with any of the inventive human cells, TCRs, polypeptides, proteins, nucleic acids, recombinant expression vectors, host cells, populations of cells, or antibodies, or antigen binding portions thereof, described herein, thereby forming a complex, and (ii) detecting the complex, wherein detection of the complex is indicative of the presence of cancer in the host.

The inventive method of treating or preventing cancer in a host comprises administering to the host any of the inventive pharmaceutical compositions described herein in an amount effective to treat or prevent cancer in the host.

BRIEF DESCRIPTION OF THE SEVERAL VIEWS OF THE DRAWING(S)

FIG. 1 is a graph of the amount of IFN-γ (pg/ml) secreted by T cells from bulk cultures of HLA-A2 transgenic mice immunized with $gp100_{154-162}$ peptide upon stimulation with (1) T2 cells pulsed with 0.001 (bar with diagonal lines), 0.01 (bar with vertical lines), 0.1 (criss-crossed bar), or 1 μM (checkered bar) $gp100_{154-162}$ peptide or 1 μM β-galactosidase (dotted bar), or (2) melanoma cells: Mel A375 cells ($HLA-A2^+/gp100^-$; white bar) or Mel 526 ($HLA-A2^+$/human $gp100^+$ black bar).

FIG. 2 is a set of flow cytometry graphs of T cells from bulk cultures of HLA-A2 transgenic mice immunized with $gp100_{154-162}$ peptide stained with (1) PE-linked $gp100_{154-162}$ tetramer and FITC-labeled anti-mouse CD8 antibodies (left box) or (2) PE-linked $gp100_{209-217}$ tetramer and FITC-labeled anti-mouse CD8 antibodies (middle box). $gp100_{209-217}$-specific human T cell clone were stained with PE-linked $gp100_{209-217}$ tetramer and FITC-labeled anti-human CD8 antibodies as a control (right box).

FIG. 3 is a graph of amount of IFN-γ (pg/ml) secreted by clone Sp(0.01)A upon stimulation with (1) T2 cells pulsed with a negative control peptide (T2+gp100(209-2M); white bar) or $gp100_{154-162}$ peptide (black bar) or (2) melanoma cells: $HLA-A2^+/gp100^+$ Mel 526 cells (criss-crossed bar) and with $gp100^-$ Mel A375 cells (MelA375).

FIG. 4 is a set of flow cytometry graphs of clone Sp(0.01)A upon staining with (1) PE-labeled $gp100_{154-162}$ tetramer at a 1:100 dilution and FITC-labeled anti-mouse CD8 antibodies (left box), (2) PE-labeled $gp100_{154-162}$ tetramer at a 1:1000 dilution and FITC-labeled anti-mouse CD8 antibodies (middle box), and (3) PE-labeled $gp100_{209-217}$ tetramer and FITC-labeled anti-mouse CD8 antibodies (right box).

FIG. 5A depicts the nucleotide (SEQ ID NO: 26) and amino acid (SEQ ID NO: 10) sequences of the alpha chain of the TCR of clone Sp(0.01)A.

FIG. 5B depicts the nucleotide (SEQ ID NO: 27) and amino acid (SEQ ID NO: 11) sequences of the beta chain of the TCR of clone Sp(0.01)A.

Figure 6:
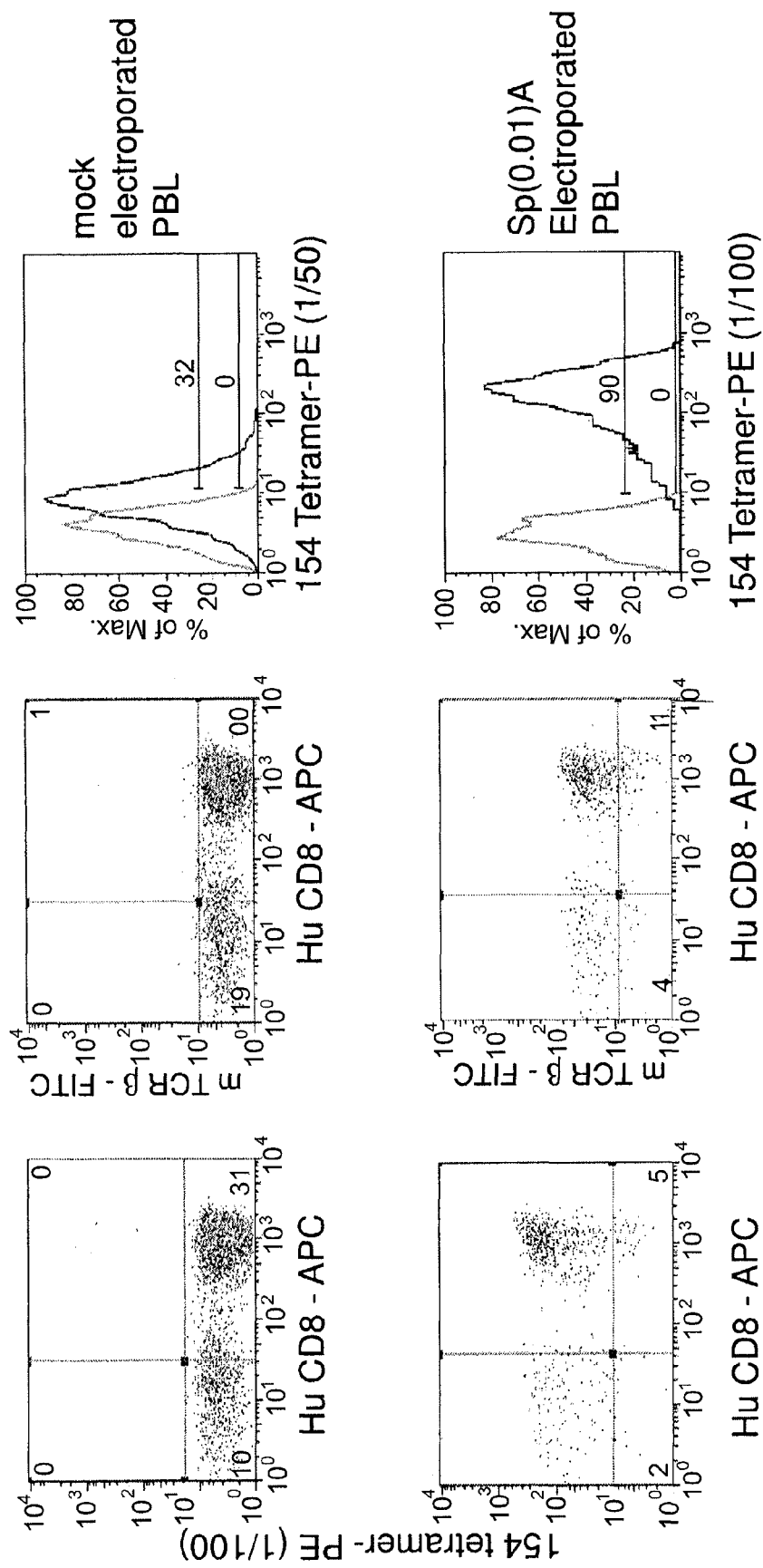

FIG. 6 are flow cytometry graphs of PBLs mock electroporated (top row) or electroporated with RNA encoding Sp(0.01)A TCR chains (bottom row) stained with (1) PE-labeled $gp100_{154-162}$ tetramer and APC-labeled anti-human CD8 antibodies (left boxes), (2) FITC-labeled mouse TCR beta chain antibodies and APC-labeled anti-human CD8 antibodies (middle boxes), and (3) PE-labeled gp100$_{154-162}$ tetramer at a 1:50 dilution or 1:100 dilution (right boxes).

Figure 7A:
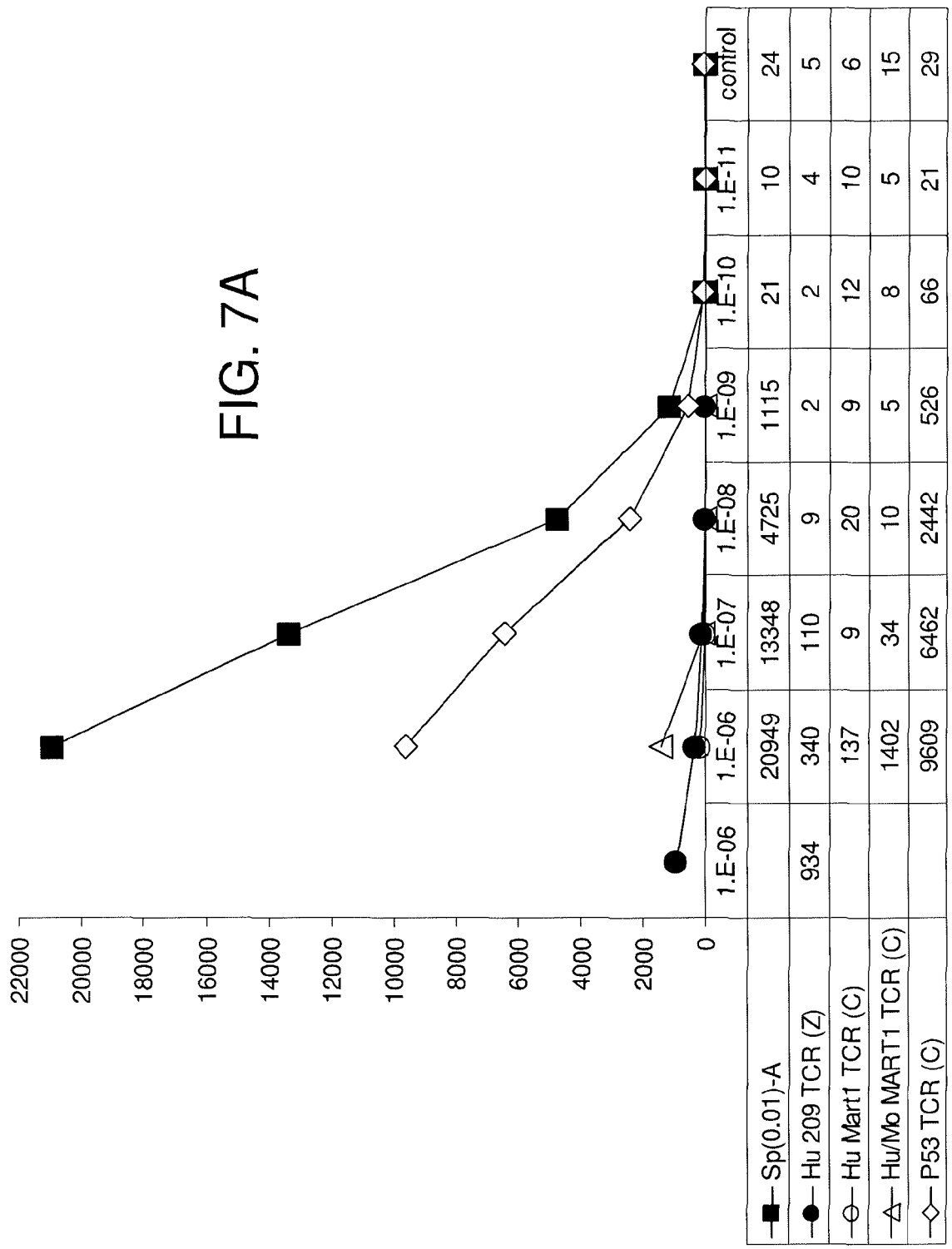

FIG. 7A is graph of the amount of IFN-γ produced by human PBLs electroporated with (1) Sp(0.01)A TCR RNA (closed squares), (2) human gp100$_{209-217}$ TCR RNA (closed circles), (3) human MART-1 TCR RNA (open circles), (4) human/mouse hybrid MART-1 TCR RNA (open triangles), and p53 TCR RNA (open diamonds), upon stimulation with T2 cells pulsed with $10^{-6}$, $10^{-7}$, $10^{-8}$, $10^{-9}$, $10^{-10}$, or $10^{-11}$ M gp100$_{154-162}$ peptide or $10^{-6}$ M negative control peptide.

FIG. 7B is a graph of the amount of IFN-γ produced by human PBLs electroporated with (1) Sp(0.01)A TCR RNA (black bars), (2) human gp100$_{209-217}$ TCR RNA (white bars), (3) human MART-1 TCR RNA (dotted bars), (4) human/mouse hybrid MART-1 TCR RNA (criss-crossed bars), and p53 TCR RNA (bars with diagonal lines), upon stimulation with melanoma cells (Mel 938 (HLA-A2$^-$/gp100$^+$/p53$^-$, MART-1$^+$), Mel 888 (HLA-A2$^-$/gp100$^+$/p53$^-$/MART-1$^+$), Mel A375 (HLA-A2$^+$/gp100$^-$/p53$^-$/gp100$^-$), Mel 526 (HLA-A2$^+$/gp100$^+$/p53$^+$/MART-1$^+$), Mel Sk 23 (HLA-A2$^+$/gp100$^-$/p53$^-$/MART-1$^+$), and Mel 624 (HLA-A2$^+$/gp100$^+$/p53$^+$/MART-1$^+$)) and breast carcinoma line MDA-231 (HLA-A2$^+$/gp100$^-$/p53$^+$/MART-1$^-$).

FIG. 8A are flow cytometry graphs of human CD4$^+$ T cells (top row) or human CD8$^+$ T cells (bottom row) mock electroporated (left column) or electroporated with Sp(0.01)A TCR RNA (right column) stained with PE-labeled gp100$_{154-162}$ tetramer and FITC-labeled anti-human CD8 antibodies.

Figure 8B:
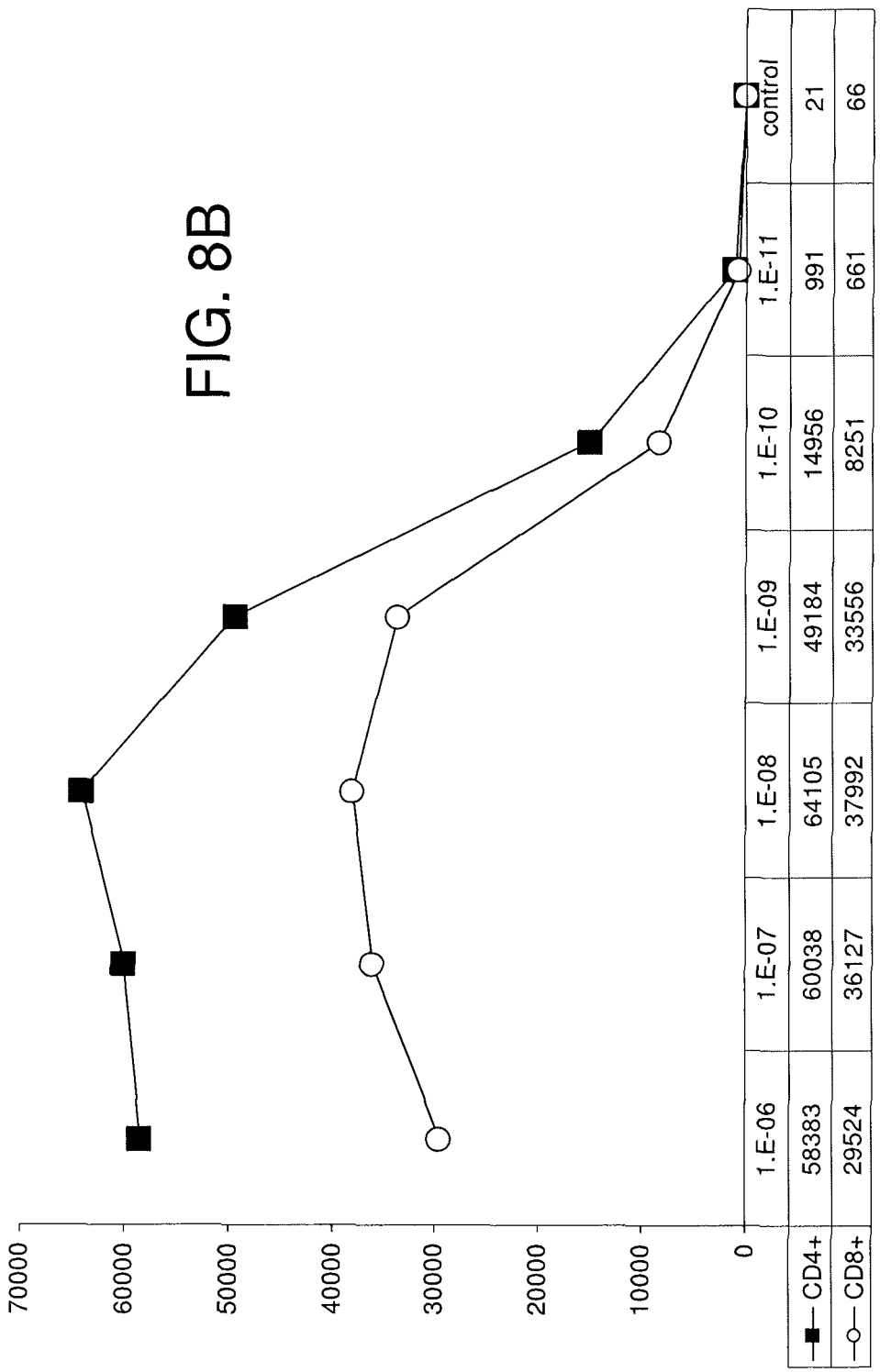

FIG. 8B is a graph of the IFN-γ produced by CD4$^+$ T cells (closed squares) or CD8$^+$ T cells (open circles) electroporated with Sp(0.01)A TCR RNA upon stimulation with T2 cells pulsed with $10^{-6}$, $10^{-7}$, $10^{-8}$, $10^{-9}$, $10^{-10}$, or $10^{-11}$ M gp100$_{154-162}$ peptide or $10^{-6}$ M negative control peptide.

FIG. 8C is a graph of the IFN-γ produced by CD4$^+$ T cells (black bars) or CD8$^+$ T cells (white bars) electroporated with Sp(0.01)A TCR RNA upon stimulation with melanoma cells: Mel 938, Mel 888, Mel A375, Mel 526, Mel Sk 23, and Mel 624.

Figure 9A:
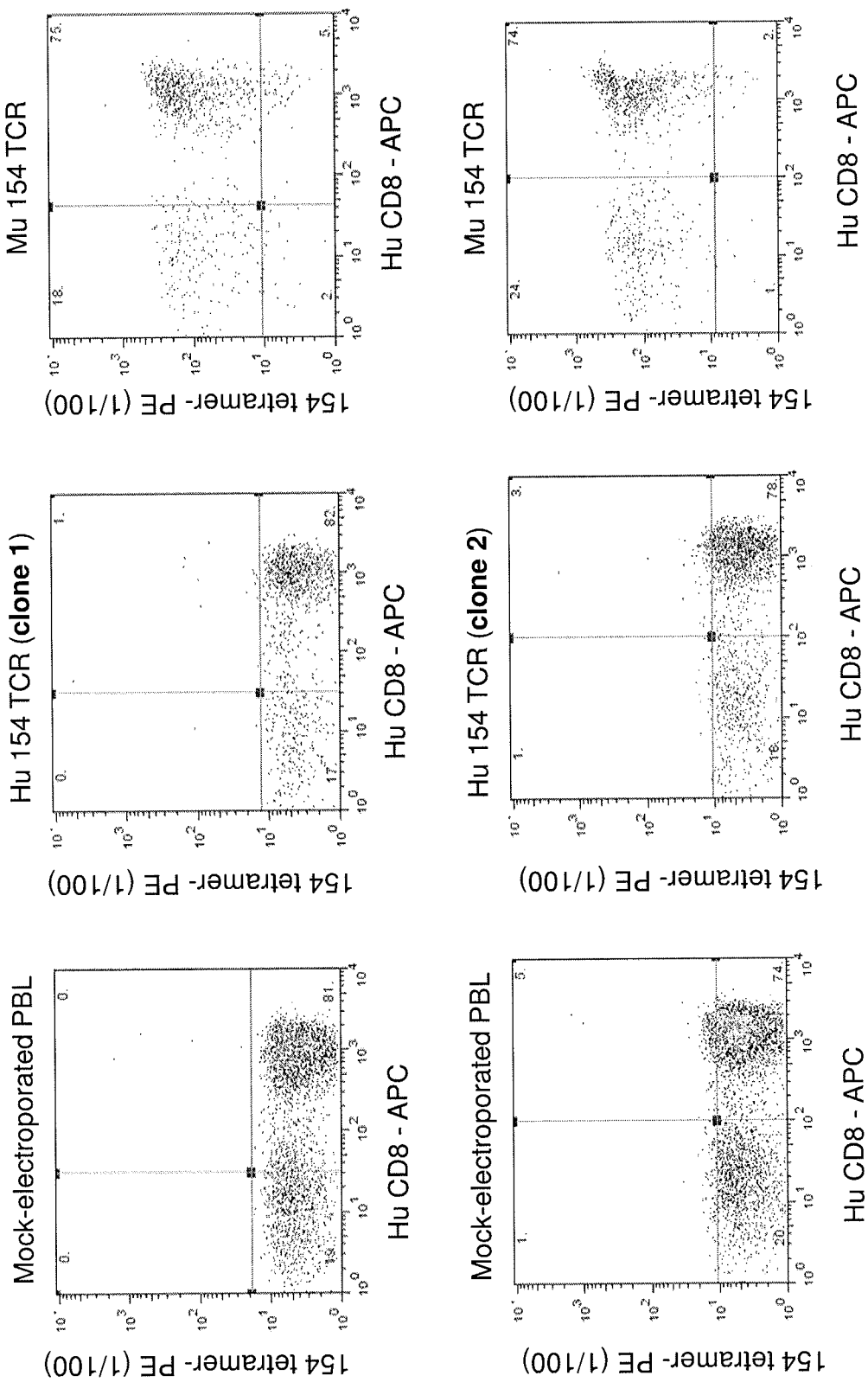

FIG. 9A are flow cytometry graphs of human PBLs mock electroporated (left column), electroporated with RNA encoding human gp100$^{154-162}$ TCR from clone 1 (upper middle box) or from clone 2 (lower middle box) or electroporated with RNA encoding Sp(0.01)A mouse TCR (right column) and stained with PE-labeled gp100$_{154-162}$ tetramer and APC-labeled anti-human CD8 antibodies.

FIG. 9B is a graph of the IFN-γ produced by human PBLs electroporated with RNA encoding a human gp100-specific TCR (from clone 1; closed squares in top graph and black bars in bottom graph) or encoding the mouse gp100-specific TCR (from clone Sp(0.01)A; closed circles in top graph and white bars in bottom graph) upon stimulation with T2 cells pulsed with $10^{-6}$, $10^{-7}$, $10^{-8}$, $10^{-9}$, $10^{-10}$, or $10^{-11}$ M gp100$_{154-162}$ peptide or negative control peptide (top graph) or with melanoma cells: Mel 938, Mel 888, Mel A375, Mel 526, Mel Sk 23, and Mel 624 (bottom graph).

FIG. 9C is a graph of the IFN-γ produced by human PBLs electroporated with RNA encoding a human gp100-specific TCR (from clone 2; closed squares in top graph and black bars in bottom graph) or encoding the mouse gp100-specific TCR (from clone Sp(0.01)A; closed circles in top graph and white bars in bottom graph) upon stimulation with T2 cells pulsed with $10^{-6}$, $10^{-7}$, $10^{-8}$, $10^{-9}$, $10^{-10}$, $10^{-11}$, or $10^{-12}$ M gp100$_{154-162}$ peptide or negative control peptide (top graph) or with melanoma cells: Mel 938, Mel 888, Mel A375, Mel 526 (HLA-A2$^+$/gp100$^+$, Mel Sk 23, and Mel 624 (bottom graph).

FIG. 10A depicts the nucleotide sequences encoding the gp100-specific TCR alpha (SEQ ID NO: 28) and beta (SEQ ID NO: 29) chains from clone T2(1)B.

FIG. 10B depicts the nucleotide sequences encoding the gp100-specific TCR alpha (SEQ ID NO: 30) and beta (SEQ ID NO: 31) chains from clone Sp(0.1)A10.

FIG. 10C depicts the nucleotide sequences encoding the gp100-specific TCR alpha (SEQ ID NO: 32) and beta (SEQ ID NO: 33) chains from clone T2(1)C.

Figure 11B:
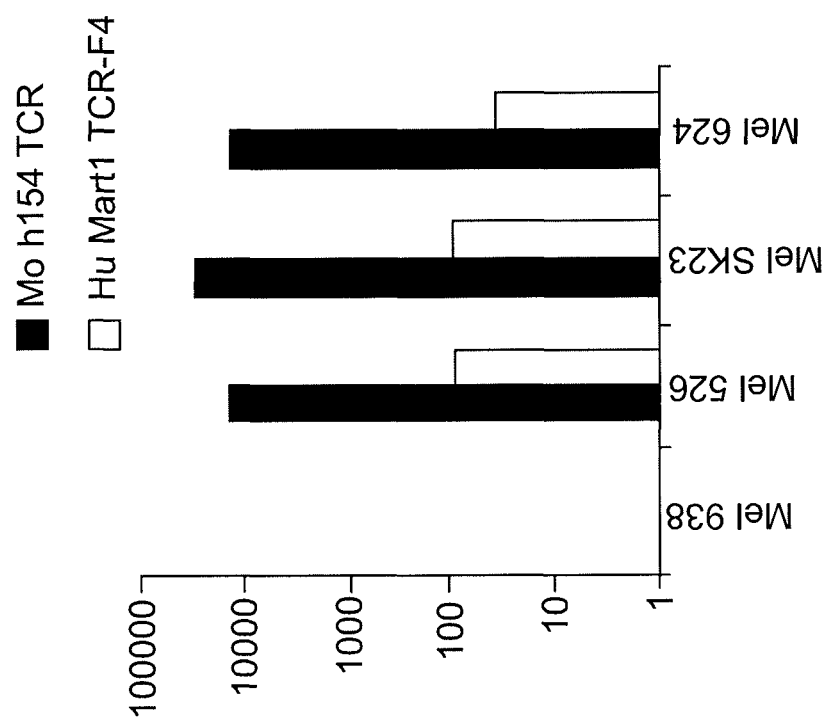
Figure 11A:
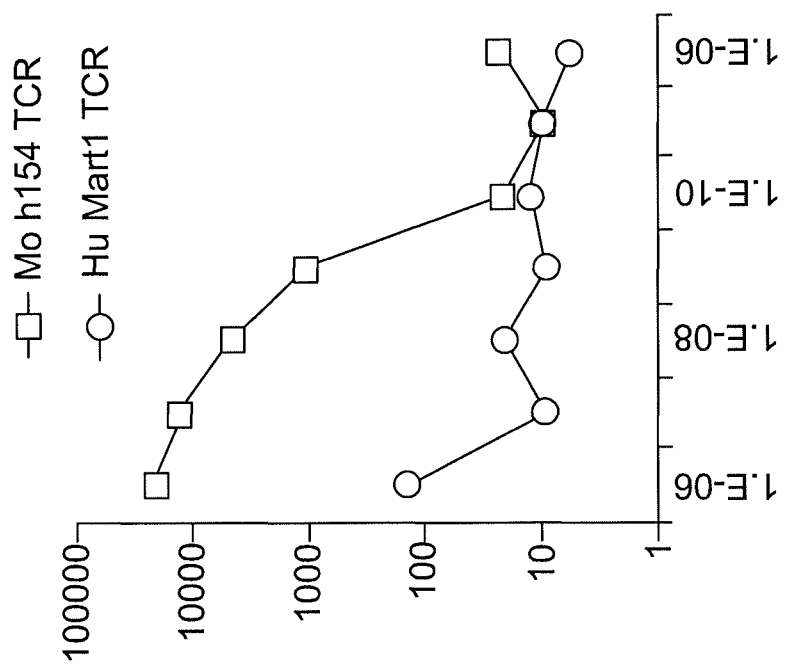

FIG. 11A and FIG. 11B depict the relative activities of a mouse gp100:154-162 specific TCR and a human MART-1 specific (F4) TCR. FIG. 11A depicts the IFN-γ (pg/ml) released by cells expressing the mouse gp100:154-162 specific TCR (black squares) or the human MART-1 specific (F4) TCR (white circles) in response to relevant peptide pulsed cells (gp100:154-162 peptide or MART-1 peptide). FIG. 11B depicts the IFN-γ (pg/ml) released by cells expressing the mouse gp100:154-162 specific TCR (black bars) or the human MART-1 specific (F4) TCR (white bars) in response to HLA-A2+ tumor cells (Mel 526, Mel SK23, Mel 624) or HLA-A2− tumor cells (Mel 938).

Figure 12:
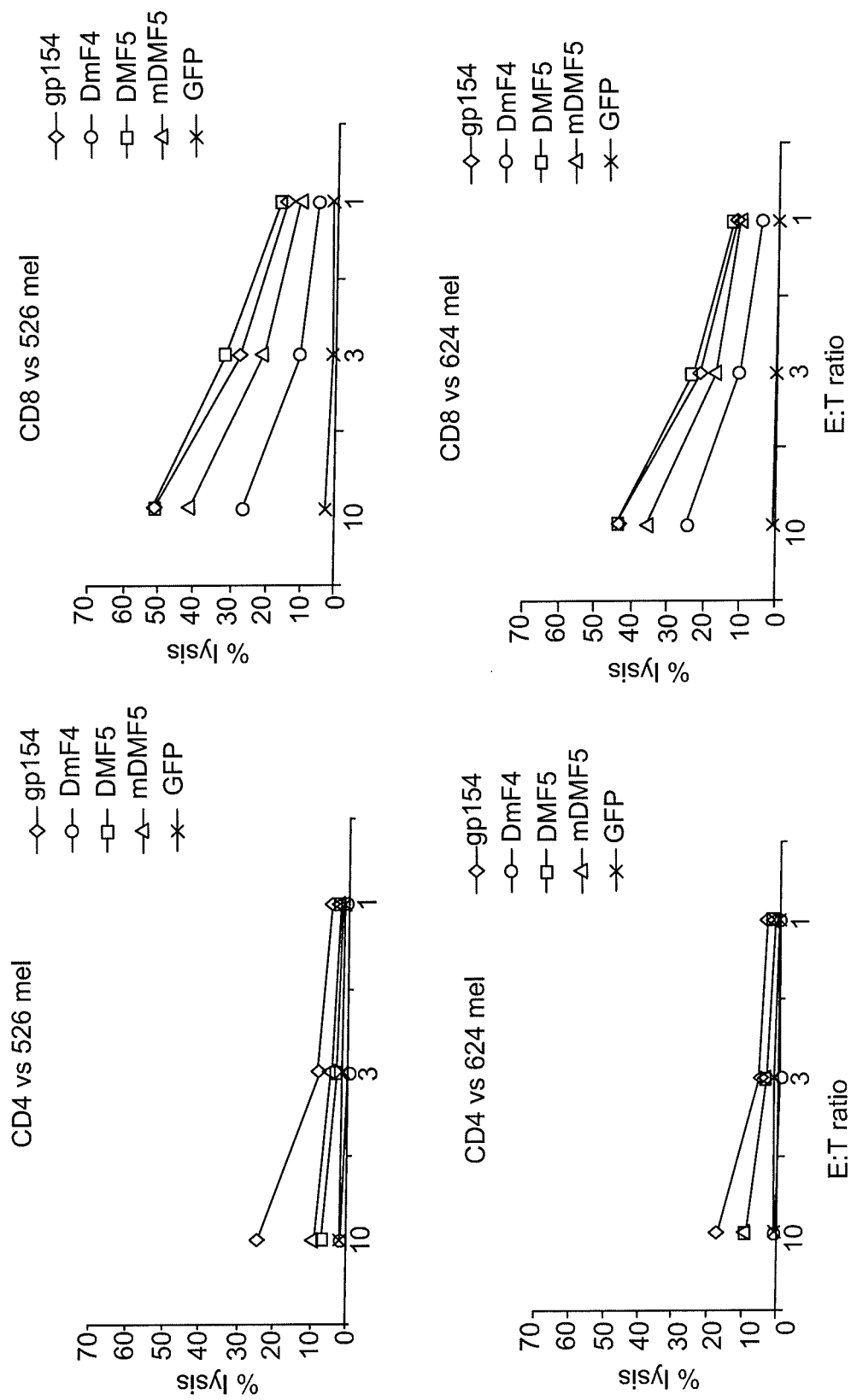

FIG. 12 depicts the percent lysis of target tumor cells by CD4+ PBL (left panels) or CD8+ PBL (right panels) retrovirally transduced with gp100:154-162 TCR (diamonds), DMF4 TCR (circles), DMF5 (squares), mDMF5 (triangles), or with control (GFP designated by "X"). The target tumor cells were 526 mel (top panels) or 624 mel (bottom panels).

FIG. 13 depicts the nucleotide sequence (SEQ ID NO: 57) of anti-gp100 TCR vector MSGV1-154-AIB.

Figure 14:
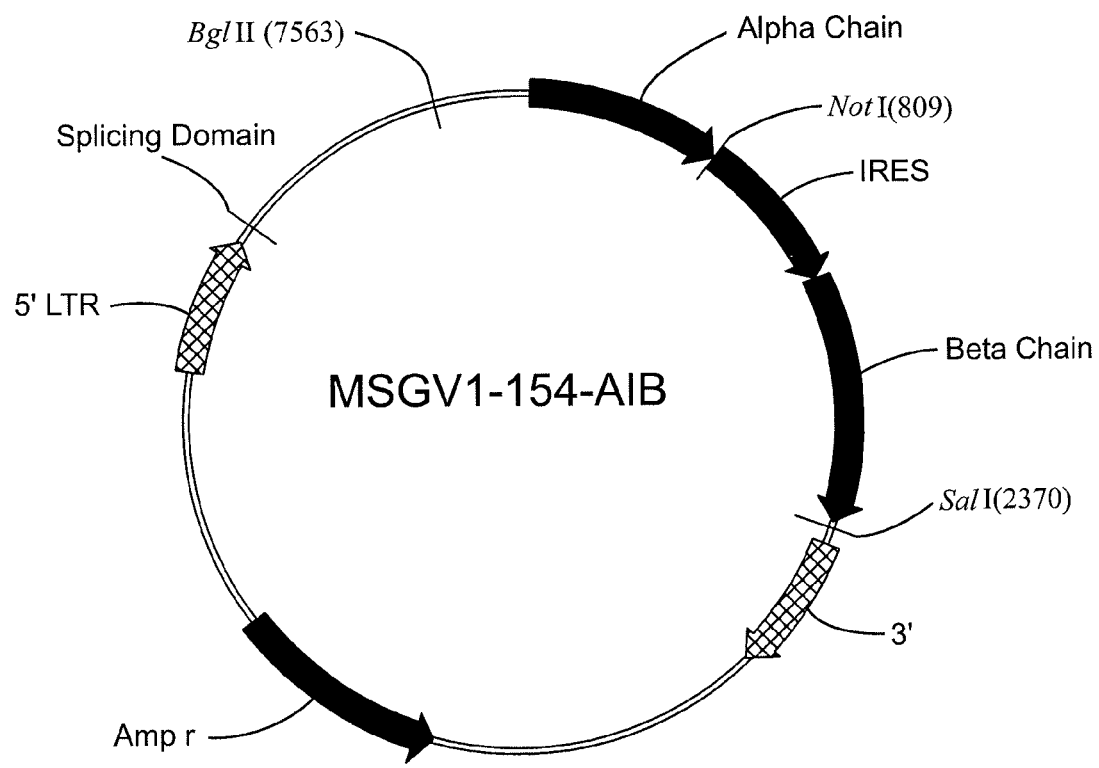

FIG. 14 depicts the map of plasmid DNA for vector MSGV1-154-AIB.

DETAILED DESCRIPTION OF THE INVENTION

The invention provides a human cell comprising a murine TCR having antigenic specificity for gp100. The human cell can be any cell originating from a human. For instance, the human cell of the invention can be a primary cell directly obtained from a human. Alternatively, the human cell can be a cell of a cultured human cell line. Also, the inventive human cell can be a cell originating from any human tissue. For instance, the human cell can be a blood cell (e.g., red blood cell, white blood cell, lymphocyte, etc.), an epithelial cell, an endothelial cell, muscle cell, hepatocyte, brain cells, renal cell, and the like. Preferably, the human cell is a blood cell. More preferably, the human cell is a lymphocyte. Most preferably, the lymphocyte is a T lymphocyte (i.e., T cell).

For purposes herein, the T cell can be any T cell, such as a cultured T cell, e.g., a primary T cell, or a T cell from a cultured T cell line, e.g., Jurkat, SupT1, etc., or a T cell obtained from a human. If obtained from a human, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), peripheral blood mononuclear cells (PBMCs), peripheral blood leukocytes (PBLs), tumor infiltrating cells (TILs), memory T cells, naïve T cells, and the like. Preferably, the T cell is a CD8$^+$ T cell or a CD4$^+$ T cell.

The human cell of the invention comprises a murine TCR through means of, e.g., recombinant technology. As used herein, the term "murine TCR" means a TCR that is derived from a mouse, i.e., a TCR that originated from or was, at one time, expressed by a mouse T cell. Desirably, the murine TCR is expressed on the surface of the human cell.

The murine TCR of the invention has antigenic specificity for the gp100 protein, e.g., human gp100. gp100, also known in the art as SILV, SI, SIL, ME20, PMEL17, or D12S53E, is a protein known to play an important role in regulating mammalian pigmentation (Hoashi et al., *J. Biol. Chem.* 280: 14006-14016 (e-publication on Jan. 28, 2005)) and is known as a cancer antigen expressed by human tumors, including melanoma and colorectal tumors (Tartaglia et al. (2001), supra). The amino acid and nucleotide sequences of human gp100 are published in the GenBank database of the National Center for Biotechnology Information (NCBI) as GenBank Accession No. NP_008859 (amino acid sequence) and GenBank Accession No. NM_006928.3 (nucleotide sequence). The amino acid sequence of a human gp100 is set forth herein as SEQ ID NO: 1.

As used herein, the phrase "having antigenic specificity," or like phrase, means that the TCR can specifically bind to and immunologically recognize gp100, or an epitope thereof, such that binding of the TCR to gp100, or the epitope thereof, elicits an immune response.

In a preferred embodiment of the invention, the murine TCR has antigenic specificity for amino acids 154-162 of a human gp100 of SEQ ID NO: 1, namely KTWGQYWQV (SEQ ID NO: 34). In this regard, the invention also provides an isolated or purified TCR having antigenic specificity for amino acids 154-162 of a gp100 protein (SEQ ID NO: 1).

The TCR of the invention (including the murine TCR of the inventive human cells) generally comprises two polypeptides (i.e., polypeptide chains), such as an α chain of a TCR, a β chain of a TCR, a γ chain of a TCR, a δ chain of a TCR, or a combination thereof. Such polypeptide chains of TCRs are known in the art. The polypeptides of the inventive TCR can comprise any amino acid sequence, provided that the TCR has antigenic specificity for gp100, e.g., amino acids 154-162 of a human gp100 of SEQ ID NO: 1.

In a preferred embodiment of the invention, the TCR comprises two polypeptide chains, each of which comprises a variable region, comprising an amino acid sequence selected from the group consisting of SEQ ID NOs: 2 to 9. In a more preferred embodiment, the TCR comprises (i) a first polypeptide chain comprising SEQ ID NO: 2 and a second polypeptide chain comprising SEQ ID NO: 3, (ii) a first polypeptide chain comprising SEQ ID NO: 4 and a second polypeptide chain comprising SEQ ID NO: 5, (iii) a first polypeptide chain comprising SEQ ID NO: 6 and a second polypeptide chain comprising SEQ ID NO: 7, or (iv) a first polypeptide chain comprising SEQ ID NO: 8 and a second polypeptide chain comprising SEQ ID NO: 9.

In a most preferred embodiment of the invention, the TCR comprises a first polypeptide chain comprising SEQ ID NO: 2 and a second polypeptide chain comprising SEQ ID NO: 3.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of any of SEQ ID NOs: 2, 4, 6, and 8. In this regard, the inventive TCR can comprise the amino acid sequence of any of SEQ ID NOs: 10, 12, 14, and 16. An inventive TCR of this type can be paired with any β chain of a TCR. Preferably, the β chain of the inventive TCR comprises the variable region of any of SEQ ID NOs: 3, 5, 7, and 9. In this regard, the inventive TCR can comprise the amino acid sequence of any of SEQ ID NOs: 11, 13, 15, and 17.

In a preferred embodiment, the TCR comprises an α chain comprising SEQ ID NO: 10 and a β chain comprising SEQ ID NO: 11, an α chain comprising SEQ ID NO: 12 and a β chain comprising SEQ ID NO: 13, an α chain comprising SEQ ID NO: 14 and a β chain comprising SEQ ID NO: 15, or an α chain comprising SEQ ID NO: 16 and a β chain comprising SEQ ID NO: 17.

In a more preferred embodiment, the TCR comprises an α chain comprising SEQ ID NO: 10 and a β chain comprising SEQ ID NO: 11, which is the full length α and β chains of the T cell clone termed Sp(0.01)A.

The TCRs of the invention can comprise one or more portions of a human TCR, such that the TCR, when administered to a human, is not rejected by the immune system of the human (as in e.g., graft vs. host disease). The portion can be, for example, a variable region of a human TCR or a constant region of a human TCR. Desirably, the portion is a constant region of a human TCR. The constant region of a human can, for example, comprise the amino acid sequence set forth in SEQ ID NOs: 55 and 56 (constant regions of alpha and beta chains, respectively). In this regard, the invention provides a hybrid TCR comprising a human constant region and a murine variable region, wherein the TCR is specific for gp100$_{154-162}$. Alternatively, the portion can be a few amino acids of a human TCR, such that the TCR, which is mostly murine, is "humanized." Methods of making such hybrid TCRs are known in the art. See, for example, Cohen et al., *Cancer Res.* 66: 8878-8886 (2006).

The invention also provides an isolated or purified polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to amino acids 154-162 of gp100 (SEQ ID NO: 1). The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to gp100, or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to gp100, having the ability to detect cancer, treat or prevent cancer. More desirably, the additional amino acids enhance the biological activity, as compared to the biological activity of the parent TCR.

The polypeptide can comprise, for instance, a functional portion of the TCR, wherein the functional portion is the variable region of the inventive TCR. In this regard, the polypeptide can comprise the amino acid sequence of any of SEQ ID NOs: 2 to 9, or a combination thereof. For instance, the polypeptide can comprise the amino acid sequence of SEQ ID NO: 2 and SEQ ID NO: 3, SEQ ID NO: 4 and SEQ ID NO: 5, SEQ ID NO: 6 and SEQ ID NO: 7, or SEQ ID NO: 8 and SEQ ID NO: 9. Preferably, the inventive polypeptide comprises SEQ ID NO: 2 (the variable region of an α chain) or 3 (the variable region of a β chain), or both SEQ ID NOs: 2 and 3.

Alternatively or additionally, the inventive polypeptide can comprise the entire length of an α or β chain of one of the TCRs described herein. In this regard, the inventive polypeptide can comprise an amino acid sequence of any of SEQ ID NOs: 10 to 17. Alternatively, the polypeptide of the invention can comprise both chains of the TCRs described herein. For example, the inventive polypeptide can comprise both amino acid sequences of SEQ ID NOs: 10 and 11, SEQ ID NOs: 12 and 13, SEQ ID NOs: 14 and 15, or SEQ ID NOs: 16 and 17.

The invention further provides an isolated or purified protein comprising at least one of the polypeptides described herein. By "protein" is meant a molecule comprising one or more polypeptide chains.

The protein of the invention can comprise, for example, a first polypeptide chain comprising the amino acid sequence of SEQ ID NO: 10 and a second polypeptide chain comprising the amino acid sequence of SEQ ID NO: 11. In this instance, the protein of the invention can be a TCR. Alternatively, if, for example, the protein comprises a single polypeptide chain comprising SEQ ID NO: 2 and SEQ ID NO: 3, or SEQ ID NO:10 and SEQ ID NO: 11, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, a TCR co-receptor (e.g., CD3, CD4, CD8), an MHC molecule (e.g., HLA-A2), or a portion thereof, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In a preferred embodiment of the invention, the protein is a soluble protein, e.g., a soluble TCR. Soluble TCRs, as well as methods of making the same, are known in the art. See, for example, Jesson et al., *Internatl. Immunol.* 10: 27-35 (1998); Boulter et al., *Protein Engineering Design & Selection* 16: 707-711 (2003); Weber et al., *Nature* 356: 793-796 (1992); International Patent Application Publication No. WO 96/13593; and U.S. Pat. No. 6,080,840.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof.

The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to gp100 (e.g., gp100$_{154-162}$), to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 98% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

For instance, the invention provides a functional variant of the TCR, polypeptide, and protein comprising the amino acid sequence of SEQ ID NO: 5, 9, 13 or 17, wherein the functional variant comprises one, two, three, or four amino acid substitutions in SEQ ID NO: 5, 9, 13, or 17. Desirably, the functional variant comprises the amino acid sequence of SEQ ID NO: 52 or 53, wherein X is any amino acid. More desirably, the X at position 17 of SEQ ID NO: 52 or the X at position 46 of SEQ ID NO: 53 is a negatively charged amino acid.

Additionally, the invention provides a functional variant of the TCR, polypeptide, and protein comprising the amino acid sequence of SEQ ID NO: 11, wherein the functional variant comprises one or two amino acid substitutions in SEQ ID NO: 11. Desirably, the functional variant comprises the amino acid sequence of SEQ ID NO: 54, wherein X is any amino acid.

The TCR, polypeptide, or protein can consist essentially of the specified amino acid sequence or sequences described herein, such that other components of the functional variant, e.g., other amino acids, do not materially change the biological activity of the functional variant. In this regard, the inventive TCR, polypeptide, or protein can, for example, consist essentially of the amino acid sequence of any of SEQ ID NOs: 2 to 9, or a combination thereof. Also, for instance, the inventive TCRs, polypeptides, or proteins can consist essentially of the amino acid sequence(s) of any of SEQ ID NOs: 10 to 17, or a combination thereof.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to gp100, detect cancer in a host, or treat or prevent cancer in a host, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, lipidated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), Altor Bioscience (Miramar, Fla.), and Multiple Peptide Systems (San Diego, Calif.). In this respect, the inventive TCRs, polypeptides, and proteins can be synthetic, recombinant, isolated, and/or purified.

Further provided by the invention is a nucleic acid comprising a nucleotide sequence encoding any of the TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins, or functional portions or functional variants thereof. For example, the nucleic acid can comprise a nucleotide sequence comprising any of SEQ ID NOs: 18 to 25 (which encode variable regions), SEQ ID NOs: 26 to 33 (which encode full length chains), or any combination thereof. The nucleotide sequence alternatively can comprise a nucleotide sequence which is degenerate to any of the aforementioned nucleotide sequences.

The nucleic acid of the invention can comprise a coding sequence that has undergone codon optimization, i.e., the non-native coding sequence is a product of codon optimization. Codon optimization is a strategy in which codons within a cloned gene, which codons are not generally used by the host cell translation system, termed "rare codons," are changed by in vitro mutagenesis to preferred codons without changing the amino acids of the synthesized protein (Bradel-Tretheway et al., *J Virol Meth* 111: 145-156 (2003); Ramakrishna et al., *J Virol* 78: 9174-9189 (2004)). In addition, the inventive nucleic acid can be further modified, e.g., codon optimized, to improve the folding of the RNA, such that the folding of the RNA transcript encoded by the nucleic acid is minimized. Without being bound to any particular theory, it is currently believed that the predicted minimized free energy, as determined by, for example, molecular modeling computer programs, correlates with minimized folding of the RNA, which, in turn, facilitates ribosome binding to the RNA and allows efficient expression of the RNA.

A given nucleotide sequence can be codon-optimized through the use of publicly-available computer programs, such as "Upgene: A Web-based DNA codon optimization algorithm," available on the internet at the website for the Recombinant Vaccine Center at the University of Pittsburgh Molecular Medicine Institute, and the "Codon Optimizer Tool," which is freeware available on the internet. Alternatively, a nucleotide sequence can be optimized through the services of companies, such as Blue Heron Bio, Inc. (Bothell, Wash.) and GenScript Corp. (Piscataway, N.J.).

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-CI, pMAM and pMAMneo (Clontech).

Preferably, the recombinant expression vector is a viral vector. Viral vectors are known in the art and include, for instance, retroviral vectors, adenoviral vectors, aden-associated viral vectors, pox viral vectors, vaccinia viral vectors, modified vaccinia viral vectors, and herpes simplex viral vectors. More preferably, the viral vector is a retroviral vector or a lentiviral vector.

The recombinant expression vector can be a yeast expression vector, such as, for example, pYES-DEST52, pAO815, pGAPZ, pPIC3.5 k, pYC2/CT, pYD1, pESC-LEU, and the like. The yeast in which the nucleic acid is to be expressed can be any yeast, such as, for instanct, *S. pombe, S. cerevisiae, Pichia pastoris*, etc. The yeast expression vector can be an inducible expression vector, e.g., a heat-inducible expression vector, or can be an expression vector which mediates constitutive expression. Such yeast expression vectors are known in the art.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2µ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL). More preferably, the host cell is a T cell. The T cell can be any T cell, such as any of those described herein. Preferably, the T cell is a $CD8^+$ T cell or a $CD4^+$ T cell.

Also provided by the invention is a population of cells comprising at least one host cell or human cell described herein. The population of cells can be a heterogeneous population comprising the human cell or host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of the inventive human cells or host cells (e.g., consisting essentially of) comprising the recombinant expression vector. The population also can be a clonal population of cells, in which all cells of the population are clones of a single human cell or host cell comprising a recombinant expression vector, such that all cells of the population are genetically identical and/or comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs described herein, wherein the functional portion binds to amino acids 154-062 of gp100 (SEQ ID NO: 1). Preferably, the functional portion is a variable region of one of the TCRs described herein.

The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The invention further provides a conjugate, e.g., a bioconjugate, comprising any of the inventive human cells, TCRs, polypeptides, or proteins (including any of the functional portions or variants thereof), nucleic acids, recombinant expression vectors, host cells, populations of cells, antibodies, or antigen binding portions thereof, or a combination thereof, and a therapeutic agent, a detectable moiety, or both a therapeutic agent and a detectable moiety.

The therapeutic agent can be any agent that yields a therapeutic effect against a disease, condition, or malady when administered to a host afflicted with the disease, condition, or malady. The disease, condition, or malady can be any disease, condition, or malady, such as an autoimmune disease, an infection (by e.g., a parasite, bacteria, or virus), or a cancer (e.g., any of the cancers described herein). Preferably, the therapeutic agent is an anti-cancer therapeutic agent. More preferably, the anti-cancer therapeutic agent is a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The detectable moiety can be any agent that can be detected through, for example, an assay, (e.g., a chemical or biophysical assay). The detectable moiety can comprise, for example, a radioisotope, a fluorophore (e.g., fluorescein isothiocyanate (FITC), phycoerythrin (PE)), an enzyme (e.g., alkaline phosphatase, horseradish peroxidase), element particles (e.g., gold or silver particles), and the like. Such detectable moieties are known in the art.

Methods of synthesizing conjugates in general, are known in the art. See, for instance, Hudecz, F., *Methods Mol. Biol.* 298: 209-223 (2005) and Kirin et al., *Inorg Chem.* 44 (15): 5405-5415 (2005).

In a preferred embodiment of the invention, the conjugate comprises one of the inventive polypeptides or proteins described herein in a soluble form. The conjugate, for example, comprises a soluble TCR protein and a therapeutic agent and/or detectable moiety.

The inventive human cells, TCRs, polypeptides, proteins, (including functional portions and functional variants thereof), nucleic acids, recombinant expression vectors, host cells, populations of cells, and antibodies (including antigen binding portions thereof), can be isolated and/or purified. The term "isolated" as used herein means having been removed from its natural environment. The term "purified"

as used herein means having been increased in purity, wherein "purity" is a relative term, and not to be necessarily construed as absolute purity. For example, the purity can be at least about 50%, can be greater than 60%, 70% or 80%, or can be 100%.

The inventive human cells, TCRs, polypeptides, proteins (including functional portions and variants thereof), nucleic acids, recombinant expression vectors, host cells populations of cells, antibodies (including antigen binding portions thereof), and conjugates, all of which are collectively referred to as "inventive TCR materials" hereinafter, can be formulated into a composition, such as a pharmaceutical composition. In this regard, the invention provides a pharmaceutical composition comprising any of the human cells, TCRs, polypeptides, proteins, functional portions, functional variants, nucleic acids, expression vectors, host cells, populations of cells, antibodies (including antigen binding portions thereof), and/or conjugates, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agent.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive TCR materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can consist of (a) liquid solutions, such as an effective amount of the inventive TCR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive TCR material in a flavor, usually sucrose and acacia or tragacanth, as well as pastilles comprising the inventive TCR material in an inert base, such as gelatin and glycerin, or sucrose and acacia, emulsions, gels, and the like containing, in addition to, such excipients as are known in the art.

The inventive TCR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., human T cells, the cells are administered via injection.

Additionally, the inventive TCR materials, or compositions comprising such inventive TCR materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to gp100, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art, including, for instance, the methods described herein as Example 1.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a linker to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the inventive TCR materials to the targeting moiety. One of ordinary skill in the art recognizes that sites on the inventive TCR materials, which are not necessary for the function of the inventive TCR materials, are ideal sites for attaching a linker and/or a targeting moiety, provided that the linker and/or targeting moiety, once attached to the inventive TCR materials, do(es) not interfere with the function of the inventive TCR materials, i.e., the ability to bind to a cancer antigen, or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive pharmaceutical compositions comprising any of the inventive human cells, TCRs, polypeptides, proteins, nucleic acids, recombinant expression vectors, host cells, populations of cells, or conjugates can be used in methods of treating or preventing cancer. Without being bound to a particular theory, the inventive TCRs are believed to bind specifically to gp100, e.g., gp100$_{154-162}$, such that the TCR (or related inventive polypeptide or protein) when expressed by a cell is able to mediate an immune response against the cell expressing gp100. As mentioned herein, gp100 is expressed on the surface of tumor cells. In this regard, the invention provides a method of treating or preventing cancer in a host, comprising administering to the host any of the pharmaceutical compositions described herein in an amount effective to treat or prevent cancer in the host.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a host. The method comprises (i) contacting a sample comprising cells of the cancer any of the inventive human cells, TCRs, polypeptides, proteins, nucleic acids, recombinant expression vectors, host cells, populations of cells, antibodies, or antigen binding portions thereof, or conjugates described herein, thereby forming a complex, and detecting the complex, wherein detection of the complex is indicative of the presence of cancer in the host.

With respect to the inventive method of detecting cancer in a host, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting step can take place in vitro or in vivo with respect to the host. Preferably, the contacting is in vitro.

Also, detection of the complex can occur through any number of ways known in the art. For instance, the inventive human cells, TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein human cells, host cells, or populations of cells are administered, the cells can be cells that are allogeneic or autologous to the host. Preferably, the cells are autologous to the host.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is colorectal cancer or melanoma.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLE 1

This example demonstrates a method of obtaining a murine TCR reactive with a human gp100 epitope.

The first part of the method comprises immunizing HLA-A*0201 (A2.1) transgenic mice with human gp100 peptide and then functionally assaying the bulk cultures of splenocytes obtained therefrom.

HLA-A*0201 (A2.1) transgenic mice were immunized with 100 µg of the gp100$_{154-162}$ peptide (KTWGQYWQV; SEQ ID NO: 34) and 120 µg of the I-Ab-binding synthetic T helper peptide representing residues 128-140 of the hepatitis B virus core protein (HBV-Core) emulsified in incomplete Freund's adjuvant. The mice were re-immunized with the same dose of antigens emulsified in incomplete Freund's adjuvant seven days after the first immunization. Spleens of the immunized mice were harvested one week after the second immunization.

HLA-A2 transgenic mouse splenocytes (from un-immunized mice) were irradiated (irradiated with 3000 rads), activated with lipopolysaccharide (LPS), and pulsed with 0.01 µg/ml of gp100$_{154-162}$ peptide and 10 µg/ml of human β2-microglobulin. Splenocytes ($3\times10^6$) were stimulated in 24 well-plate culture (RPMI 1640, with 10% of fetal bovine serum (FBS)) with an equal number of the irradiated, activated, and pulsed splenocytes. The splenocytes from the immunized mice were stimulated in this manner every 7-10 days with the addition of 10 CU/ml of IL-2 added to the culture media. Eight days after the third re-stimulation, the cells were tested for antigen recognition and gp100$_{154-162}$ tetramer binding.

To test whether the TCRs of the cells recognized antigen, T cells ($1\times10^5$) were cultured with equal number of target cells (T2 cells pulsed with the gp100$_{154-162}$ peptide or human melanoma cells expressing gp100 (Mel526)) or negative control cells (human gp100-negative melanoma cells (MelA375) or T2 cells pulsed with an irrelevant peptide (β-gal)). Antigen recognition by the T cells was indicated by the amount of IFN-γ secreted by the T cells, which was measured by ELISA using the ENDOGEN® Human IFNγ Colorimetric ELISA according to the manufacturer's instructions.

Figure 1:
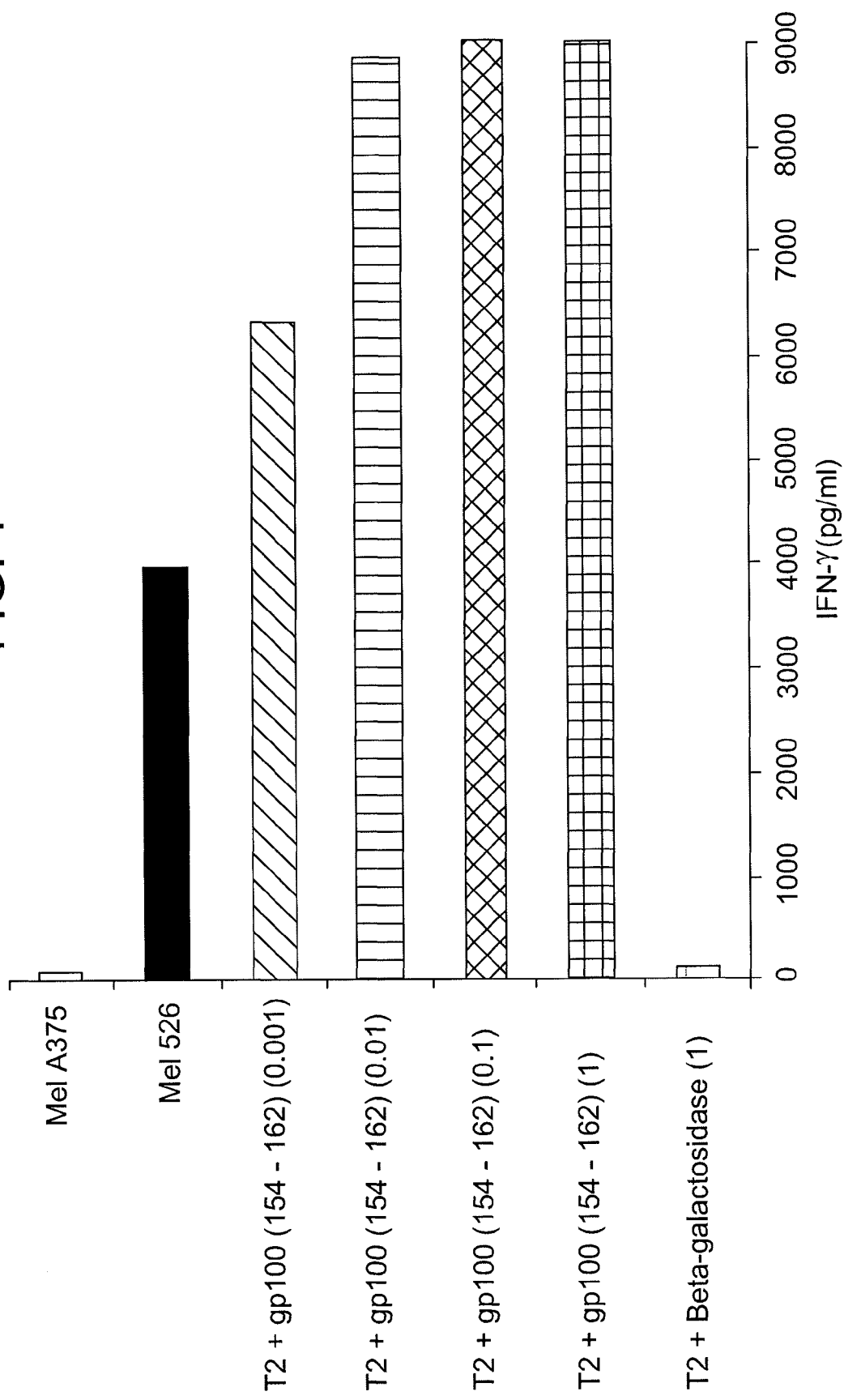

As shown in FIG. 1, T cells from HLA-A2 mice immunized with gp100$_{154-162}$ peptide recognized T2 cells pulsed with as little as 1 nM gp100$_{154-162}$ peptide and also recognized gp100-expressing Mel526 cells.

To test whether the TCRs of the cells could bind to gp100$_{154-162}$ tetramers, T cells were labeled with anti-mouse CD8-FITC mAb and gp100$_{154-162}$-HLA-A2 tetramer or a negative control tetramer (gp100$_{209-217}$-HLA-A2 tetramers). To verify that the negative control was properly working, human gp100$_{209-217}$-specific T cell clones were labeled with anti-human CD8-fluoroscein isothiocyanate (FITC) mAb and gp100$_{209-217}$-HLA-A2 tetramers. Tetramer binding was measured by flow cytometry, as the tetramers were labeled with PE.

Figure 2:
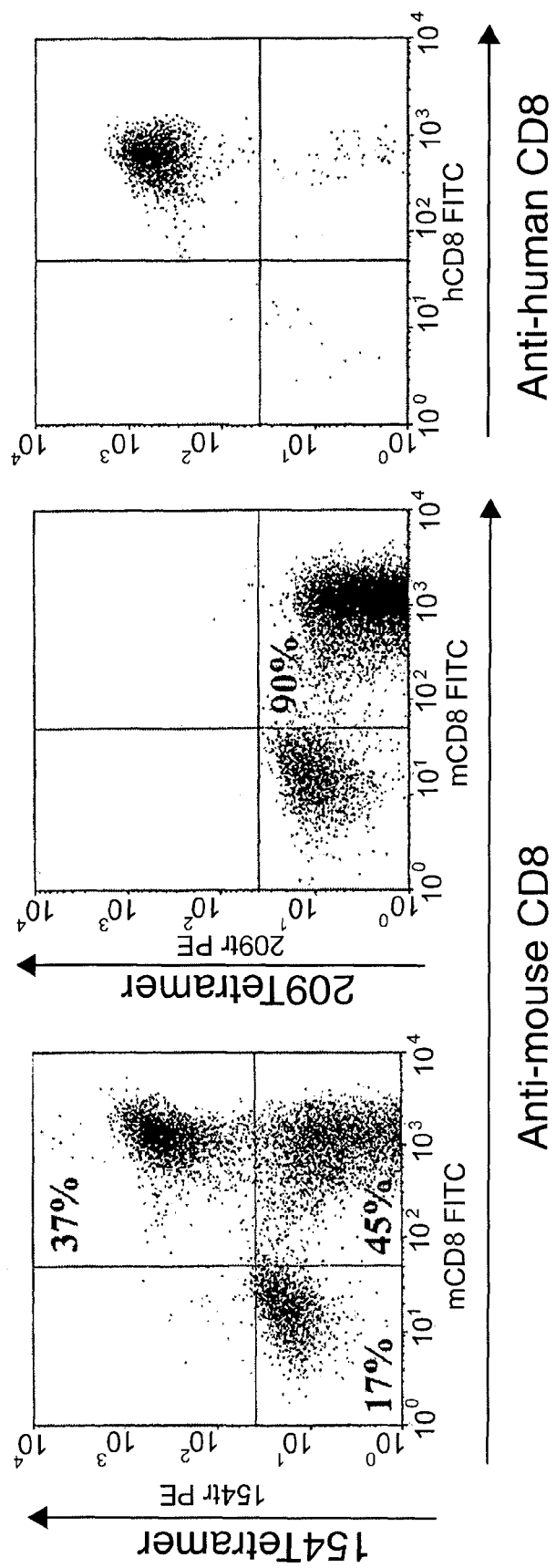

As shown in FIG. 2, T cells from HLA-A2 mice immunized with gp100$_{154-162}$ bound to gp100$_{154-162}$ tetramers and not to the negative control tetramers (gp100$_{209-217}$ tetramers).

Collectively, FIGS. 1 and 2 suggest that the bulk culture of splenocytes from gp100$_{154-162}$-immunized transgenic mice contained T cells with TCRs specific for gp100$_{154-162}$. The next part of the method comprised isolating T cell clones having activity against gp100$_{154-162}$ from the bulk culture.

T cells from the bulk culture were plated in 96-well round bottom plates at 0.3, 1, 3, or 10 cells/well in 100 μL media additionally containing 10 CU/ml of IL-2, 5×10$^4$ irradiated T2 cells (irradiated at 20,000 rads) pulsed with gp100$_{154462}$ peptide (0.01 μg/ml), and 2-3×10$^5$ irradiated C57BL6 splenocytes (irradiated at 3000 rads). Within a year, 29 clones, including a single clone (clone Sp(0.01)A) were tested for antigen recognition and tetramer binding.

To test whether the TCRs of the cells recognized antigen, the T cells of individual wells were assayed as essentially described above. Briefly, T cells (1×10$^5$) were cultured with an equal number of target cells (gp100$_{154-162}$ peptide-pulsed T2 cells or human melanoma cells expressing gp100 (Mel526)) or negative control cells (human gp100-negative melanoma cells (MelA375) or T2 cells pulsed with irrelevant peptide (gp100$_{209-217(m)}$ peptide). Antigen recognition by the T cells were measured by carrying out ELISAs which assayed the amount of IFN-γ secreted by the T cells.

Figure 3:
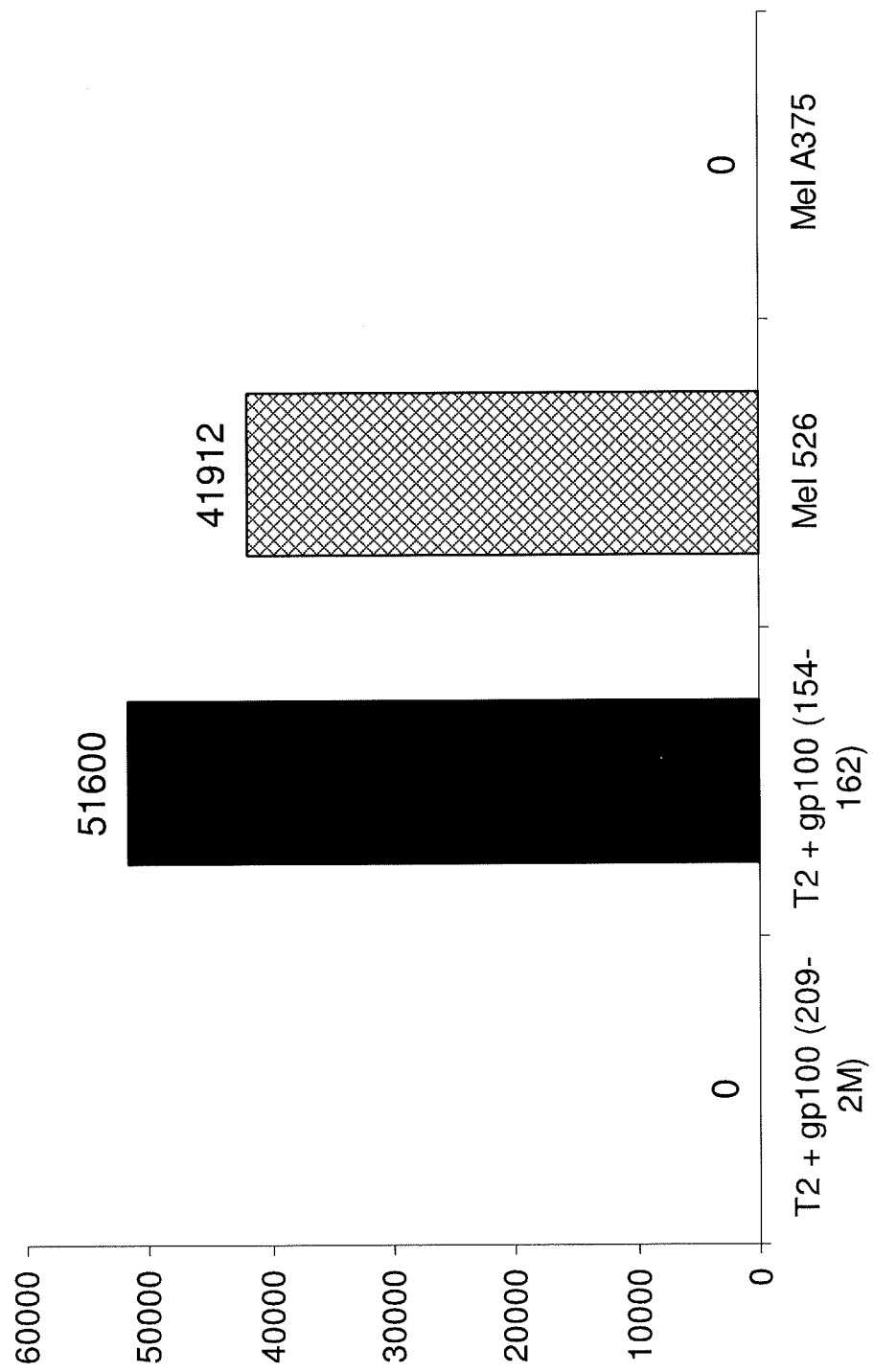

As shown in FIG. 3, clone Sp(0.01)A recognized the gp100$_{154-162}$ peptide and Mel 526 cells.

To test for tetramer binding, the T cells of individual wells were labeled as described above. Briefly, T cells were labeled with anti-mouse CD8-FITC mAb and gp100$_{154-162}$-HLA-A2 tetramer or with a negative control tetramer (gp100$_{269-217}$-HLA-A2 tetramer). To verify that the negative control was working, human T cell clones specific for gp100$_{209-217}$ peptide were labeled with anti-human CD8-FITC mAb and gp100$_{269-217}$-HLA-A2 tetramer. Flow cytometry was subsequently carried out to measure the tetramer binding.

Figure 4:
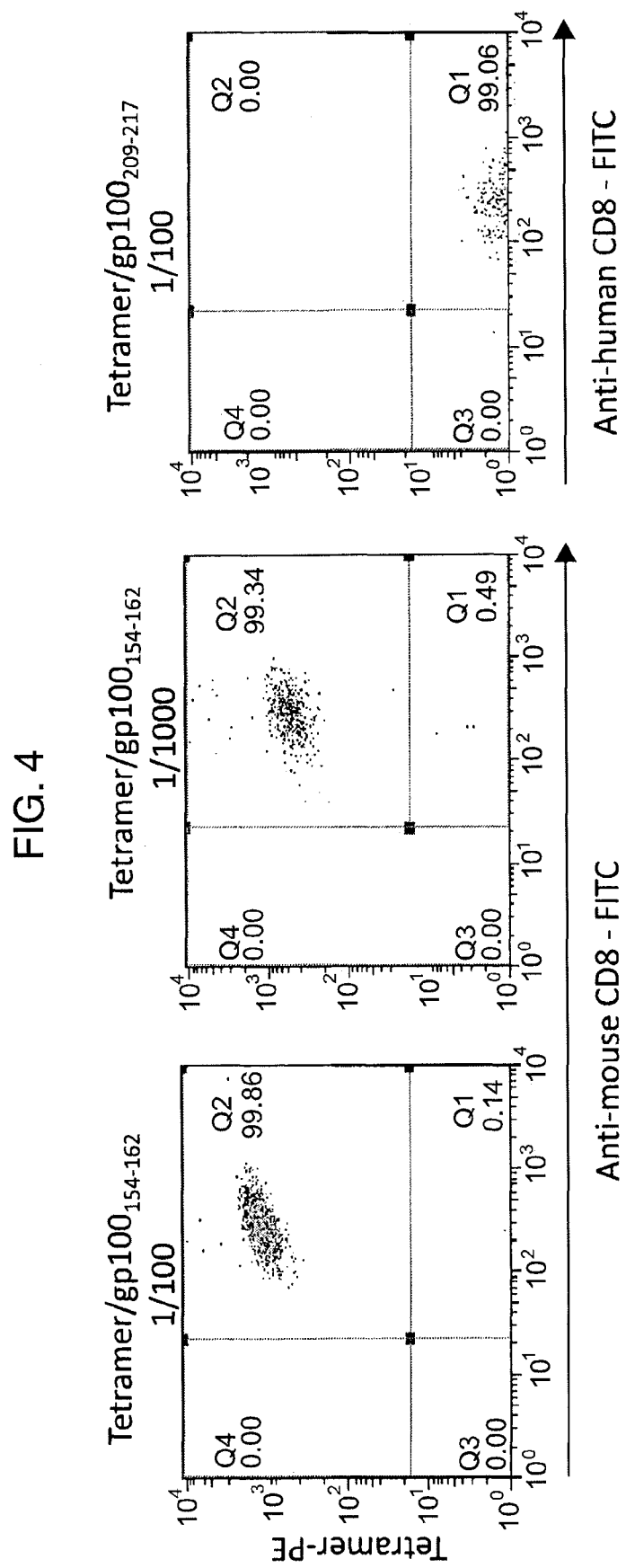

As shown in FIG. 4, T cells of clone Sp(0.01)A bound to the gp100$_{154-162}$ tetramer and not the gp100$_{209-217}$ tetramer.

FIGS. 3 and 4 collectively suggest that the T cell clone Sp(0.01)A comprises a TCR which is specific to the gp100$_{154-162}$ peptide. The molecular cloning of the TCR of this clone was subsequently carried out.

Total RNA from Sp(0.01)A T cell clones was isolated using Qiagen RNeasy Mini Kit cDNA and was prepared using Clontech SMART™ RACE cDNA Amplification kit. 5' RACE was performed using Clontech SMART™ RACE kit and TCR gene-specific primers derived from the constant region of the mouse TCR α and β chains (3' TCRAC ggctactttcagcaggagga (SEQ ID NO: 36) and 3' TCRBC aggcctctgcactgatgttc (SEQ ID NO: 37)). The forward primers were Universal Primer mix for 5' end RACE from Clontech. The RACE products were then ligated into pcDNA3.1/V5-His Topo TA cloning vector, and transformed into Top10 bacteria. The transformed bacteria were plated onto ampicillin (Amp)-containing LB plates. Twenty-four colonies for each chain were selected and individually cultured in 1.2 ml of Amp-containing LB for plasmid DNA preparation. Plasmid DNA was isolated and sequenced using the following primers: 3' TCRACseq actggtacacagcaggttctgg (SEQ ID NO: 38) and 3' TCRBCseq aaggagaccttgggtggagtc (SEQ ID NO: 39) to determine the 5' gene specific primer. Full length TCR were then PCRd from 5' RACE ready cDNA using the primers 5'TRA7D3*01: caccatgaaatccttgagtgtttcc (SEQ ID NO: 40) and 3' TCRA: tcaactggaccacagcctcagc (SEQ ID NO: 41) for the α chain.

For the β chain, PCRs were first performed using the primers: 5'TRB13-3*01: caccatgggctccagactcttcttt (SEQ ID NO: 42) and 3' TCRBC: aggcctctgcactgatgttc (SEQ ID NO: 43), 5' TCRBCseqreverse: aaggagaccttgggtggagtc (SEQ ID NO: 44), and 3' TCRB: tcatgaattctttcttttgaccatagcc (SEQ ID NO: 45). The two PCR fragments were linked together using PCR with primers 5'TRB13-3*01: caccatgggctccagactcttcttt (SEQ ID NO: 46) and 3' TCRB: tcatgaattctttcttttgaccatagcc (SEQ ID NO: 47). Advantage® HF 2 Taq polymerase was the polymerase used in cloning the full length cDNA of each chain of the TCR. For each PCR, the reaction conditions were as follows: 95° C. for 1 minute, 35 cycles of 95° C. for 30 sec followed by 68° C. for 3 minutes, 68° C. for 3 minutes and 4° C. till the end. Final PCR products were cloned into pcDNA3.1/V5-His Topo TA cloning vector and transformed into Top10 bacterial. Plasmid DNA was then isolated and sequenced using primers from the vectors.

The sequences of the α and β chains of the TCR of the Sp(0.01)A clone are shown in FIG. 5.

For the TCR nomenclature, the sequences of the Sp(0.01)A TCR were compared to the sequences published in the online IMGT/V-Quest database. The α chain of the TCR was named TRAV7D-3*01, while the β chain was named TRBV13-3*01 N1 TRBD2*01 N2 TRBJ2-7*01

This example demonstrated that a T cell receptor specific for human melanoma antigen gp100$_{154-162}$ was isolated and cloned from HLA-A2 transgenic mice.

EXAMPLE 2

This example demonstrates a method of preparing a human cell comprising a murine TCR specific for the gp100$_{154-162}$ peptide.

Template DNA was PCRd from Sp(0.01)A TCR full length cDNA plasmid using primer pairs: 5' alpha RNA: aactaatacgactcactatagggagacaccatgaaatccttgagtgtttcc (SEQ ID NO: 48) and 3' alpha RNA: tttttttttttttttttttttttttttttttttttttttttttttttttttttttttttcaactggaccacagcctcagc (SEQ ID NO: 49); and 5' beta RNA: aactaatacgactcactatagggagacaccatgggctccagactcttcttt (SEQ ID NO: 50) and 3' beta RNA: Mattattttttttttttttttttttatttttttattttttatttttattttttcatgaattattatttgaccatagcc (SEQ ID NO: 51). The PCR products were purified and RNA encoding Sp(0.01)A TCR α and β chains were in vitro transcribed using these templates following the mMachine protocol from Ambion. RNAs were recovered using Qiagen RNeasy mini kit, quantified using spectrophotometer and stored in −80° C.

Human PBL were in vitro activated using 1 ng/ml of OKT-3 (anti-human CD3 mAb) and 50 CU/ml of recombinant human IL-2 for 4-17 days. In some experiments, CD8+ and CD4+ T cells were positively selected on day 13 and day 14. Cells were washed with OPTI-MEM (Invitrogen) twice and resuspended in OPTI-MEM at a concentration of $2.5 \times 10^7$ cells/ml. Cells and cuvettes were pre-chilled on ice for at least 5 min prior to electroporation. Cells ($2.5 \times 10^6$ in 100 µl) was mixed with 5 µg of RNA in a 1.5 ml tube and transferred into a 2-mm cuvette (Harvard Apparatus BTX, Part #45-0125). The cells were electroporated at 500V, 500 µs is for 1 pulse with an ECM830 Electro Square Wave Porator™ (Harvard Apparatus BTX). Immediately after electroporation, the cells were transferred (using pipette included in the cuvette package) to fresh culture media and incubated at 37° C. The cells were subsequently tested for antigen recognition and tetramer binding as described above.

Briefly, for tetramer binding, human PBLs were electroporated with Sp(0.01)A TCR RNA or mock electroporated (with OPTI-MEM®) and stained with allophycocyanin (APC)-labeled anti-human CD8 mAb and phycoerythrin (PE)-labeled $gp100_{154-162}$ tetramer or FITC-labeled anti-murine TCR beta chain Ab. Fluorescence was measured via flow cytometry.

As shown in FIG. 6, human PBLs electroporated with Sp(0.01)A TCR RNA specifically bound to the $gp100_{154-162}$ tetramer. Binding to this tetramer was dependent upon expression of the TCR as those cells expressing the mouse TCR β chain bound to the tetramer.

For antigen recognition, human PBLs were electroporated with RNA encoding the Sp(0.01)A TCR, a human TCR specific for $gp100_{209-217}$, a human MART-1 TCR, a human/mouse hybrid TCR specific for MART-1, or a p53-specific TCR. The electroporated cells were co-cultured with target cells: (a) T2 cells pulsed with $10^{-11}$, $10^{-10}$, $10^{-9}$, $10^{-8}$, $10^{-7}$, $10^{-6}$ M $gp100_{154-162}$ peptide or with a negative control ($10^{-6}$ M $gp100_{209-217}$) or (b) melanoma cells expressing gp100 Mel 526, SK23 and 624; or negative control targets: Mel938, Mel888, MelA375, and MDA-231, all of which do not express gp100. IFN-γ secretion by the PBLs was measured by ELISA as previously described.

As shown in FIG. 7A, human PBLs electroporated with Sp(0.01)A TCR RNA recognized T2 targets pulsed with as little as 1 pg/ml of $gp100_{154-162}$ peptide. Also, these cells recognized melanoma cell lines expressing gp100, but did not recognize melanoma cell lines not expressing gp100 (FIG. 7B).

Whether the human PBLs expressing Sp(0.01)A TCR functions with human co-receptors was analyzed next. Human CD8+ T cells and CD4+ T cells were electroporated with Sp(0.01)A TCR RNA or mock electroporated (with media) and subsequently labeled with PE-labeled $gp100_{154-162}$ tetramer and FITC-labeled anti-human CD8 Ab. Fluorescence was measured by flow cytometry (FIG. 8A).

The electroporated CD4+ T cells and CD8+ T cells were then subjected to the antigen recognition and melanoma recognition assays described herein in which IFN-γ secretion by the T cells was measured by ELISA. Briefly, electroporated T cells were con-cultured with target cells: (a) T2 cells pulsed with $10^{-11}$, $10^{-10}$, $10^{-9}$, $10^{-8}$, $10^{-7}$, or $10^{-6}$ M $gp100_{154-162}$ peptide or control peptide ($10^{-6}$ M $gp100_{209-217}$) or (b) melanoma cells expressing gp100 (Mel526, MelSK23, and Mel624) or negative melanoma cells not expressing gp100: Mel938, Mel888, and MelA375.

As shown in FIG. 8B, both CD8+ T cells and CD4+ T cells electroporated with Sp(0.01)A TCR RNA recognized antigen in a dose-dependent manner. Also, both cell populations recognized only those melanoma cells expressing the correct antigen (FIG. 8C). The CD4+ T cells also demonstrated antigen-specific immunological responses, suggesting that the Sp(0.01)A TCR can function in the absence of the human CD8 co-receptor. The fact that this TCR can function in a CD8-independent manner suggests that it is a high affinity TCR for the $gp100_{154-162}$ peptide.

The mouse Sp(0.01)A TCR was then compared to its human counterpart. Human PBLs were electroporated with Sp(0.01)A TCR RNA or an RNA encoding a human TCR specific for $gp100_{154-162}$ (clone 1 or clone 2), or were mock electroporated. The electroporated cells were then stained with PE-labeled gp100154-162 tetramer and APC-labeled anti-human CD8 Ab. Flow cytometry was performed to measure the fluorescence (FIG. 9A). The electroporated cells were then subjected to the antigen recognition and melanoma recognition assays previously described.

As shown in FIGS. 9B and 9C, the Sp(0.01)A TCR functioned in an antigen-specific manner and produced a response that was at least 100 times greater than either human $gp100_{154-162}$-specific TCR.

This example demonstrated that the $gp100_{154-162}$-specific TCR isolated and cloned from transgenic mice can specifically bind to $gp100_{154-162}$ tetramers and can secrete IFN-γ upon tumor antigen recognition (both peptide pulsed target cells and melanoma cells) in the context of a human cell. This example also demonstrated that the functions of this TCR is human CD8 co-receptor independent. Furthermore, this TCR, as compared to the TCR of two human T cell clones specific for the same antigen, recognized human tumor antigen at least 100 times better.

EXAMPLE 3

This example demonstrates the frequency of variable regions amongst the $gp100_{154-162}$-specific clones.

As mentioned in Example 1, 29 T cell clones were isolated from the bulk culture of which one was Sp(0.01)A. The TCRs of the other 28 clones were sequenced as essentially described in Example 1, and the sequences were compared to those published in the online IMGT/V-Quest database. The frequency of the alpha and beta variable regions from each clone is shown in Table 1.

TABLE 1

| Clone Name | TCR chain | Name of variable region | Frequency |
|---|---|---|---|
| T2(1)C | alpha | TRAV10*02 | 11/12 |
|  | alpha | TRAV4D-4*03 | 1/12 |
|  | beta | TRBV12-2*01 | 14/14 |
| Sp(0.01)A | alpha | TRAV7D-3*01 | 14/15 |
|  | alpha | TRAV6D-6*02 | 1/15 |
|  | beta | TRBV13-3*01 | 7/7 |
| T2(1)A | alpha | TRAV7D-3*01 | 14/22 |
|  | alpha | TRAV6D-6*02 | 8/22 |
|  | beta | TRBV13-1*02 | 10/22 |
|  | beta | TRBV4*01 | 12/22 |
| T2(1)B | alpha | TRAV10*02 | 17/19 |
|  | alpha | TRAV4D-4*03 | 2/19 |
|  | beta | TRBV12-2*01 | 19/19 |
| T2(1)K | alpha | TRAV10*02 | 14/16 |
|  | alpha | TRAV4D-4*03 | 2/16 |
|  | beta | TRBV12-2*01 | 21/21 |
| Sp(0.1)A10 | alpha | TRAV9D-3*02 | 15/21 |
|  | alpha | TRAV6D-5*01 | 6/21 |
|  | beta | TRBV12-2*01 | 17/17 |
| T2(1)J | alpha | TRAV10*02 | 6/6 |
|  | beta | TRBV12-2*01 | 17/17 |

TABLE 1-continued

| Clone Name | TCR chain | Name of variable region | Frequency |
|---|---|---|---|
| T2(1)N | alpha | TRAV10*02 | 12/21 |
| | alpha | TRAV16*05 | 9/21 |
| | beta | TRBV12-2*01 | 19/19 |
| T2(1)H | alpha | TRAV3-3*02 | 14/16 |
| | alpha | TRAV10*02 | 2/16 |
| | beta | TRBV19*01 | 15/22 |
| | beta | TRBV12-2*01 | 5/22 |
| | beta | TRBV13-3*01 | 1/22 |
| | beta | TRBV5*01 | 1/22 |
| T2(1)P | alpha | TRAV10*02 | 17/18 |
| | alpha | TRAV4D-4*03 | 1/18 |
| | beta | TRBV12-2*01 | 11/12 |
| | beta | TRBV12-2*02 | 1/12 |
| Sp(0.01)B | alpha | TRAV7D-3*01 | 12/14 |
| | alpha | TRAV6D-6*02 | 2/14 |
| | beta | TRBV13-3*01 | 14/15 |
| | beta | TRBV19*01 | 1/15 |
| Sp(0.01)C | alpha | TRAV13D-2*01 | 20/20 |
| | beta | TRBV31*01 | 19/19 |
| Sp(1) A | alpha | TRAV6D-3*01 | 17/21 |
| | alpha | TRAV13-2*02 | 4/21 |
| | beta | TRBV5*01 | 22/22 |
| T2(1)G | alpha | TRAV10*02 | 17/18 |
| | alpha | TRAV4D-4*03 | 1/18 |
| | beta | TRBV12-2*01 | 13/13 |
| T2(1)M | alpha | TRAV13D-2*01 | 14/17 |
| | alpha | TRAV4D-4*03 | 1/17 |
| | alpha | TRAV10*02 | 1/17 |
| | alpha | TRAV7D-3*01 | 1/17 |
| | beta | TRBV13*01 | 14/22 |
| | beta | TRBV5*01 | 1/22 |
| | beta | TRBV12-2*01 | 7/22 |
| T2(1)O | alpha | TRAV9D-4*02 | 7/17 |
| | alpha | TRAV7D-3*01 | 10/17 |
| | beta | TRBV1*01 | 23/23 |
| T2(1)Q | alpha | TRAV10*02 | 17/22 |
| | alpha | TRAV7D-3*01 | 1/22 |
| | alpha | TRAV13D-2*01 | 4/22 |
| | beta | TRBV12-2*01 | 17/17 |
| T2(1)T | alpha | TRAV13D-2*01 | 16/16 |
| | beta | TRBV12-2*01 | 9/21 |
| | beta | TRBV1*01 | 4/21 |
| | beta | TRBV31*01 | 7/21 |
| | beta | TRBV5*01 | 1/21 |
| T2(1)Cpost | alpha | TRAV10*02 | 20/23 |
| | alpha | TRAV4D-4*04 | 3/23 |
| | beta | TRBV12-2*01 | 18/18 |
| T2(0.01)A | alpha | TRAV6-7/DV9*06 | 3/7 |
| | alpha | TRAV4D-4*03 | 4/7 |
| | beta | TRBV13-3*01 | 11/11 |
| Sp(0.01)K | alpha | TRAV7D-3*01 | 16/22 |
| | alpha | TRAV6-7/DV9*06 | 6/22 |
| | beta | TRBV13-3*01 | 23/23 |
| Sp(0.01)D | alpha | TRAV8-1*01 | 3/4 |
| | beta | TRBV13-3*01 | 5/5 |
| T2(1)S | alpha | TRAV10*02 | 15/17 |
| | alpha | TRAV4D-4*03 | 2/17 |
| | beta | TRBV12-2*01 | 8/8 |
| Sp(5)B | alpha | TRAV6-7/DV9*06 | 20/20 |
| | beta | TRBV12-2*01 | 1/16 |
| | beta | match genbank AY499163 | 15/16 |
| T2(1) U | alpha | TRAV8-1*01 | 18/20 |
| | alpha | TRAV7D-2*-3 | 1/20 |
| | alpha | TRAV12D-2*02 | 1/20 |
| | beta | TRBV3*01 | 7/7 |
| T2(1) I | alpha | TRAV13D-3*01 | 2/17 |
| | alpha | TRAV10*02 | 12/14 |
| | beta | TRBV12-2*01 | 8/8 |
| T2(1) L | alpha | TRAV10*02 | 17/19 |
| | alpha | TRAV4D-4*03 | 2/19 |
| | beta | TRBV12-2*01 | 15/15 |
| T2(1) R | alpha | TRAV8-1*01 | 1/9 |
| | alpha | TRAV10*02 | 4/9 |
| | alpha | TRAV7D-3*01 | 3/7 |
| | alpha | TRAV12D-2*02 | 1/9 |
| | beta | TRBV1*01 | 11/11 |
| Sp(1)B | alpha | TRAV6-7/DV9*06 | 1/5 |
| | alpha | TRAV4D-4*03 | 1/5 |
| | alpha | TRAV10*02 | 2/5 |
| | alpha | TRAV8-a*01 | 1/5 |
| | beta | unknown | |

This example demonstrated the frequency of the variable regions of each of the chains of the TCRs expressed by the gp100$_{154-162}$-specific clones.

EXAMPLE 4

This example demonstrates the activity of other murine TCRs specific for gp100.

Human PBLs ($1\times10^6$) were electroporated with 2 μg RNA encoding each of the alpha and beta chains of the TCRs of clones Sp(0.01A), T2(1)B, Sp(0.1)A10, and T2(1)C as essentially described in Example 2. The nucleotide sequences encoding each of the alpha and beta chains of the TCRs from clones T2(1)B, Sp(0.1)A10, and T2(1)C are shown in FIGS. 10A-C, respectively. The cells were then tested for tetramer binding and antigen recognition against T2 cells pulsed with varying amounts of gp100$_{154-162}$. For tetramer binding, the electroporated cells were stained with PE-linked HLA-A2/gp100$_{154-162}$ tetramer and with FITC-linked anti-murine TCR beta chain antibody (Vb) 24 hours post-transfection. Tetramer and antibody binding was measured by flow cytometry as described in Example 2. Table 2 indicates the percentage per percentage of mouse beta chain positive cells.

TABLE 2

| Clone Name | % tetramer positive cells |
|---|---|
| Sp(0.01)A | 100% |
| T2(1)B | 13% |
| Sp(0.1)A10 | 10% |
| T2(1)C | Undetectable |

The electroporated human PBLs were co-cultured overnight with gp100$_{154-162}$ peptide-pulsed T2 cells and the concentration of IFN-γ in the supernatant was subsequently measured by ELISA. Table 3 indicates the lowest gp100$_{154-162}$ peptide concentration that was specifically recognized by the electroporated human PBLs.

TABLE 3

| Clone Name | Minimal concentration |
|---|---|
| Sp(0.01)A | $<10^{-10}$M |
| T2(1)B | $10^{-9}$-$10^{-10}$M |
| Sp(0.1)A10 | $10^{-9}$M |
| T2(1)C | $10^{-6}$M |

Purified human CD8$^+$ T cells were electroporated with RNA encoding TCRs from clones Sp(0.01A), T2(1)B, Sp(0.1)A10, and T2(1)C and co-cultured overnight with HLA-A2$^+$/hgp100$^+$ human melanoma cells (624, 526 and SK23). The concentration of IFN-γ in the supernatant was subsequently measured by ELISA. Table 4 indicates the relative levels of IFN-γ produced by the electroporated cells. Each plus sign indicates at least one log (10 times) increase in IFN-γ production.

TABLE 4

| Clone Name | Tumor reactivity in human CD8+ T cells |
|---|---|
| Sp(0.01)A | +++ |
| T2(1)B | ++/+++ |
| Sp(0.1)A1 0 | + |
| T2(1)C | Undetectable |

Purified human CD4+ T cells were electroporated with RNA encoding the TCRs of clones Sp(0.01A), T2(1)B, Sp(0.1)A10, and T2(1)C and co-cultured overnight with HLA-A2+/hgp100+ human melanoma cells (624, 526 and SK23). The concentration of IFN-γ in the supernatant was measured by ELISA. Table 5 indicates the relative levels of IFN-γ produced by the electroporated cells. Each plus sign indicates at least one log (10 times) increase in IFN-γ production.

TABLE 5

| Clone Name | Tumor reactivity in human CD4+ T cells |
|---|---|
| Sp(0.01)A | +++ |
| T2(1)B | – |
| Sp(0.1)A10 | – |
| T2(1)C | Undetectable |

Based on the above results, the TCR of clone Sp(0.01)A demonstrated the highest avidity for gp100$^{154162}$, whereas the avidities of the TCRs of clones T2(1)B and Sp(0.1)A10 was intermediate, while the avidity of the TCR of clone T2(1)C was the lowest.

This example demonstrated other murine TCRs that are specific for the gp100$_{154-162}$ epitope.

EXAMPLE 5

This example demonstrates the relative activities of tumor antigen specific TCRs.

Human PBL were electroporated with RNAs encoding either hgp100$_{154-162}$-specific human TCRs or mouse TCR (Sp0.01A). RNA expression was measured by tetramer binding as assessed by FACS. The activity of the PBL expressing the TCRs were compared via an IFN-γ release assay. The results are shown in Table 6.

TABLE 6

| Assay $_{154-162}$Tetramer binding (%) | | Human TCR 1 1 | Human TCR 2 6 | Human TCR 3 4 | Sp0.01A 95 |
|---|---|---|---|---|---|
| IFN-y release (pg/ml) | | | | | |
| HLA-A2+, hgp100+ melanoma | Mel 526 | 11 | 894 | 41 | 20533 |
| | SK 23 | 11 | 944 | 108 | 43346 |
| | Mel 624 | 16 | 622 | 41 | 37562 |
| HLA-A2−, hgp100− | Mel 938 | 21 | 5 | 15 | 6 |
| | Meal 888 | 38 | 9 | 0 | 13 |
| HLA-A2+, hgp100− melanoma | A 375 | 56 | 45 | 37 | 45 |

As shown in Table 6, the activity of PBL expressing the Sp0.01A mouse gp100 specific TCR was dramatically higher than the human gp100 specific TCR.

The relative avidities of the mouse gp100-specific TCR (Mo h154 TCR) and human MART TCR (Hu Mart1 TCR (F4)) were also compared. As shown in FIG. 11, the mouse 154 TCR exhibited 10-100 fold greater recognition of tumor antigens as measured by an ex vivo cytokine release assay. This was observed for both pulsed targets (FIG. 11, left panel) and cultured human tumor cell lines (FIG. 11, right panel).

Additionally, a single transduction with recombinant retrovirus encoding the Sp0.01A TCR (the TCR from the most highly avid mouse T cell line) yielded approximately 90% of the human PBL expressing the hgp100$_{154-162}$-specific TCR. As shown in Table 7, these cells were able to specifically produce IFN-γ upon co-culture with human melanoma cell lines expressing the target antigen (gp100) and the appropriate restriction element (HLA-A2).

TABLE 7

| Assay $_{154-162}$Tetramer binding (%) | | Untransduced 1 | Transduced 88 |
|---|---|---|---|
| IFN-y release (pg/ml) | | | |
| HLA-A2+, hgp100+ melanoma | Mel 526 | 2 | 18523 |
| | SK 23 | 4 | 48044 |
| | Mel 624 | 12 | 22811 |
| HLA-A2−, hgp100− melanoma | Mel 938 | 21 | 22 |
| | Meal 888 | 38 | 0 |
| HLA-A2+, hgp100− melanoma | A 375 | 56 | 31 |

PBLs were retrovirally transduced with a gp100:154-162-specific TCR, DMF4 MART-1 specific TCR, DMF5 MART-1 specific TCR, mDMF5 MART-1 specific TCR, or control vector (GFP). Cytolytic activity of the PBL were then assayed by a standard chromium release assay. As shown in FIG. 12, the DMF5 and gp154 TCRs provided the highest recognition of HLA-A2 expressing melanomas than the other TCRs.

The potential for crossreactivity of the murine anti-gp100 TCR with normal cells was tested using human PBL transduced with the retroviral vector expressing the anti-gp100 (154)TCR (1×10$^5$), which were co-cultured with test cell lines (1×10$^5$ cells). Twenty-four hours after co-culture, the concentration (pg/mL) of IFN-γ secreted in the medium was measured by ELISA. Only melanoma tumor cell lines were recognized by patient cells transduced with anti-gp100(154) retroviral vector.

This example demonstrated the relative activities of a TCR of the invention.

EXAMPLE 6

This example demonstrates a method of preparing cells for infusion, in accordance with the invention.

The following materials were used in the method: Ca++–Mg++–, Phenol red-free Hanks' balanced salt solution (HBSS) (BioWhittaker); RPMI 1640 with L-Glutamine (BioWhittaker); HEPES, 1M pH 7.0, stock (BioWhittaker); 2-Mercaptoethanol, 5.5×10$^{-2}$ M in D-PBS, stock (GIBCO BRL); Penicillin G sodium (10,000 units/10, streptomycin (10,000 mg/ml) stock (BioWhittaker); Gentamycin (50 mg/ml) stock (BioWhittaker); Ciprofloxacin (Cipro 1% solution, Bayer); Fungizone (250 mcg/ml stock; Bristol-Myers Squibb); AIM V serum free lymphocyte growth medium (GIBCO BRL); X-VIVO 20 serum free lymphocyte growth medium (BioWhittaker); 0.9% sodium chloride, USP (Baxter); Human Serum, type AB (Valley Biomedical); Human PBMC; Human albumin (Plasbumin-25, Bayer)); Recombinant human IL-2 (10$^6$ CU/ml) (Cetus Oncology Div, Chiron, wherein 50 Cetus units (CU)=300 International units (IU)); OKT3 (Ortho-anti-CD3) (Orthoclone); gp100 peptide 1.0 mg/ml stock; Lymphocyte separation medium (LSM) (ICN); Plastic pipettes, 2, 5, 10, 25, and 50 ml; Pipette tips, 200 ul and 1 ml; 96-well tissue culture plates, flat-bottom and U-bottom (Costar); 6 and 24 well non-tissue culture treated plates, (Falcon); Tissue culture flasks, vented cap, 25 and 175 cm$^2$ (Costar Corp); Centrifuge tubes, 15, 50 and 250 ml (Corning); Sampling site coupler (Baxter/Fenwal, Deerfield, Ill.); Solution transfer set (Baxter/Fenwal); Lifecell adapter set (Baxter/Fenwal); Interconnecting jumper tube, 8" (GIBCO); Solution transfer pump (Baxter/Fenwal); Culture bags, PL732 1 liter (Baxter/Fenwal); Culture bags, PL732 3 liter (Baxter/Fenwal); TCR retroviral vectors (GCsamAPB and MSGV1 AIB, National Gene Vector Laboratory, Indiana University); Antibody to murine TCR β chain (Bb Biosciences); QuickExtract™ DNA extraction solution 1.0.(Epicentre); First-strand cDNA synthesis Kit (Amersham Pharmacia biotech); STRATAGENE Absolutely RNA™ RT-PCR Miniprep Kit (STRATAGENE). All materials in contact with cells or their media are supplied sterile.

Peripheral blood lymphocytes (PBL) were stimulated, transduced, and reinfused in a similar fashion to previously approved clinical protocols. Briefly, PBL were isolated by leukopheresis. Lymphocytes were separated by centrifugation on a Ficoll-Hypaque cushion, washed in HBSS, then resuspended at a concentration of $1\times10^6$/ml in lymphocyte growth medium supplemented with 50 ng/ml OKT3, 300 IU/ml IL-2, and 5% human AB serum. If patients had a history of antibiotic allergy, the antibiotic was not used in the culture medium. After 2 days of culture, cells were collected, resuspended in fresh medium without OKT3, and plated onto tissue cultured plates that had been pre-coated with Retronectin and the TCR retroviral vectors, and transduction accomplished as follows.

All transductions were performed in the wells of 6-well plates. Wells were precoated with Retronectin followed by TCR retroviral vector. Retronectin, a recombinant chimeric fibronectin molecule, has been approved by FDA to be used in other clinical trials involving transduction of genes into human hematopoietic cells. The clinical GMP grade Retronectin was supplied by Takara Biomedicals, Japan. Retronectin was coated as follows: 2 mls of 1×PBS containing 50 μg/ml retronectin was placed in each well of 6-well plate at 4° C. overnight or at room temperature for 2 hours. Wells were blocked with 2 mls of 1% human albumin in 1×PBS at room temperature for 30 minutes and washed once with 2 mls of 1×PBS containing 2.5% HEPES, pH 7.0 (v/v). 6-12 mls of TCR retroviral supernatant were applied to each retronectin-coated well and incubated at 32° C. for 2 hours followed by 12-48 hours at 4° C. Retroviral supernatant was removed and up to $5\times10^6$ PBL cells in lymophocyte growth medium supplemented with 3001 U/ml IL-2, and 5% human AB serum was applied onto retronectin and retroviral vector coated wells. The culture was incubated at 37° C., 5% $CO_2$ incubator overnight.

The following day, the PBL were transferred to a second set of pre-coated retronectin retroviral vector tissue culture plates. Two days after the last transduction, the PBL cultures were assayed for the presence of the appropriate murine TCR β chain protein and for activity. Cells ($1\times10^6$) transduced with the gp100:154-162 TCR vector were stained with antibody for the murine TCR β chain protein, followed by analysis by FACS. Transduction was considered successful if >10% of the PBL were positive for the murine TCR β chain protein. To test for anti-tumor activity, $1\times10^5$ transduced PBL were coincubated with $1\times10^5$ target cells. Target cells were T2 cells pulsed with 1.0 microgram/ml gp100 peptide, and a control (Flu) peptide. After 24 hours of incubation, supernatants were harvested and IFN-γ quantified by ELISA capture assay. The transduced cultures that released >200 pg/ml of IFN-γ (and 4× background levels produced in control incubations) were considered biologically active.

At the end of transduction, cells were washed and maintained in lymphocyte growth medium supplemented with 3001 U/ml IL-2, and 5% human AB serum and maintained at a density of $1\times10^6$ cells/ml. The cultures were incubated at 37° C., 5% CO2 incubator until infusion. If cells had grown to sufficient numbers for patient treatment, a sample was collected for sterility before the beginning of PBL therapy.

A sample of TCR transduced PBL cells was collected 3 days prior to infusion and tested for replication-competent retrovirus (RCR) contamination by GALV envelope gene-PCR and $S^+/L^-$ assays to test replication-competent retrovirus (RCR) according to published methods (Chen et al., *Human Gene Ther.* 12: 61-70 (2001)). Samples for S+/L– will be sent to National Gene Vector Laboratory (NGVL, Indiana University) for analysis. PCR results (positive or negative) were available prior to the infusion of PBL cells. Definitive $S^+/L^-$ assay results were not available prior to cell infusion.

On days 14-20, the final product was prepared for patient infusion. The contents (cells and media) of flasks were transferred to 250 ml centrifuge tubes, while cells in Baxter culture bags were harvested using a Baxter/Fenwal continuous centrifuge cell harvester system. Aliquots were taken from representative bags and pooled for a gram test. Cells were spun to pellet (1000 rpm, 15 min, R/T) and combined in a single tube, then washed by resuspension in 0.9% sodium chloride followed by centrifugation, and finally resuspended in 45-400 ml of 0.9% sodium chloride. Human albumin (25%) was added to a final concentration of 2.5%. Aliquots were removed for cell count and viability testing by trypan blue exclusion, and for QC testing. The final product was then ready for infusion.

EXAMPLE 7

This example demonstrates a method of administering to humans cells expressing a TCR of the invention.

PBMC were obtained by leukapheresis (approximately $5\times10^9$ cells). Whole PBMC were cultured in the presence of anti-CD3 (OKT3) and aldesleukin in order to stimulate T-cell growth according to Example 6. Transduction was initiated by exposure of approximately $10^8$ to $5\times10^8$ cells to supernatant containing the anti-gp100:154-162 TCR retroviral vector. These transduced cells were expanded and tested for their anti-tumor activity. Each culture's growth characteristics and transduction efficiency could not be predicted in advance; some cultures grew better than others, and gene transfer efficiency varied from patient to patient. Successful TCR gene transfer was determined by FACS analysis for the TCR protein and anti-tumor reactivity was tested by cytokine release as measured on peptide pulsed T2 cells. Successful TCR gene transfer for each transduced PBL population was defined as >10% murine TCR positive cells and for biological activity, gamma-interferon secretion must be at least 200 pg/ml. Patients received up to $3\times10^{11}$ anti-gp100:154-162 TCR engineered PBL. A minimum of approximately $5\times10^8$ cells was given. In prior protocols, over $3\times10^{11}$ T cells have been safely infused to cancer patients.

Patients received a nonmyeloablative but lymphocyte depleting preparative regimen consisting of cyclophosphamide and fludarabine followed in one to four days by intravenous infusion of in vitro tumor reactive, TCR gene-transduced PBL plus IV aldesleukin (720,000 IU/kg q8h for a maximum of 15 doses). Approximately 2 hours prior to cell infusion and 14 days later, patients received the subcutaneous (S.C.) injection of ALVAC (2) gp100(M)/MAGE-1,3 minigene/TRICOM (vcP2292). A two week safety assessment period followed regimen completion for each of the first three patients before subsequent patients were accrued in the initial phase of this study.

The protocol for drug administration was as follows:

On Day −7 and −6 at 1 am:

Hydrate: Begin hydration with 0.9% Sodium Chloride Injection containing 10 meq/L of potassium chloride at 2.6 ml/kg/hr (starting 11 hours pre-cyclophosphamide and continue hydration until 24 hours after last cyclophosphamide infusion).

On Day −7 and −6 at 1 am:

(1) Ondansetron (0.15 mg/kg/dose [rounded to the nearest even mg dose between 8 mg and 16 mg based on patient weight] IV every 8 hours×3 days) will be given for nausea.

(2) Furosemide 20 mg iv.

On Day −7 and −6 at 12 pm (Noon):

Cyclophosphamide 60 mg/kg/day×2 days IV in 250 ml D5W with mesna 15 mg/kg/day×2 days over 1 hr. If patient is obese (BMI>35) drug dosage will be calculated using practical weight as described in Table 13.

On Day −7 and −6 at 1 pm:

Begin to monitor potassium level every 12 hours until hydration is stopped. KCl will be adjusted to maintain serum potassium levels in the normal range.

Begin mesna infusion at 3 mg/kg/hour intravenously diluted in a suitable diluent (see pharmaceutical section) over 23 hours after each cyclophosphamide dose. If patient is obese (BMI>35) drug dosage will be calculated.

On Day −5:

Stop IV hydration (24 hours after last cyclophosphamide dose). If urine output <1.5 ml/kg/hr give additional 20 mg furosemide iv. If body weight >2 kg over pre cyclophosphamide value give additional furosemide 20 mg iv.

On Day −5 to Day −1:

Fludarabine 25 mg/m²/day IVPB daily over 30 minutes for 5 days. If patient is obese (BMI>35) drug dosage will be calculated.

Cells prepared as detailed in Example 6 were delivered to the patient care unit by a staff member from the Tumor Immunology Cell Processing Laboratory. Prior to infusion, the cell product identity label was double-checked by two authorized staff (MD or RN), an identification of the product and documentation of administration were entered in the patient's chart, as was done for blood banking protocols. The cells were infused intravenously over 20-30 minutes via non-filtered tubing, gently agitating the bag during infusion to prevent cell clumping.

One to four days after the last does of fludarabine was administered, the following protocol was followed:

On Day 0 (One to Four Days after the Last Dose of Fludarabine):

ALVAC Vaccine: Approximately two hours prior to cell infusion, patients will receive 0.5 ml containing a target dose of $10^7$ $CCID_{50}$ (with a range of approximately $10^{6.4}$ to $10^{7.9}$/mL) of the gp100 ALVAC virus S.C. in each extremity (total of $4\times10^7$ $CCID_{50}/2$ mL). This will be repeated on day 14.

Cells will be infused intravenously (i.v.) on the Patient Care Unit over 20 to 30 minutes (between one and four days after the last dose of fludarabine). Cell infusions will be given as an inpatient.

Aldesleukin 720,000 IU/kg IV (based on total body weight) over 15 minute every eight hours beginning within 24 hours of cell infusion and continuing for up to 5 days (maximum of 15 doses.)

On Day 1-4 (Day 0 is the Day of Cell Infusion):

Start filgrastim at 10 mcg/kg/day daily on Day 1 or 2 subcutaneously until neutrophil count >1.0×10⁹/L×3 days or >5.0×10⁹/L (not to exceed 600 µg/day).

Aldesleukin 720,000 IU/kg IV over 15 minute every eight hours for up to 5 days.

On Day 14:

ALVAC Vaccine: Patients will receive 0.5 ml containing a target dose of $10^7$ $CCID_{50}$ (with a range of approximately $10^{6.4}$ to $10^{7.9}$/mL) of the gp100 ALVAC virus S.C. in each extremity (total of $4\times10^7$ $CCID_{50}/2$ mL).

To prevent infection, the following procedures were followed:

All patients received the fixed combination of trimethoprim and sulfamethoxazole [SMX] as double strength (DS) tab (DS tabs=TMP 160 mg/tab, and SMX 800 mg/tab) P.O. daily three times a week on non-consecutive days, beginning on day −7.

Pentamidine was substituted for TMP/SMX-DS in patients with sulfa allergies. It was administered aerosolized at 300 mg per nebulizer within one week prior to admission and continued monthly thereafter.

Prophylaxis (either SMX/DS or pentamidine) was continued for 6 months post chemotherapy. If the CD4 count was less that 200 at 6 months post chemotherapy, prophylaxis was continued until the CD4 count is greater than 200.

Patients with positive HSV serology were given valacyclovir orally at a dose of 500 mg daily the day after chemotherapy ends, or acyclovir, 250 mg/m² IV q 12 hrs if the patient was not able to take medication by mouth which was continued until absolute neutrophil count is greater than 1000/mm³. Reversible renal insufficiency has been reported with IV but not oral acyclovir. Neurologic toxicity including delirium, tremors, coma, acute psychiatric disturbances, and abnormal EEGs have been reported with higher doses of acyclovir. If this occurred, a dosage adjustment was made or the drug was discontinued. Acyclovir was not used concomitantly with other nucleoside analogs which interfere with DNA synthesis, e.g. ganciclovir. In renal disease, the dose was adjusted as per product labeling.

Patients started Fluconazole 400 mg p.o. the day after chemotherapy concluded and continued until the absolute neutrophil count was greater than 1000/mm³. The drug was given IV at a dose of 400 mg in 0.9% sodium chloride USP daily in patients unable to take it orally.

Patients started on broad-spectrum antibiotics, either a 3$^{rd}$ or 4$^{th}$ generation cephalosporin or a quinolone for fever of 38.3° C. once or two temperatures of 38.0° C. or above at least one hour apart, and an ANC<500/mm³. Aminoglycosides were avoided unless clear evidence of sepsis. Infectious disease consultation was obtained for all patients with unexplained fever or any infectious complications.

Using daily CBC's as a guide, the patient received platelets and packed red blood cells (PRBC's) as needed. Attempts were made to keep Hb>8.0 gm/dl, and plts>20, 000/mm³. All blood products with the exception of the stem cell product were irradiated. Leukocyte filters were utilized for all blood and platelet transfusions to decrease sensitization to transfused WBC's and decrease the risk of CMV infection.

Aldesleukin (based on total body weight) was administered at a dose of 720,000 IU/kg as an intravenous bolus over a 15 minute period every eight hours beginning on the day of cell infusion and continuing for up to 5 days (maximum 15 doses). Doses were skipped depending on patient tolerance. Doses were skipped if patients reach Grade III or IV toxicity due to aldesleukin except for the reversible Grade III toxicities common to aldesleukin such as diarrhea, nausea, vomiting, hypotension, skin changes, anorexia, mucositis, dysphagia, or constitutional symptoms and laboratory changes. Toxicities were managed. If these toxicities were easily reversed within 24 hours by supportive measures then additional doses were given. If greater than 2 doses of aldesleukin were skipped, Aldesleukin administration was stopped. Aldesleukin was administered as an inpatient. Aldesleukin was provided by Novartis Pharmaceuticals Corporation, Florham Park, N.J., if available, and was distributed by the NIH Clinical Pharmacy Department.

The foregoing demonstrates a method of administering to humans the cells of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. An isolated or purified nucleic acid molecule comprising a nucleotide sequence encoding a HLA-A2-restricted, gp100$_{154-162}$-specific murine T Cell Receptor (TCR) comprising an alpha chain polypeptide and a beta chain polypeptide, the nucleic acid molecule comprising a nucleic acid sequence encoding the alpha chain variable region of SEQ ID NO:2 and a nucleic acid sequence encoding the beta chain variable region of SEQ ID NO:3, wherein a functional portion of the variable region of the TCR binds to amino acids 154-162 of a human gp100 protein of SEQ ID NO:1 in the context of an HLA-A2 molecule.

2. The isolated or purified nucleic acid molecule of claim 1, wherein the alpha chain comprises the amino acid sequence of SEQ ID NO: 10 and the beta chain comprises the amino acid sequence of SEQ ID NO: 54 or SEQ ID NO: 11.

3. The isolated or purified nucleic acid molecule of claim 1, wherein the nucleic acid sequence encoding the alpha chain variable region of SEQ ID NO: 2 comprises the nucleotide sequence of SEQ ID NO: 18 and the nucleic acid sequence encoding the beta chain variable region of SEQ ID NO: 3 comprises the nucleotide sequence of SEQ ID NO: 19.

4. The isolated or purified nucleic acid molecule of claim 2, wherein the nucleotide sequence encoding the amino acid sequence of SEQ ID NO: 10 comprises the nucleotide sequence of SEQ ID NO: 26 and the nucleotide sequence encoding the amino acid sequence of SEQ ID NO: 11 comprises the nucleotide sequence of SEQ ID NO: 27.

5. A recombinant expression vector comprising the nucleic acid molecule of claim 1.

6. The recombinant expression vector of claim 5, wherein the vector is a retroviral vector or a lentiviral vector.

7. An isolated host cell comprising the recombinant expression vector of claim 5.

8. The isolated host cell of claim 7, wherein the cell is a peripheral blood lymphocyte (PBL).

9. The isolated host cell of claim 8, wherein the PBL is a CD8$^+$ T cell or a CD4$^+$ T cell.

10. A population of cells comprising at least one host cell of claim 7.

11. A pharmaceutical composition comprising the host cell of claim 7, and a pharmaceutically acceptable carrier.

12. The isolated or purified nucleic acid molecule of claim 1, wherein the alpha chain comprises the amino acid sequence of SEQ ID NO: 10 and the beta chain comprises the amino acid sequence of SEQ ID NO: 11.

13. The recombinant expression vector of claim 5, wherein the alpha chain comprises the amino acid sequence of SEQ ID NO: 10 and the beta chain comprises the amino acid sequence of SEQ ID NO: 11.

14. The isolated host cell of claim 7, wherein the alpha chain comprises the amino acid sequence of SEQ ID NO: 10 and the beta chain comprises the amino acid sequence of SEQ ID NO: 11.

* * * * *

SEQUENCE LISTING

```
<160> NUMBER OF SEQ ID NOS: 57

<210> SEQ ID NO 1
<211> LENGTH: 661
<212> TYPE: PRT
<213> ORGANISM: Homo sapiens
<220> FEATURE:
<221> NAME/KEY: misc_feature
<223> OTHER INFORMATION: amino acid sequence of human gp100 (GenBank
      Accession No. NP_008859)

<400> SEQUENCE: 1

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125
```

```
Ala Cys Ile Phe Pro Asp Gly Gly Pro Cys Pro Ser Gly Ser Trp Ser
            130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
                355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
                420                 425                 430

Ile Pro Glu Pro Glu Gly Pro Asp Ala Ser Ser Ile Met Ser Thr Glu
                435                 440                 445

Ser Ile Thr Gly Ser Leu Gly Pro Leu Leu Asp Gly Thr Ala Thr Leu
                450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
                515                 520                 525

Ser Ser Pro Gly Cys Gln Pro Pro Ala Gln Arg Leu Cys Gln Pro Val
530                 535                 540
```

-continued

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Leu Met Lys Gln Asp
    610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 2
<211> LENGTH: 111
<212> TYPE: PRT
<213> ORGANISM: Mus musculus
<220> FEATURE:
<221> NAME/KEY: misc_feature
<223> OTHER INFORMATION: amino acid sequence of variable region of
      alpha chain of Sp(0.01)A TCR

<400> SEQUENCE: 2

Gln Gln Lys Val Gln Gln Ser Pro Glu Ser Leu Ile Val Pro Glu Gly
1               5                   10                  15

Ala Met Thr Ser Leu Asn Cys Thr Phe Ser Asp Ser Ala Ser Gln Tyr
            20                  25                  30

Phe Ala Trp Tyr Arg Gln His Ser Gly Lys Ala Pro Lys Ala Leu Met
        35                  40                  45

Ser Ile Phe Ser Asn Gly Glu Lys Glu Glu Gly Arg Phe Thr Ile His
    50                  55                  60

Leu Asn Lys Ala Ser Leu His Phe Ser Leu His Ile Arg Asp Ser Gln
65                  70                  75                  80

Pro Ser Asp Ser Ala Leu Tyr Leu Cys Ala Ala Asn Asn Tyr Ala Gln
                85                  90                  95

Gly Leu Thr Phe Gly Leu Gly Thr Arg Val Ser Val Phe Pro Tyr
            100                 105                 110

<210> SEQ ID NO 3
<211> LENGTH: 112
<212> TYPE: PRT
<213> ORGANISM: Mus musculus
<220> FEATURE:
<221> NAME/KEY: misc_feature
<223> OTHER INFORMATION: amino acid sequence of variable region of
      beta chain of Sp(0.01)A TCR

<400> SEQUENCE: 3

Glu Ala Ala Val Thr Gln Ser Pro Arg Ser Lys Val Ala Val Thr Gly
1               5                   10                  15

Gly Lys Val Thr Leu Ser Cys His Gln Thr Asn Asn His Asp Tyr Met
            20                  25                  30

Tyr Trp Tyr Arg Gln Asp Thr Gly His Gly Leu Arg Leu Ile His Tyr
        35                  40                  45

Ser Tyr Val Ala Asp Ser Thr Glu Lys Gly Asp Ile Pro Asp Gly Tyr

```
                50                  55                  60
Lys Ala Ser Arg Pro Ser Gln Glu Asn Phe Ser Leu Ile Leu Glu Leu
 65                  70                  75                  80

Ala Ser Leu Ser Gln Thr Ala Val Tyr Phe Cys Ala Ser Ser Pro Gly
                 85                  90                  95

Gly Gly Gly Glu Gln Tyr Phe Gly Pro Gly Thr Arg Leu Thr Val Leu
                100                 105                 110
```

<210> SEQ ID NO 4
<211> LENGTH: 116
<212> TYPE: PRT
<213> ORGANISM: Mus musculus
<220> FEATURE:
<221> NAME/KEY: misc_feature
<223> OTHER INFORMATION: amino acid sequence of variable region of
      alpha chain of T2(1)B

<400> SEQUENCE: 4

```
Glu Ser His Gly Glu Lys Val Glu Gln His Glu Ser Thr Leu Ser Val
 1               5                  10                  15

Arg Glu Gly Asp Ser Ala Val Ile Asn Cys Thr Tyr Thr Asp Thr Ala
                20                  25                  30

Ser Ser Tyr Phe Pro Trp Tyr Lys Gln Glu Ala Gly Lys Ser Leu His
                35                  40                  45

Phe Val Ile Asp Ile Arg Ser Asn Val Asp Arg Lys Gln Ser Gln Arg
 50                  55                  60

Leu Ile Val Leu Leu Asp Lys Lys Ala Lys Arg Phe Ser Leu His Ile
 65                  70                  75                  80

Thr Ala Thr Gln Pro Glu Asp Ser Ala Ile Tyr Phe Cys Ala Ala Ser
                 85                  90                  95

Ser Asp Ser Asn Tyr Gln Leu Ile Trp Gly Ser Gly Thr Lys Leu Ile
                100                 105                 110

Ile Lys Pro Asp
        115
```

<210> SEQ ID NO 5
<211> LENGTH: 98
<212> TYPE: PRT
<213> ORGANISM: Mus musculus
<220> FEATURE:
<221> NAME/KEY: misc_feature
<223> OTHER INFORMATION: amino acid sequence of variable region of
      beta chain of T2(1)B

<400> SEQUENCE: 5

```
Asn Ser Gly Val Val Gln Ser Pro Arg Tyr Ile Ile Lys Gly Lys Gly
 1               5                  10                  15

Glu Arg Ser Ile Leu Lys Cys Ile Pro Ile Ser Gly His Leu Ser Val
                20                  25                  30

Ala Trp Tyr Gln Gln Thr Gln Gly Gln Glu Leu Lys Phe Phe Ile Gln
                35                  40                  45

His Tyr Asp Lys Met Glu Arg Asp Lys Gly Asn Leu Pro Ser Arg Phe
 50                  55                  60

Ser Val Gln Gln Phe Asp Asp Tyr His Ser Glu Met Asn Met Ser Ala
 65                  70                  75                  80

Leu Glu Leu Glu Asp Ser Ala Val Tyr Phe Cys Ala Ser Ser Leu Ser
                 85                  90                  95

Gly Ala
```

```
<210> SEQ ID NO 6
<211> LENGTH: 114
<212> TYPE: PRT
<213> ORGANISM: Mus musculus
<220> FEATURE:
<221> NAME/KEY: misc_feature
<223> OTHER INFORMATION: amino acid sequence of variable region of
      alpha chain of Sp(0.1)A10

<400> SEQUENCE: 6

Ala Gln Ser Val Thr Gln Pro Asp Ala Arg Val Thr Val Ser Glu Gly
1               5                  10                  15

Ala Ser Leu Gln Leu Arg Cys Lys Tyr Ser Tyr Ser Ala Thr Pro Tyr
            20                  25                  30

Leu Phe Trp Tyr Val Gln Tyr Pro Arg Gln Gly Leu Gln Leu Leu Leu
        35                  40                  45

Lys Tyr Tyr Ser Gly Asp Pro Val Val Gln Gly Val Asn Ser Phe Glu
    50                  55                  60

Ala Glu Phe Ser Lys Ser Asn Ser Ser Phe His Leu Gln Lys Ala Ser
65                  70                  75                  80

Val His Trp Ser Asp Ser Ala Val Tyr Phe Cys Ala Leu Ser His Asp
                85                  90                  95

Ser Asn Tyr Gln Leu Ile Trp Gly Ser Gly Thr Lys Leu Ile Ile Lys
            100                 105                 110

Pro Asp

<210> SEQ ID NO 7
<211> LENGTH: 114
<212> TYPE: PRT
<213> ORGANISM: Mus musculus
<220> FEATURE:
<221> NAME/KEY: misc_feature
<223> OTHER INFORMATION: amino acid sequence of variable region of
      beta chain of Sp(0.1)A10

<400> SEQUENCE: 7

Asn Ser Gly Val Val Gln Ser Pro Arg Tyr Ile Ile Lys Gly Lys Gly
1               5                  10                  15

Glu Arg Ser Ile Leu Lys Cys Ile Pro Ile Ser Gly Tyr Leu Ser Val
            20                  25                  30

Ala Trp Tyr Gln Gln Thr Gln Gly Gln Glu Leu Lys Phe Phe Ile Gln
        35                  40                  45

His Tyr Asp Lys Met Glu Arg Asp Lys Gly Asn Leu Pro Ser Arg Phe
    50                  55                  60

Ser Val Gln Gln Phe Asp Asp Tyr His Ser Glu Met Asn Met Ser Ala
65                  70                  75                  80

Leu Glu Leu Glu Asp Ser Ala Val Tyr Phe Cys Ala Ser Ser Leu Ala
                85                  90                  95

Gly Val Asn Tyr Ala Glu Gln Phe Phe Gly Pro Gly Thr Arg Leu Thr
            100                 105                 110

Val Leu

<210> SEQ ID NO 8
<211> LENGTH: 116
<212> TYPE: PRT
<213> ORGANISM: Mus musculus
<220> FEATURE:
<221> NAME/KEY: misc_feature
<223> OTHER INFORMATION: amino acid sequence of the variable region
      of the alpha chain of T2(1)C
```

-continued

<400> SEQUENCE: 8

Glu Ser His Gly Glu Lys Val Glu Gln His Glu Ser Thr Leu Ser Val
1               5                   10                  15

Arg Glu Gly Asp Ser Ala Val Ile Asn Cys Thr Tyr Thr Asp Thr Ala
            20                  25                  30

Ser Ser Tyr Phe Pro Trp Tyr Lys Gln Glu Ala Gly Lys Ser Leu His
        35                  40                  45

Phe Val Ile Asp Ile Arg Ser Asn Val Asp Arg Lys Gln Ser Gln Arg
50                  55                  60

Leu Ile Val Leu Leu Asp Lys Lys Ala Lys Arg Phe Ser Leu His Ile
65                  70                  75                  80

Thr Ala Thr Gln Pro Glu Asp Ser Ala Ile Tyr Phe Cys Ala Ala Ser
                85                  90                  95

Ser Asp Ser Asn Tyr Gln Leu Ile Trp Gly Ser Gly Thr Lys Leu Ile
            100                 105                 110

Ile Lys Pro Asp
        115

<210> SEQ ID NO 9
<211> LENGTH: 114
<212> TYPE: PRT
<213> ORGANISM: Mus musculus
<220> FEATURE:
<221> NAME/KEY: misc_feature
<223> OTHER INFORMATION: amino acid sequence of the variable region of
      the beta chain of T2(1)C

<400> SEQUENCE: 9

Asn Ser Gly Val Val Gln Ser Pro Arg Tyr Ile Ile Lys Gly Lys Gly
1               5                   10                  15

Lys Arg Ser Ile Leu Lys Cys Ile Pro Ile Ser Gly His Leu Ser Val
            20                  25                  30

Ala Trp Tyr Gln Gln Thr Gln Gly Gln Glu Leu Lys Phe Phe Ile Gln
        35                  40                  45

His Tyr Asp Lys Met Glu Arg Asp Lys Gly Asn Leu Pro Ser Arg Phe
50                  55                  60

Ser Val Gln Gln Phe Asp Asp Tyr His Ser Glu Met Asn Met Ser Ala
65                  70                  75                  80

Leu Glu Leu Glu Asp Ser Ala Val Tyr Phe Cys Ala Ser Ser Leu Ser
                85                  90                  95

Gly Ala Asn Tyr Ala Glu Gln Phe Phe Gly Pro Gly Thr Arg Leu Thr
            100                 105                 110

Val Leu

<210> SEQ ID NO 10
<211> LENGTH: 267
<212> TYPE: PRT
<213> ORGANISM: Mus musculus
<220> FEATURE:
<221> NAME/KEY: misc_feature
<223> OTHER INFORMATION: amino acid sequence of alpha chain of
      Sp(0.01)A TCR

<400> SEQUENCE: 10

Met Lys Ser Leu Ser Val Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

```
Val Pro Glu Gly Ala Met Thr Ser Leu Asn Cys Thr Phe Ser Asp Ser
        35                  40                  45

Ala Ser Gln Tyr Phe Ala Trp Tyr Arg Gln His Ser Gly Lys Ala Pro
    50                  55                  60

Lys Ala Leu Met Ser Ile Phe Ser Asn Gly Lys Glu Glu Gly Arg
65                  70                  75                  80

Phe Thr Ile His Leu Asn Lys Ala Ser Leu His Phe Ser Leu His Ile
                85                  90                  95

Arg Asp Ser Gln Pro Ser Asp Ser Ala Leu Tyr Leu Cys Ala Ala Asn
                100                 105                 110

Asn Tyr Ala Gln Gly Leu Thr Phe Gly Leu Gly Thr Arg Val Ser Val
            115                 120                 125

Phe Pro Tyr Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 11
<211> LENGTH: 303
<212> TYPE: PRT
<213> ORGANISM: Mus musculus
<220> FEATURE:
<221> NAME/KEY: misc_feature
<223> OTHER INFORMATION: amino acid sequence of beta chain of
      Sp(0.01)A TCR

<400> SEQUENCE: 11

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
            20                  25                  30

Thr Gly Gly Lys Val Thr Leu Ser Cys His Gln Thr Asn Asn His Asp
        35                  40                  45

Tyr Met Tyr Trp Tyr Arg Gln Asp Thr Gly His Gly Leu Arg Leu Ile
    50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Ser Leu Ser Gln Thr Ala Val Tyr Phe Cys Ala Ser Ser
            100                 105                 110
```

```
Pro Gly Gly Gly Gly Glu Gln Tyr Phe Gly Pro Gly Thr Arg Leu Thr
            115                 120                 125

Val Leu Glu Asp Leu Arg Asn Val Thr Pro Pro Lys Val Ser Leu Phe
    130                 135                 140

Glu Pro Ser Lys Ala Glu Ile Ala Asn Lys Arg Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr Gln Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Thr Leu Val Val Met Ala Met Val Lys Arg Lys Asn Ser
    290                 295                 300

<210> SEQ ID NO 12
<211> LENGTH: 271
<212> TYPE: PRT
<213> ORGANISM: Mus musculus
<220> FEATURE:
<221> NAME/KEY: misc_feature
<223> OTHER INFORMATION: amino acid sequence of alpha chain of T2(1)B

<400> SEQUENCE: 12

Met Met Lys Thr Ser Leu His Thr Val Phe Leu Phe Leu Trp Leu Trp
1               5                   10                  15

Met Asp Trp Glu Ser His Gly Glu Lys Val Glu Gln His Glu Ser Thr
            20                  25                  30

Leu Ser Val Arg Glu Gly Asp Ser Ala Val Ile Asn Cys Thr Tyr Thr
        35                  40                  45

Asp Thr Ala Ser Ser Tyr Phe Pro Trp Tyr Lys Gln Glu Ala Gly Lys
    50                  55                  60

Ser Leu His Phe Val Ile Asp Ile Arg Ser Asn Val Asp Arg Lys Gln
65                  70                  75                  80

Ser Gln Arg Leu Ile Val Leu Leu Asp Lys Lys Ala Lys Arg Phe Ser
                85                  90                  95

Leu His Ile Thr Ala Thr Gln Pro Glu Asp Ser Ala Ile Tyr Phe Cys
            100                 105                 110

Ala Ala Ser Ser Asp Ser Asn Tyr Gln Leu Ile Trp Gly Ser Gly Thr
        115                 120                 125

Lys Leu Ile Ile Lys Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175
```

```
Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
            210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 13
<211> LENGTH: 316
<212> TYPE: PRT
<213> ORGANISM: Mus musculus
<220> FEATURE:
<221> NAME/KEY: misc_feature
<223> OTHER INFORMATION: amino acid sequence of beta chain of T2(1)B

<400> SEQUENCE: 13

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
            20                  25                  30

Val Val Gln Ser Pro Arg Tyr Ile Ile Lys Gly Lys Gly Glu Arg Ser
            35                  40                  45

Ile Leu Lys Cys Ile Pro Ile Ser Gly His Leu Ser Val Ala Trp Tyr
        50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Ser Gly Ala Asn
            115                 120                 125

Tyr Ala Glu Gln Phe Phe Gly Pro Gly Thr Arg Leu Thr Val Leu Glu
        130                 135                 140

Asp Leu Arg Asn Val Thr Pro Pro Lys Val Ser Leu Phe Glu Pro Ser
145                 150                 155                 160

Lys Ala Glu Ile Ala Asn Lys Gln Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Ser Thr Asp Pro Gln Ala Tyr Lys Glu
            195                 200                 205

Ser Asn Tyr Ser Tyr Cys Leu Ser Ser Arg Leu Arg Val Ser Ala Thr
        210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Asn Ile Ser Ala Glu Ala Trp Gly Arg Ala Asp Cys Gly Ile
```

```
                        260                 265                 270

Thr Ser Ala Ser Tyr Gln Gln Gly Val Leu Ser Ala Thr Ile Leu Tyr
                275                 280                 285

Glu Ile Leu Leu Gly Lys Ala Thr Leu Tyr Ala Val Leu Val Ser Thr
            290                 295                 300

Leu Val Val Met Ala Met Val Lys Arg Lys Asn Ser
305                 310                 315

<210> SEQ ID NO 14
<211> LENGTH: 269
<212> TYPE: PRT
<213> ORGANISM: Mus musculus
<220> FEATURE:
<221> NAME/KEY: misc_feature
<223> OTHER INFORMATION: amino acid sequence of the alpha chain of TCR
      of clone Sp(0.1)A10

<400> SEQUENCE: 14

Met Leu Leu Ala Leu Leu Pro Val Gly Ile His Phe Val Leu Arg
1               5                   10                  15

Asp Ala Gln Ala Gln Ser Val Thr Gln Pro Asp Ala Arg Val Thr Val
            20                  25                  30

Ser Glu Gly Ala Ser Leu Gln Leu Arg Cys Lys Tyr Ser Tyr Ser Ala
        35                  40                  45

Thr Pro Tyr Leu Phe Trp Tyr Val Gln Tyr Pro Arg Gln Gly Leu Gln
    50                  55                  60

Leu Leu Leu Lys Tyr Tyr Ser Gly Asp Pro Val Val Gln Gly Val Asn
65                  70                  75                  80

Ser Phe Glu Ala Glu Phe Ser Lys Ser Asn Ser Ser Phe His Leu Gln
                85                  90                  95

Lys Ala Ser Val His Trp Ser Asp Ser Ala Val Tyr Phe Cys Ala Leu
            100                 105                 110

Ser His Asp Ser Asn Tyr Gln Leu Ile Trp Gly Ser Gly Thr Lys Leu
        115                 120                 125

Ile Ile Lys Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 15
<211> LENGTH: 316
<212> TYPE: PRT
<213> ORGANISM: Mus musculus
```

-continued

<220> FEATURE:
<221> NAME/KEY: misc_feature
<223> OTHER INFORMATION: amino acid sequence of beta chain of TCR of
      clone Sp(0.1)A10

<400> SEQUENCE: 15

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
            20                  25                  30

Val Val Gln Ser Pro Arg Tyr Ile Ile Lys Gly Lys Gly Glu Arg Ser
        35                  40                  45

Ile Leu Lys Cys Ile Pro Ile Ser Gly Tyr Leu Ser Val Ala Trp Tyr
    50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Ala Gly Val Asn
        115                 120                 125

Tyr Ala Glu Gln Phe Phe Gly Pro Gly Thr Arg Leu Thr Val Leu Glu
    130                 135                 140

Asp Leu Arg Asn Val Thr Pro Pro Lys Val Ser Leu Phe Glu Pro Ser
145                 150                 155                 160

Lys Ala Glu Ile Ala Asn Lys Gln Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Ser Thr Asp Pro Gln Ala Tyr Lys Glu
        195                 200                 205

Ser Asn Tyr Ser Tyr Cys Leu Ser Ser Arg Leu Arg Val Ser Ala Thr
    210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Asn Ile Ser Ala Glu Ala Trp Gly Arg Ala Asp Cys Gly Ile
            260                 265                 270

Thr Ser Ala Ser Tyr Gln Gln Gly Val Leu Ser Ala Thr Ile Leu Tyr
        275                 280                 285

Glu Ile Leu Leu Gly Lys Ala Thr Leu Tyr Ala Val Leu Val Ser Thr
    290                 295                 300

Leu Val Val Met Ala Met Val Lys Arg Lys Asn Ser
305                 310                 315

<210> SEQ ID NO 16
<211> LENGTH: 271
<212> TYPE: PRT
<213> ORGANISM: Mus musculus
<220> FEATURE:
<221> NAME/KEY: misc_feature
<223> OTHER INFORMATION: amino acid sequence of alpha chain of TCR
      from clone T2(1)C

<400> SEQUENCE: 16

```
Met Met Lys Thr Ser Leu His Thr Val Phe Leu Phe Leu Trp Leu Trp
1               5                   10                  15

Met Asp Trp Glu Ser His Gly Glu Lys Val Glu Gln His Glu Ser Thr
            20                  25                  30

Leu Ser Val Arg Glu Gly Asp Ser Ala Val Ile Asn Cys Thr Tyr Thr
                35                  40                  45

Asp Thr Ala Ser Ser Tyr Phe Pro Trp Tyr Lys Gln Glu Ala Gly Lys
        50                  55                  60

Ser Leu His Phe Val Ile Asp Ile Arg Ser Asn Val Asp Arg Lys Gln
65                  70                  75                  80

Ser Gln Arg Leu Ile Val Leu Leu Asp Lys Lys Ala Lys Arg Phe Ser
                85                  90                  95

Leu His Ile Thr Ala Thr Gln Pro Glu Asp Ser Ala Ile Tyr Phe Cys
                100                 105                 110

Ala Ala Ser Ser Asp Ser Asn Tyr Gln Leu Ile Trp Gly Ser Gly Thr
            115                 120                 125

Lys Leu Ile Ile Lys Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 17
<211> LENGTH: 316
<212> TYPE: PRT
<213> ORGANISM: Mus musculus
<220> FEATURE:
<221> NAME/KEY: misc_feature
<223> OTHER INFORMATION: amino acid sequence of the beta chain of
      TCR from clone T2(1)C

<400> SEQUENCE: 17

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
                20                  25                  30

Val Val Gln Ser Pro Arg Tyr Ile Ile Lys Gly Lys Gly Lys Arg Ser
            35                  40                  45

Ile Leu Lys Cys Ile Pro Ile Ser Gly His Leu Ser Val Ala Trp Tyr
    50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
```

```
                    85                  90                  95
Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Ser Gly Ala Asn
            115                 120                 125

Tyr Ala Glu Gln Phe Phe Gly Pro Gly Thr Arg Leu Thr Val Leu Glu
            130                 135                 140

Asp Leu Arg Asn Val Thr Pro Pro Lys Val Ser Leu Phe Glu Pro Ser
145                 150                 155                 160

Lys Ala Glu Ile Ala Asn Lys Arg Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Ser Thr Asp Pro Gln Ala Tyr Lys Glu
            195                 200                 205

Ser Asn Tyr Ser Tyr Cys Leu Ser Ser Cys Leu Arg Val Ser Ala Thr
210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Asp Ile Ser Ala Glu Ala Trp Gly Arg Ala Asp Cys Gly Ile
            260                 265                 270

Thr Ser Ala Ser Tyr Gln Gln Gly Val Leu Ser Ala Thr Ile Leu Tyr
            275                 280                 285

Glu Ile Leu Leu Gly Lys Ala Thr Leu Tyr Ala Val Leu Val Ser Thr
            290                 295                 300

Leu Val Val Met Ala Met Val Lys Arg Lys Asn Ser
305                 310                 315

<210> SEQ ID NO 18
<211> LENGTH: 333
<212> TYPE: DNA
<213> ORGANISM: Mus musculus
<220> FEATURE:
<221> NAME/KEY: misc_feature
<223> OTHER INFORMATION: nucleotide sequence of variable region of
      alpha chain of Sp(0.01)A TCR

<400> SEQUENCE: 18
cagcagaagg tgcagcagag cccagaatcc ctcattgtcc cagagggagc catgaccct      60 ctcaactgca ctttcagcga cagtgcttct cagtattttg catggtacag acagcattct    120
gggaaagccc ccaaggcact gatgtccatc ttctccaatg gtgaaaaaga agaaggcaga    180
ttcacaattc acctcaataa agccagtctg catttctcgc tacacatcag agactcccag    240
cccagtgact ctgctctcta cctctgtgca gccaataact atgcccaggg attaaccttc    300
ggtcttggca ccagagtatc tgtgtttccc tac                                 333

<210> SEQ ID NO 19
<211> LENGTH: 336
<212> TYPE: DNA
<213> ORGANISM: Mus musculus
<220> FEATURE:
<221> NAME/KEY: misc_feature
<223> OTHER INFORMATION: nucleotide sequence of variable region of
      beta chain of Sp(0.01)A TCR

<400> SEQUENCE: 19
```

```
gaggctgcag tcacccaaag tccaagaagc aaggtggcag taacaggagg aaaggtgaca      60
ttgagctgtc accagactaa taaccatgac tatatgtact ggtatcggca ggacacgggg     120
catgggctga ggctgatcca ttactcatat gtcgctgaca gcacggagaa aggagatatc     180
cctgatgggt acaaggcctc cagaccaagc caagagaatt tctctctcat tctggagttg     240
gcttcccttt ctcagacagc tgtatatttc tgtgccagca gccctggggg ggggggggaa     300
cagtacttcg gtcccggcac caggctcacg gtttta                              336
```

<210> SEQ ID NO 20
<211> LENGTH: 349
<212> TYPE: DNA
<213> ORGANISM: Mus musculus
<220> FEATURE:
<221> NAME/KEY: misc_feature
<223> OTHER INFORMATION: nucleotide sequence of variable region of
      alpha chain of T2(1)B

<400> SEQUENCE: 20

```
ggagagccat ggagagaagg tcgagcaaca tgagtctaca ctgagtgttc gagagggaga      60
cagcgctgtc atcaactgca cttacacaga tactgcttca tcatacttcc cttggtacaa     120
gcaagaagct ggaaagagtc tccactttgt gatagacatt cgttcaaatg tggacagaaa     180
acagagccaa agacttatag ttttgttgga taagaaagcc aaacgattct ccctgcacat     240
cacagccaca cagcctgaag attcagccat ctacttctgt gcagcaagct cggatagcaa     300
ctatcagttg atctggggct ctgggaccaa gctaattata aagccagac                 349
```

<210> SEQ ID NO 21
<211> LENGTH: 342
<212> TYPE: DNA
<213> ORGANISM: Mus musculus
<220> FEATURE:
<221> NAME/KEY: misc_feature
<223> OTHER INFORMATION: nucleotide sequence of variable region of
      beta chain of T2(1)B

<400> SEQUENCE: 21

```
aattctgggg ttgtccagtc tccaagatac ataatcaaag gaaagggaga aaggtccatt      60
ctaaaatgta ttcccatctc tggacatctc tctgtggcct ggtatcaaca gactcagggg     120
caggaactaa agttcttcat tcagcattat gataaaatgg agagagataa aggaaacctg     180
cccagcagat tctcagtcca acagtttgat gactatcact ctgagatgaa catgagtgcc     240
ttggagctag aggactctgc cgtgtacttc tgtgccagct ctctttctgg ggcgaactat     300
gctgagcagt tcttcggacc agggacacga ctcaccgtcc ta                       342
```

<210> SEQ ID NO 22
<211> LENGTH: 342
<212> TYPE: DNA
<213> ORGANISM: Mus musculus
<220> FEATURE:
<221> NAME/KEY: misc_feature
<223> OTHER INFORMATION: nucleotide sequence of variable region of
      alpha chain of Sp(0.1)A10

<400> SEQUENCE: 22

```
gctcagtcag tgacacagcc cgatgctcgc gtcactgtct ctgaaggagc ctctctgcag      60
ctgagatgca agtattccta ctctgcgaca ccttatctgt tctggtatgt ccagtacccg     120
cggcaggggc tgcagctgct cctcaagtac tattcaggag acccagtggt tcaaggagtg     180
```
aacagcttcg aggctgagtt cagcaagagt aactcttcct tccacctgca gaaagcctct        240
gtgcactgga gcgactcggc tgtgtacttc tgtgctctga ccacgatag caactatcag        300 ttgatctggg gctctgggac caagctaatt ataaagccag ac                          342

<210> SEQ ID NO 23
<211> LENGTH: 342
<212> TYPE: DNA
<213> ORGANISM: Mus musculus
<220> FEATURE:
<221> NAME/KEY: misc_feature
<223> OTHER INFORMATION: nucleotide sequence of variable region of
      beta chain of Sp(0.1)A10

<400> SEQUENCE: 23
aattctgggg ttgtccagtc tccaagatac ataatcaaag gaaagggaga aaggtccatt        60
ctaaaatgta ttcccatctc tggatatctc tctgtggcct ggtatcaaca gactcagggg        120
caggaactaa agttcttcat tcagcattat gataaaatgg agagagataa aggaaacctg        180
cccagcagat tctcagtcca acagtttgat gactatcact ctgagatgaa catgagtgcc        240
ttggagctag aggactctgc cgtgtacttc tgtgccagct ctctcgcggg ggttaactat        300
gctgagcagt tcttcggacc agggacacga ctcaccgtcc ta                          342

<210> SEQ ID NO 24
<211> LENGTH: 698
<212> TYPE: DNA
<213> ORGANISM: Mus musculus
<220> FEATURE:
<221> NAME/KEY: misc_feature
<223> OTHER INFORMATION: nucleotide sequence of variable region of
      alpha chain of T2(1)C

<400> SEQUENCE: 24
ggagagccat ggagagaagg tcgagcaaca tgagtctaca ctgagtgttc gagagggaga        60
cagcgctgtc atcaactgca cttacacaga tactgcttca tcatacttcc cttggtacaa        120
gcaagaagct ggaaagagtc tccactttgt gatagacatt cgttcaaatg tggacagaaa        180
acagagccaa agacttatag ttttgttgga taagaaagcc aaacgattct ccctgcacat        240
cacagccaca cagcctgaag attcagccat ctacttctgt gcagcaagct cggatagcaa        300
ctatcagttg atctggggct ctgggaccaa gctaattata aagccagacg agagccatg        360 gagagaaggt cgagcaacat gagtctacac tgagtgttcg agagggagac agcgctgtca        420
tcaactgcac ttacacagat actgcttcat catacttccc ttggtacaag caagaagctg        480
gaaagagtct ccactttgtg atagacattc gttcaaatgt ggacagaaaa cagagccaaa        540
gacttatagt tttgttggat aagaaagcca aacgattctc cctgcacatc acagccacac        600
agcctgaaga ttcagccatc tacttctgtg cagcaagctc ggatagcaac tatcagttga        660
tctggggctc tgggaccaag ctaattataa agccagac                               698

<210> SEQ ID NO 25
<211> LENGTH: 342
<212> TYPE: DNA
<213> ORGANISM: Mus musculus
<220> FEATURE:
<221> NAME/KEY: misc_feature
<223> OTHER INFORMATION: nucleotide sequence of variable region of
      beta chain of T2(1)C

<400> SEQUENCE: 25
aattctgggg ttgtccagtc tccaagatac ataatcaaag gaaagggaaa aaggtccatt        60

```
ctaaaatgta ttcccatctc tggacatctc tctgtggcct ggtatcaaca gactcagggg      120
caggaactaa agttcttcat tcagcattat gataaaatgg agagagataa aggaaacctg      180
cccagcagat tctcagtcca acagtttgat gactatcact ctgagatgaa catgagtgcc      240
ttggagctag aggactctgc cgtgtacttc tgtgccagct ctctttctgg ggcgaactat      300
gctgagcagt tcttcggacc agggacacga ctcaccgtcc ta                        342
```

<210> SEQ ID NO 26
<211> LENGTH: 804
<212> TYPE: DNA
<213> ORGANISM: Mus musculus
<220> FEATURE:
<221> NAME/KEY: misc_feature
<223> OTHER INFORMATION: cDNA of alpha chain of Sp(0.01)A TCR

<400> SEQUENCE: 26

```
atgaaatcct tgagtgtttc cctagtggtc ctgtggctcc agttaaactg ggtgaacagc       60
cagcagaagg tgcagcagag cccagaatcc ctcattgtcc cagagggagc catgacctct      120
ctcaactgca cttttcagcga cagtgcttct cagtattttg catggtacag acagcattct      180
gggaaagccc ccaaggcact gatgtccatc ttctccaatg tgaaaaaga agaaggcaga      240 ttcacaattc acctcaataa agccagtctg catttctcgc tacacatcag agactcccag      300
cccagtgact ctgctctcta cctctgtgca gccaataact atgcccaggg attaaccttc      360
ggtcttggca ccagagtatc tgtgtttccc tacatccaga acccagaacc tgctgtgtac      420
cagttaaaag atcctcggtc tcaggacagc accctctgcc tgttcaccga ctttgactcc      480
caaatcaatg tgccgaaaac catggaatct ggaacgttca tcactgacaa aactgtgctg      540
gacatgaaag ctatggattc caagagcaat gggccattg cctggagcaa ccagacaagc      600
ttcacctgcc aagatatctt caaagagacc aacgccacct accccagttc agacgttccc      660
tgtgatgcca cgttgactga aaaagctttt gaaacagata tgaacctaaa cttttcaaaac      720 ctgtcagtta tgggactccg aatcctcctg ctgaaagtag ccggatttaa cctgctcatg      780
acgctgaggc tgtggtccag ttga                                             804
```

<210> SEQ ID NO 27
<211> LENGTH: 912
<212> TYPE: DNA
<213> ORGANISM: Mus musculus
<220> FEATURE:
<221> NAME/KEY: misc_feature
<223> OTHER INFORMATION: cDNA of beta chain of Sp(0.01)A TCR

<400> SEQUENCE: 27

```
atgggctcca gactcttctt tgtggttttg attctcctgt gtgcaaaaca catggaggct       60
gcagtcaccc aaagtccaag aagcaaggtg gcagtaacag aggaaaggt gacattgagc      120 tgtcaccaga ctaataacca tgactatatg tactggtatc ggcaggacac ggggcatggg      180
ctgaggctga tccattactc atatgtcgct gacagcacgg agaaaggaga tatccctgat      240
gggtacaagg cctccagacc aagccaagag aatttctctc tcattctgga gttggcttcc      300 cttttctcaga cagctgtata tttctgtgcc agcagccctg gggggggggg ggaacagtac      360
ttcggtcccg gcaccaggct cacggtttta gaggatctga gaatgtgac tccacccaag      420 gtctccttgt ttgagccatc aaaagcagag attgcaaaca acgaaaggc tacccctcgtg      480 tgcttggcca ggggcttctt ccctgaccac gtggagctga gctggtgggt gaatggcaag      540
```

```
gaggtccaca gtgggtcag cacggaccct caggcctaca aggagagcaa ttatagctac    600
tgcctgagca gccgcctgag ggtctctgct accttctggc acaatcctcg aaaccacttc    660
cgctgccaag tgcagttcca tgggctttca gaggaggaca agtggccaga gggctcaccc    720
aaacctgtca cacagaacat cagtgcagag gcctggggcc gagcagactg tgggattacc    780
tcagcatcct atcaacaagg ggtcttgtct gccaccatcc tctatgagat cctgctaggg    840
aaagccaccc tgtatgctgt gcttgtcagt acactggtgg tgatggctat ggtcaaaaga    900
aagaattcat ga                                                        912
```

```
<210> SEQ ID NO 28
<211> LENGTH: 816
<212> TYPE: DNA
<213> ORGANISM: Mus musculus
<220> FEATURE:
<221> NAME/KEY: misc_feature
<223> OTHER INFORMATION: nucleotide sequence encoding the alpha chain
      of the TCR from clone T2(1) B

<400> SEQUENCE: 28
atgatgaaga catcccttca cactgtattc ctattcttgt ggctatggat ggactgggag     60
agccatggag agaaggtcga gcaacatgag tctacactga gtgttcgaga gggagacagc    120
gctgtcatca actgcactta cacagatact gcttcatcat acttcccttg gtacaagcaa    180
gaagctggaa agagtctcca ctttgtgata gacattcgtt caaatgtgga cagaaaacag    240
agccaaagac ttatagtttt gttggataag aaagccaaac gattctccct gcacatcaca    300
gccacacagc ctgaagattc agccatctac ttctgtgcag caagctcgga tagcaactat    360
cagttgatct ggggctctgg gaccaagcta attataaagc cagacatcca gaacccagaa    420
cctgctgtgt accagttaaa agatcctcgg tctcaggaca gcaccctctg cctgttcacc    480
gactttgact cccaaatcaa tgtgccgaaa accatggaat ctggaacgtt catcactgac    540
aaaactgtgc tggacatgaa agctatggat tccaagagca tggggccat tgcctggagc    600 aaccagacaa gcttcacctg ccaagatatc ttcaaagaga ccaacgccac ctaccccagt    660
tcagacgttc cctgtgatgc cacgttgact gagaaaagct ttgaaacaga tatgaaccta    720
aactttcaaa acctgtcagt tatgggactc cgaatcctcc tgctgaaagt agccggattt    780
aacctgctca tgacgctgag gctgtggtcc agttga                              816
```

```
<210> SEQ ID NO 29
<211> LENGTH: 951
<212> TYPE: DNA
<213> ORGANISM: Mus musculus
<220> FEATURE:
<221> NAME/KEY: misc_feature
<223> OTHER INFORMATION: nucleotide sequence encoding the beta chain
      of the TCR from clone T2(1) B

<400> SEQUENCE: 29
atgtctaaca ctgccttccc tgaccccgcc tggaacacca ccctgctatc ttgggttgct     60
ctctttctcc tgggaacaag ttcagcaaat tctggggttg tccagtctcc aagatacata    120
atcaaaggaa agggagaaag gtccattcta aaatgtattc ccatctctgg acatctctct    180
gtggcctggt atcaacagac tcaggggcag gaactaaagt tcttcattca gcattatgat    240
aaaatggaga gagataaagg aaacctgccc agcagattct cagtccaaca gtttgatgac    300
tatcactctg agatgaacat gagtgccttg gagctagagg actctgccgt gtacttctgt    360
gccagctctc tttctgggc gaactatgct gagcagttct tcggaccagg gacacgactc    420
```

```
accgtcctag aggatctgag aaatgtgact ccacccaagg tctccttgtt tgagccatca    480
aaagcagaga ttgcaaacaa acaaaaggct accctcgtgt gcttggccag gggcttcttc    540
cctgaccacg tggagctgag ctggtgggtg aatggcaagg aggtccacag tggggtcagc    600
acggaccctc aggcctacaa ggagagcaat tatagctact gcctgagcag ccgcctgagg    660
gtctctgcta ccttctggca caatcctcga aaccacttcc gctgccaagt gcagttccat    720 gggcttcag aggaggacaa gtggccagag ggctcaccca aacctgtcac acagaacatc    780
agtgcagagg cctggggccg agcagactgt gggattacct cagcatccta tcaacaaggg    840
gtcttgtctg ccaccatcct ctatgagatc ctgctaggga agccaccct gtatgctgtg    900 cttgtcagta cactggtggt gatggctatg gtcaaaagaa agaattcatg a           951
```

<210> SEQ ID NO 30
<211> LENGTH: 810
<212> TYPE: DNA
<213> ORGANISM: Mus musculus
<220> FEATURE:
<221> NAME/KEY: misc_feature
<223> OTHER INFORMATION: nucleotide sequence encoding the alpha chain
      of the TCR from clone Sp(0.1)A10

<400> SEQUENCE: 30

```
atgctcctgg cgctcctccc agtgctgggg atacactttg tcctgagaga tgcccaagct    60
cagtcagtga cacagcccga tgctcgcgtc actgtctctg aaggagcctc tctgcagctg    120
agatgcaagt attcctactc tgcgacacct tatctgttct ggtatgtcca gtacccgcgg    180
caggggctgc agctgctcct caagtactat tcaggagacc cagtggttca aggagtgaac    240
agcttcgagg ctgagttcag caagagtaac tcttccttcc acctgcagaa agcctctgtg    300
cactggagcg actcggctgt gtacttctgt gctctgagcc acgatagcaa ctatcagttg    360
atctggggct ctgggaccaa gctaattata aagccagaca tccagaaccc agaacctgct    420
gtgtaccagt taaaagatcc tcggtctcag gacagcaccc tctgcctgtt caccgacttt    480
gactcccaaa tcaatgtgcc gaaaaccatg gaatctggaa cgttcatcac tgacaaaact    540
gtgctggaca tgaaagctat ggattccaag agcaatgggg ccattgcctg gagcaaccag    600
acaagcttca cctgccaaga tatcttcaaa gagaccaacg ccacctaccc cagttcagac    660
gttccctgtg atgccacgtt gactgagaaa agctttgaaa cagatatgaa cctaaacttt    720
caaaacctgt cagttatggg actccgaatc ctcctgctga agtagccgg atttaacctg    780 ctcatgacgc tgaggctgtg gtccagttga                                   810
```

<210> SEQ ID NO 31
<211> LENGTH: 951
<212> TYPE: DNA
<213> ORGANISM: Mus musculus
<220> FEATURE:
<221> NAME/KEY: misc_feature
<223> OTHER INFORMATION: nucleotide sequence encoding the beta chain
      of the TCR from clone Sp(0.1)A10

<400> SEQUENCE: 31

```
atgtctaaca ctgccttccc tgaccccgcc tggaacacca cctgctatc ttgggttgct    60 ctctttctcc tgggaacaag ttcagcaaat tctggggttg tccagtctcc aagatacata    120
atcaaaggaa aggagaaag gtccattcta aaatgtattc ccatctctgg atatctctct    180
gtggcctggt atcaacagac tcaggggcag gaactaaagt tcttcattca gcattatgat    240
```

| | |
|---|---|
| aaaatggaga gagataaagg aaacctgccc agcagattct cagtccaaca gtttgatgac | 300 |
| tatcactctg agatgaacat gagtgccttg gagctagagg actctgccgt gtacttctgt | 360 |
| gccagctctc tcgcgggggt taactatgct gagcagttct tcggaccagg acacgactc | 420 |
| accgtcctag aggatctgag aaatgtgact ccacccaagg tctccttgtt tgagccatca | 480 |
| aaagcagaga ttgcaaacaa acaaaaggct accctcgtgt gcttggccag ggcttcttc | 540 |
| cctgaccacg tggagctgag ctggtgggtg aatggcaagg aggtccacag tggggtcagc | 600 |
| acggaccctc aggcctacaa ggagagcaat tatagctact gcctgagcag ccgcctgagg | 660 |
| gtctctgcta ccttctggca caatcctcga aaccacttcc gctgccaagt gcagttccat | 720 |
| gggctttcag aggaggacaa gtggccagag ggctcaccca aacctgtcac acagaacatc | 780 |
| agtgcagagg cctggggccg agcagactgt gggattacct cagcatccta tcaacaaggg | 840 |
| gtcttgtctg ccaccatcct ctatgagatc ctgctaggga aagccaccct gtatgctgtg | 900 |
| cttgtcagta cactggtggt gatggctatg gtcaaaagaa agaattcatg a | 951 |

```
<210> SEQ ID NO 32
<211> LENGTH: 816
<212> TYPE: DNA
<213> ORGANISM: Mus musculus
<220> FEATURE:
<221> NAME/KEY: misc_feature
<223> OTHER INFORMATION: nucleotide sequence encoding the alpha chain
      of the TCR from clone T2(1) C

<400> SEQUENCE: 32
```

| | |
|---|---|
| atgatgaaga catcccttca cactgtattc ctattcttgt ggctatggat ggactgggag | 60 |
| agccatggag agaaggtcga gcaacatgag tctacactga gtgttcgaga gggagacagc | 120 |
| gctgtcatca actgcactta cacagatact gcttcatcat acttcccttg gtacaagcaa | 180 |
| gaagctggaa agagtctcca ctttgtgata gacattcgtt caaatgtgga cagaaaacag | 240 |
| agccaaagac ttatagtttt gttggataag aaagccaaac gattctcccct gcacatcaca | 300 |
| gccacacagc ctgaagattc agccatctac ttctgtgcag caagctcgga tagcaactat | 360 |
| cagttgatct ggggctctgg gaccaagcta attataaagc cagacatcca gaacccagaa | 420 |
| cctgctgtgt accagttaaa agatcctcgg tctcaggaca gcaccctctg cctgttcacc | 480 |
| gactttgact cccaaatcaa tgtgccgaaa accatggaat ctggaacgtt catcactgac | 540 |
| aaaactgtgc tggacatgaa agctatggat tccaagagca tggggccat tgcctggagc | 600 |
| aaccagacaa gcttcacctg ccaagatatc ttcaaagaga ccaacgccac ctaccccagt | 660 |
| tcagacgttc cctgtgatgc cacgttgact gagaaaagct ttgaaacaga tatgaaccta | 720 |
| aactttcaaa acctgtcagt tatgggactc cgaatcctcc tgctgaaagt agccggattt | 780 |
| aacctgctca tgacgctgag gctgtggtcc agttga | 816 |

```
<210> SEQ ID NO 33
<211> LENGTH: 951
<212> TYPE: DNA
<213> ORGANISM: Mus musculus
<220> FEATURE:
<221> NAME/KEY: misc_feature
<223> OTHER INFORMATION: nucleotide sequence encoding the beta chain
      of TCR from clone T2(1)C

<400> SEQUENCE: 33
```

| | |
|---|---|
| atgtctaaca ctgccttccc tgaccccgcc tggaacacca ccctgctatc ttgggttgct | 60 |
| ctctttctcc tgggaacaag ttcagcaaat tctggggttg tccagtctcc aagatacata | 120 |

```
atcaaaggaa agggaaaaag gtccattcta aaatgtattc ccatctctgg acatctctct    180
gtggcctggt atcaacagac tcaggggcag gaactaaagt tcttcattca gcattatgat    240
aaaatggaga gagataaagg aaacctgccc agcagattct cagtccaaca gtttgatgac    300
tatcactctg agatgaacat gagtgccttg gagctagagg actctgccgt gtacttctgt    360
gccagctctc tttctggggc gaactatgct gagcagttct tcggaccagg gacacgactc    420
accgtcctag aggatctgag aaatgtgact ccacccaagg tctccttgtt tgagccatca    480
aaagcagaga ttgcaaacaa cgaaaggct accctcgtgt gcttggccag ggcttcttc     540 cctgaccacg tggagctgag ctggtgggtg aatggcaagg aggtccacag tggggtcagc    600
acggaccctc aggcctacaa ggagagcaat tatagctact gcctgagcag ctgcctgagg    660
gtctctgcta ccttctggca caatcctcga accacttcc gctgccaagt gcagttccat    720
gggctttcag aggaggacaa gtggccagag ggctcaccca aacctgtcac acaggacatc    780
agtgcagagg cctggggccg agcagactgt gggattaccc cagcatccta tcaacaaggg    840
gtcttgtctg ccaccatcct ctacgagatc ctgctaggga agccaccct gtatgctgtg     900 cttgtcagta cactggtggt gatggctatg gtcaaaagaa agaattcatg a              951
```

<210> SEQ ID NO 34
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: amino acid sequence of human gp100 epitope

<400> SEQUENCE: 34

Lys Thr Trp Gly Gln Tyr Trp Gln Val
1               5

<210> SEQ ID NO 35
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: amino acid sequence of murine gp100 epitope

<400> SEQUENCE: 35

Lys Thr Trp Gly Lys Tyr Trp Gln Val
1               5

<210> SEQ ID NO 36
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRAC

<400> SEQUENCE: 36
ggctactttc agcaggagga                                                  20

<210> SEQ ID NO 37
<211> LENGTH: 20

<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRBC

<400> SEQUENCE: 37
aggcctctgc actgatgttc                                           20

<210> SEQ ID NO 38
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRACseq

<400> SEQUENCE: 38
actggtacac agcaggttct gg                                        22

<210> SEQ ID NO 39
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRBCseq

<400> SEQUENCE: 39
aaggagacct tgggtggagt c                                         21

<210> SEQ ID NO 40
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 5'TRA7D3*01

<400> SEQUENCE: 40
caccatgaaa tccttgagtg tttcc                                     25

<210> SEQ ID NO 41
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRA

<400> SEQUENCE: 41
tcaactggac cacagcctca gc                                        22

<210> SEQ ID NO 42
<211> LENGTH: 25
<212> TYPE: DNA
<213> ORGANISM: Artificial
<220> FEATURE:
<223> OTHER INFORMATION: Synthetic

```
<220> FEATURE:
<221> NAME/KEY: misc_feature
<223> OTHER INFORMATION: primer 5'TRB13-3*01

<400> SEQUENCE: 42
caccatgggc tccagactct tcttt                                    25

<210> SEQ ID NO 43
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRBC

<400> SEQUENCE: 43
aggcctctgc actgatgttc                                          20

<210> SEQ ID NO 44
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 5' TCRBCseqreverse

<400> SEQUENCE: 44
aaggagacct tgggtggagt c                                        21

<210> SEQ ID NO 45
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRB

<400> SEQUENCE: 45
tcatgaattc tttcttttga ccatagcc                                 28

<210> SEQ ID NO 46
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 5'TRB13-3*01

<400> SEQUENCE: 46
caccatgggc tccagactct tcttt                                    25

<210> SEQ ID NO 47
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' TCRB
```

-continued

<400> SEQUENCE: 47
tcatgaattc tttcttttga ccatagcc                                        28

<210> SEQ ID NO 48
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 5' alpha RNA

<400> SEQUENCE: 48
aactaatacg actcactata gggagacacc atgaaatcct tgagtgtttc c              51

<210> SEQ ID NO 49
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' alpha RNA

<400> SEQUENCE: 49
tttttttttt tttttttttt tttttttttt tttttttttt tttttttttt tttttttttt    60
tttttcaact ggaccacagc ctcagc                                          86

<210> SEQ ID NO 50
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 5' beta RNA

<400> SEQUENCE: 50
aactaatacg actcactata gggagacacc atgggctcca gactcttctt t              51

<210> SEQ ID NO 51
<211> LENGTH: 93
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: primer 3' beta RNA

<400> SEQUENCE: 51
tttttttttt tttttttttt tttttttttt tttttttttt tttttttttt tttttttttt    60 tttttttcatg aattctttct tttgaccata gcc                                 93

<210> SEQ ID NO 52
<211> LENGTH: 98
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: amino acid sequence of variable region of
      T2(1)B/C with variation X at position 17 is any amino acid

```
<220> FEATURE:
<221> NAME/KEY: misc_feature
<222> LOCATION: (17)..(17)
<223> OTHER INFORMATION: Xaa can be any naturally occurring amino acid

<400> SEQUENCE: 52

Asn Ser Gly Val Val Gln Ser Pro Arg Tyr Ile Ile Lys Gly Lys Gly
1               5                   10                  15

Xaa Arg Ser Ile Leu Lys Cys Ile Pro Ile Ser Gly His Leu Ser Val
                20                  25                  30

Ala Trp Tyr Gln Gln Thr Gln Gly Gln Glu Leu Lys Phe Phe Ile Gln
            35                  40                  45

His Tyr Asp Lys Met Glu Arg Asp Lys Gly Asn Leu Pro Ser Arg Phe
        50                  55                  60

Ser Val Gln Gln Phe Asp Asp Tyr His Ser Glu Met Asn Met Ser Ala
65                  70                  75                  80

Leu Glu Leu Glu Asp Ser Ala Val Tyr Phe Cys Ala Ser Ser Leu Ser
                85                  90                  95

Gly Ala

<210> SEQ ID NO 53
<211> LENGTH: 316
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: amino acid sequence of T2(1)B/C with variations
      X at position 46, 168, 218, and/or 259 is/are any amino acid.
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid

<400> SEQUENCE: 53

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
                20                  25                  30

Val Val Gln Ser Pro Arg Tyr Ile Ile Lys Gly Lys Gly Xaa Arg Ser
            35                  40                  45

Ile Leu Lys Cys Ile Pro Ile Ser Gly His Leu Ser Val Ala Trp Tyr
        50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Ser Gly Ala Asn
```

-continued

```
        115                 120                 125

Tyr Ala Glu Gln Phe Phe Gly Pro Gly Thr Arg Leu Thr Val Leu Glu
    130                 135                 140

Asp Leu Arg Asn Val Thr Pro Pro Lys Val Ser Leu Phe Glu Pro Ser
145                 150                 155                 160

Lys Ala Glu Ile Ala Asn Lys Xaa Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Ser Thr Asp Pro Gln Ala Tyr Lys Glu
        195                 200                 205

Ser Asn Tyr Ser Tyr Cys Leu Ser Ser Xaa Leu Arg Val Ser Ala Thr
    210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Xaa Ile Ser Ala Glu Ala Trp Gly Arg Ala Asp Cys Gly Ile
            260                 265                 270

Thr Ser Ala Ser Tyr Gln Gln Gly Val Leu Ser Ala Thr Ile Leu Tyr
        275                 280                 285

Glu Ile Leu Leu Gly Lys Ala Thr Leu Tyr Ala Val Leu Val Ser Thr
    290                 295                 300

Leu Val Val Met Ala Met Val Lys Arg Lys Asn Ser
305                 310                 315

<210> SEQ ID NO 54
<211> LENGTH: 303
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: amino acid sequence beta chain of Sp(0.01)A
      with variation in constant region
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid

<400> SEQUENCE: 54

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
            20                  25                  30

Thr Gly Gly Lys Val Thr Leu Ser Cys His Gln Thr Asn Asn His Asp
        35                  40                  45

Tyr Met Tyr Trp Tyr Arg Gln Asp Thr Gly His Gly Leu Arg Leu Ile
    50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Ser Leu Ser Gln Thr Ala Val Tyr Phe Cys Ala Ser Ser
```

```
                100             105              110
Pro Gly Gly Gly Gly Glu Gln Tyr Phe Gly Pro Gly Thr Arg Leu Thr
            115                 120             125

Val Leu Glu Asp Leu Arg Asn Val Thr Pro Lys Val Ser Leu Phe
        130              135             140

Glu Pro Ser Lys Ala Glu Ile Ala Asn Lys Arg Lys Ala Thr Leu Val
145             150              155             160

Cys Leu Ala Arg Gly Phe Phe Pro Asp His Val Glu Leu Ser Trp Trp
                165             170              175

Val Asn Gly Lys Glu Val His Ser Gly Val Ser Thr Asp Pro Gln Ala
            180             185             190

Tyr Lys Glu Ser Asn Tyr Ser Tyr Cys Leu Ser Ser Xaa Leu Arg Val
        195             200             205

Ser Ala Thr Phe Trp His Asn Pro Arg Asn His Phe Arg Cys Gln Val
        210             215             220

Gln Phe His Gly Leu Ser Glu Glu Asp Lys Trp Pro Glu Xaa Ser Pro
225             230             235             240

Lys Pro Val Thr Gln Asn Ile Ser Ala Glu Ala Trp Gly Arg Ala Asp
            245             250             255

Cys Gly Ile Thr Ser Ala Ser Tyr Gln Gln Gly Val Leu Ser Ala Thr
            260             265             270

Ile Leu Tyr Glu Ile Leu Leu Gly Lys Ala Thr Leu Tyr Ala Val Leu
        275             280             285

Val Ser Thr Leu Val Val Met Ala Met Val Lys Arg Lys Asn Ser
290             295             300
```

<210> SEQ ID NO 55
<211> LENGTH: 423
<212> TYPE: DNA
<213> ORGANISM: Homo sapiens
<220> FEATURE:
<221> NAME/KEY: misc_feature
<223> OTHER INFORMATION: Human alpha chain constant region

<400> SEQUENCE: 55

| | | | | | |
|---|---|---|---|---|---|
| atccagaacc | ctgaccctgc | cgtgtaccag | ctgagagact | ctaaatccag | tgacaagtct | 60 |
| gtctgcctat | tcaccgattt | tgattctcaa | acaaatgtgt | cacaaagtaa | ggattctgat | 120 |
| gtgtatatca | cagacaaaac | tgtgctagac | atgaggtcta | tggacttcaa | gagcaacagt | 180 |
| gctgtggcct | ggagcaacaa | atctgacttt | gcatgtgcaa | acgccttcaa | caacagcatt | 240 |
| attccagaag | acaccttctt | ccccagccca | gaaagttcct | gtgatgtcaa | gctggtcgag | 300 |
| aaaagctttg | aaacagatac | gaacctaaac | tttcaaaacc | tgtcagtgat | tgggttccga | 360 |
| atcctcctcc | tgaaagtggc | cgggtttaat | ctgctcatga | cgctgcggct | gtggtccagc | 420 |
| tga | | | | | | 423 |

<210> SEQ ID NO 56
<211> LENGTH: 534
<212> TYPE: DNA
<213> ORGANISM: Homo sapiens
<220> FEATURE:
<221> NAME/KEY: misc_feature
<223> OTHER INFORMATION: Human beta chain constant region

<400> SEQUENCE: 56

| | | | | | |
|---|---|---|---|---|---|
| gaggacctga | acaaggtgtt | cccacccgag | gtcgctgtgt | ttgagccatc | agaagcagag | 60 |
| atctcccaca | cccaaaaggc | cacactggtg | tgcctggcca | caggcttctt | ccctgaccac | 120 |

```
gtggagctga gctggtgggt gaatgggaag gaggtgcaca gtggggtcag cacggacccg    180
cagcccctca aggagcagcc cgccctcaat gactccagat actgcctgag cagccgcctg    240
agggtctcgg ccaccttctg gcagaacccc cgcaaccact tccgctgtca agtccagttc    300
tacgggctct cggagaatga cgagtggacc caggataggg ccaaacccgt cacccagatc    360
gtcagcgccg aggcctgggg tagagcagac tgtggcttta cctcggtgtc ctaccagcaa    420
ggggtcctgt ctgccaccat cctctatgag atcctgctag ggaaggccac cctgtatgct    480
gtgctggtca gcgcccttgt gttgatggcc atggtcaaga gaaaggattt ctga          534
```

<210> SEQ ID NO 57
<211> LENGTH: 7929
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7552)..(7555)
<223> OTHER INFORMATION: n is a, c, g, or t

<400> SEQUENCE: 57

```
ccatgtcatc cttgagtgtt tccctagtgg tcctgtggct ccagttaaac tgggtgaaca     60
gccagcagaa ggtgcagcag agcccagaat ccctcattgt cccagaggga gccatgacct    120
ctctcaactg cactttcagc gacagtgctt ctcagtattt tgcatggtac agacagcatt    180
ctgggaaagc ccccaaggca ctgatgtcca tcttctccaa tggtgaaaaa gaagaaggca    240
gattcacaat tcacctcaat aaagccagtc tgcatttctc gctacacatc agagactccc    300
agcccagtga ctctgctctc tacctctgtg cagccaataa ctatgcccag ggattaacct    360
tcggtcttgg caccagagta tctgtgtttc cctacatcca gaacccagaa cctgctgtgt    420
accagttaaa agatcctcgg tctcaggaca gcaccctctg cctgttcacc gactttgact    480
cccaaatcaa tgtgccgaaa accatggaat ctggaacgtt catcactgac aaaactgtgc    540
tggacatgaa agctatggat tccaagagca atgggccat tgcctggagc aaccagacaa    600
gcttcacctg ccaagatatc ttcaaagaga ccaacgccac ctaccccagt tcagacgttc    660
cctgtgatgc cacgttgact gagaaaagct ttgaaacaga tatgaaccta aactttcaaa    720
acctgtcagt tatgggactc cgaatcctcc tgctgaaagt agccggattt aacctgctca    780
tgacgctgag gctgtggtcc agttgagcgg ccgctctaga actagtggat ctccacgtgg    840
cggctagtac tccggtattg cggtacccct gtacgcctgt tttatactcc cttcccgtaa    900
cttagacgca caaaaccaag ttcaatagaa gggggtacaa accagtacca ccacgaacaa    960
gcacttctgt ttccccggtg atgtcgtata gactgcttgc gtggttgaaa gcgacggatc   1020
cgttatccgc ttatgtactt cgagaagccc agtaccacct cggaatcttc gatgcgttgc   1080
gctcagcact caaccccaga gtgtagctta ggctgatgag tctggacatc cctcaccggt   1140
gacggtggtc caggctgcgt tggcggccta cctatggcta acgccatggg acgctagttg   1200
tgaacaaggt gtgaagagcc tattgagcta cataagaatc ctccggcccc tgaatgcggc   1260
taatcccaac ctcggagcag gtggtcacaa accagtgatt ggcctgtcgt aacgcgcaag   1320
tccgtggcgg aaccgactac tttgggtgtc cgtgtttcct tttatttat tgtggctgct   1380 tatggtgaca atcacagatt gttatcataa agcgaattgg ataggatcaa gcttatcgat   1440
gggctccaga ctcttctttg tggttttgat tctcctgtgt gcaaaacaca tggaggctgc   1500
```

```
agtcacccaa agtccaagaa gcaaggtggc agtaacagga ggaaaggtga cattgagctg     1560
tcaccagact aataaccatg actatatgta ctggtatcgg caggacacgg ggcatgggct     1620
gaggctgatc cattactcat atgtcgctga cagcacggag aaaggagata tccctgatgg     1680
gtacaaggcc tccagaccaa gccaagagaa tttctctctc attctggagt tggcttccct     1740
ttctcagaca gctgtatatt tctgtgccag cagccctggg ggggggggg aacagtactt     1800 cggtcccggc accaggctca cggttttaga ggatctgaga aatgtgactc cacccaaggt     1860
ctccttgttt gagccatcaa aagcagagat tgcaaacaaa cgaaaggcta ccctcgtgtg     1920
cttggccagg ggcttcttcc ctgaccacgt ggagctgagc tggtgggtga atggcaagga     1980
ggtccacagt ggggtcagca cggaccctca ggcctacaag gagagcaatt atagctactg     2040
cctgagcagc cgcctgaggg tctctgctac cttctggcac aatcctcgaa accacttccg     2100
ctgccaagtg cagttccatg gcttttcaga ggaggacaag tggccagagg gctcacccaa     2160
acctgtcaca cagaacatca gtgcagaggc ctggggccga gcagactgtg ggattacctc     2220
agcatcctat caacaagggg tcttgtctgc caccatcctc tatgagatcc tgctaggaaa     2280
agccaccctg tatgctgtgc ttgtcagtac actggtggtg atggctatgg tcaaaagaaa     2340
gaattcatga taagcttcga attctgcagt cgacggtacc gcgggcccgg gatccgataa     2400
aataaaagat tttatttagt ctccagaaaa aggggggaat gaaagacccc acctgtaggt     2460
ttggcaagct agcttaagta cgccatttt gcaaggcatg gaaaatacat aactgagaat     2520
agagaagttc agatcaaggt taggaacaga gagacagcag aatatgggcc aaacaggata     2580
tctgtggtaa gcagttcctg ccccggctca gggccaagaa cagatggtcc ccagatgcgg     2640
tcccgccctc agcagtttct agagaaccat cagatgtttc cagggtgccc caaggacctg     2700
aaaatgaccc tgtgccttat ttgaactaac caatcagttc gcttctcgct tctgttcgcg     2760
cgcttctgct ccccgagctc aataaaagag cccacaaccc ctcactcggc gcgccagtcc     2820
tccgatagac tgcgtcgccc gggtacccgt gtatccaata aaccctcttg cagttgcatc     2880
cgacttgtgg tctcgctgtt ccttgggagg gtctcctctg agtgattgac tacccgtcag     2940
cgggggtctt tcatgggtaa cagtttcttg aagttggaga caacattct gagggtagga     3000 gtcgaatatt aagtaatcct gactcaatta gccactgttt tgaatccaca tactccaata     3060
ctcctgaaat ccatcgatgg agttcattat ggacagcgca gaaagagctg gggagaattg     3120
tgaaattgtt atccgctcac aattccacac aacatacgag ccggaagcat aaagtgtaaa     3180
gcctggggtg cctaatgagt gagctaactc acattaattg cgttgcgctc actgcccgct     3240
ttccagtcgg gaaacctgtc gtgccagctg cattaatgaa tcggccaacg cgcggggaga     3300
ggcggtttgc gtattgggcg ctcttccgct tcctcgctca ctgactcgct gcgctcggtc     3360
gttcggctgc ggcgagcggt atcagctcac tcaaaggcgg taatacggtt atccacagaa     3420 tcagggggata acgcaggaaa gaacatgtga gcaaaaggcc agcaaaaggc caggaaccgt     3480
aaaaaggccg cgttgctggc gttttccat aggctccgcc cccctgacga gcatcacaaa     3540
aatcgacgct caagtcagag gtggcgaaac ccgacaggac tataaagata ccaggcgttt     3600
ccccctggaa gctccctcgt gcgctctcct gttccgaccc tgccgcttac cggatacctg     3660
tccgcctttc tcccttcggg aagcgtggcg ctttctcata gctcacgctg taggtatctc     3720
agttcggtgt aggtcgttcg ctccaagctg ggctgtgtgc acgaaccccc cgttcagccc     3780
gaccgctgcg ccttatccgg taactatcgt cttgagtcca acccggtaag acacgactta     3840
tcgccactgg cagcagccac tggtaacagg attagcagag cgaggtatgt aggcggtgct     3900
```

```
acagagttct tgaagtggtg gcctaactac ggctacacta aaggacagt atttggtatc    3960 tgcgctctgc tgaagccagt taccttcgga aaaagagttg gtagctcttg atccggcaaa    4020
caaaccaccg ctggtagcgg tggttttttt gtttgcaagc agcagattac gcgcagaaaa    4080
aaaggatctc aagaagatcc tttgatcttt tctacgggt ctgacgctca gtggaacgaa     4140
aactcacgtt aagggatttt ggtcatgaga ttatcaaaaa ggatcttcac ctagatcctt    4200
ttaaattaaa aatgaagttt taaatcaatc taaagtatat atgagtaaac ttggtctgac    4260
agttaccaat gcttaatcag tgaggcacct atctcagcga tctgtctatt tcgttcatcc    4320
atagttgcct gactccccgt cgtgtagata actacgatac gggagggctt accatctggc    4380
cccagtgctg caatgatacc gcgagaccca cgctcaccgg ctccagattt atcagcaata    4440
aaccagccag ccggaagggc cgagcgcaga agtggtcctg caactttatc cgcctccatc    4500
cagtctatta attgttgccg ggaagctaga gtaagtagtt cgccagttaa tagtttgcgc    4560
aacgttgttg ccattgctac aggcatcgtg gtgtcacgct cgtcgtttgg tatggcttca    4620
ttcagctccg gttcccaacg atcaaggcga gttacatgat cccccatgtt gtgcaaaaaa    4680
gcggttagct ccttcggtcc tccgatcgtt gtcagaagta agttggccgc agtgttatca    4740
ctcatggtta tggcagcact gcataattct cttactgtca tgccatccgt aagatgcttt    4800
tctgtgactg gtgagtactc aaccaagtca ttctgagaat agtgtatgcg gcgaccgagt    4860
tgctcttgcc cggcgtcaat acgggataat accgcgccac atagcagaac tttaaaagtg    4920
ctcatcattg gaaaacgttc ttcggggcga aaactctcaa ggatcttacc gctgttgaga    4980
tccagttcga tgtaacccac tcgtgcaccc aactgatctt cagcatcttt tactttcacc    5040
agcgtttctg ggtgagcaaa aacaggaagg caaaatgccg caaaaaaggg aataagggcg    5100
acacggaaat gttgaatact catactcttc ctttttcaat attattgaag catttatcag    5160
ggttattgtc tcatgagcgg atacatattt gaatgtattt agaaaaataa acaaataggg    5220
gttccgcgca catttccccg aaaagtgcca cctgacgtct aagaaaccat tattatcatg    5280
acattaacct ataaaaatag gcgtatcacg aggccctttc gtctcgcgcg tttcggtgat    5340
gacggtgaaa acctctgaca catgcagctc ccggagacgg tcacagcttg tctgtaagcg    5400
gatgccggga gcagacaagc ccgtcagggc gcgtcagcgg gtgttggcgg gtgtcggggc    5460
tggcttaact atgcggcatc agagcagatt gtactgagag tgcaccatat gcggtgtgaa    5520
ataccgcaca gatgcgtaag gagaaaatac cgcatcaggc gccattcgcc attcaggctg    5580
cgcaactgtt gggaagggcg atcggtgcgg gcctcttcgc tattacgcca gctggcgaaa    5640
gggggatgtg ctgcaaggcg attaagttgg gtaacgccag ggttttccca gtcacgacgt    5700
tgtaaaacga cggccagtgc cacgctctcc cttatgcgac tcctgcatta ggaagcagcc    5760
cagtagtagg ttgaggccgt tgagcaccgc cgccgcaagg aatggtgcat gcaaggagat    5820
ggcgcccaac agtcccccgg ccacgggcc tgccaccata cccacgccga aacaagcgct     5880
catgagcccg aagtggcgag cccgatcttc cccatcggtg atgtcggcga tataggcgcc    5940
agcaaccgca cctgtggcgc cggtgatgcc ggccacgatg cgtccggcgt agaggcgatt    6000
taaagacagg atatcagtgg tccaggctct agttttgact caacaatatc accagctgaa    6060
gcctatagag tacgagccat agataaaata aaagatttta tttagtctcc agaaaagggg    6120
gggaatgaaa gaccccacct gtaggtttgg caagctagct taagtaacgc cattttgcaa    6180
ggcatggaaa atacataact gagaatagag aagttcagat caaggttagg aacagagaga    6240
```

-continued

```
cagcagaata tgggccaaac aggatatctg tggtaagcag ttcctgcccc ggctcagggc    6300
caagaacaga tggtccccag atgcggtccc gccctcagca gtttctagag aaccatcaga    6360
tgtttccagg gtgcccaag gacctgaaaa tgaccctgtg ccttatttga actaaccaat    6420
cagttcgctt ctcgcttctg ttcgcgcgct tctgctcccc gagctcaata aaagagccca    6480 caaccctca ctcggcgcgc cagtcctccg atagactgcg tcgcccgggt acccgtattc    6540
ccaataaagc ctcttgctgt ttgcatccga atcgtggact cgctgatcct tgggagggtc    6600
tcctcagatt gattgactgc ccacctcggg ggtctttcat ttggaggttc caccgagatt    6660
tggagacccc tgcctaggga ccaccgaccc ccccgccggg aggtaagctg gccagcggtc    6720
gtttcgtgtc tgtctctgtc tttgtgcgtg tttgtgccgg catctaatgt ttgcgcctgc    6780
gtctgtacta gttagctaac tagctctgta tctggcggac ccgtggtgga actgacgagt    6840
tcggaacacc cggccgcaac cctgggagac gtcccaggga cttcggggggc cgttttgtg    6900 gcccgacctg agtccaaaaa tcccgatcgt tttggactct ttggtgcacc cccttagag    6960 gagggatatg tggttctggt aggagacgag aacctaaaac agttcccgcc tccgtctgaa    7020
tttttgcttt cggtttggga ccgaagccgc gccgcgcgtc ttgtctgctg cagcatcgtt    7080
ctgtgttgtc tctgtctgac tgtgtttctg tatttgtctg agaatatggg cccgggctag    7140
cctgttacca ctcccttaag tttgacctta ggtcactgga aagatgtcga gcggatcgct    7200
cacaaccagt cggtagatgt caagaagaga cgttgggtta ccttctgctc tgcagaatgg    7260 ccaacctta acgtcggatg gccgcgagac ggcacccttta accgagacct catcacccag    7320
gttaagatca aggtcttttc acctggcccg catggacacc cagaccaggt cccctacatc    7380
gtgacctggg aagccttggc ttttgacccc cctccctggg tcaagccctt tgtacaccct    7440
aagcctccgc ctcctcttcc tccatccgcc ccgtctctcc cccttgaacc tcctcgttcg    7500
accccgcctc gatcctccct ttatccagcc ctcactcctt ctctaggcgc cnnnncatat    7560
gagatcttat atggggcacc cccgcccctt gtaaacttcc ctgaccctga catgacaaga    7620
gttactaaca gcccctctct ccaagctcac ttacaggctc tctacttagt ccagcacgaa    7680
gtctggagac ctctggcggc agcctaccaa gaacaactgg accgaccggt ggtacctcac    7740
ccttaccgag tcggcgacac agtgtgggtc cgccgacacc agactaagaa cctagaacct    7800
cgctggaaag gaccttacac agtcctgctg accaccccca ccgccctcaa agtagacggc    7860
atcgcagctt ggatacacgc cgcccacgtg aaggctgccg accccggggg tggaccatcc    7920
tctagaccg                                                            7929
```